US012807588B2

(12) United States Patent
Yang et al.

(10) Patent No.: US 12,807,588 B2
(45) Date of Patent: Nov. 24, 2026

(54) NON-COVALENT PI-PI INTERACTION CONSTRUCTED ORGANIC FRAMEWORKS (PiOFs)

(71) Applicant: The Regents of the University of California, Oakland, CA (US)

(72) Inventors: Yang Yang, Oakland, CA (US); Dong Meng, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 326 days.

(21) Appl. No.: 18/681,462

(22) PCT Filed: Jul. 29, 2022

(86) PCT No.: PCT/US2022/074347
§ 371 (c)(1),
(2) Date: Feb. 5, 2024

(87) PCT Pub. No.: WO2023/015143
PCT Pub. Date: Feb. 9, 2023

(65) Prior Publication Data

US 2024/0308972 A1 Sep. 19, 2024

Related U.S. Application Data

(60) Provisional application No. 63/229,910, filed on Aug. 5, 2021.

(51) Int. Cl.
*C07D 333/78* (2006.01)
*C09K 9/02* (2006.01)

(52) U.S. Cl.
CPC .............. *C07D 333/78* (2013.01); *C09K 9/02* (2013.01); *C09K 2211/1092* (2013.01)

(58) Field of Classification Search
CPC . C07D 333/78; C09K 9/02; C09K 2211/1092
See application file for complete search history.

(56) References Cited

U.S. PATENT DOCUMENTS

2017/0368178 A1* 12/2017 Miljanic ................ A61K 31/08
2021/0162371 A1* 6/2021 Ma ...................... B01J 20/28088

FOREIGN PATENT DOCUMENTS

CN 111909384 A * 11/2020 ........... A61K 31/337

OTHER PUBLICATIONS

Dong Meng, Jonathan Lee Yang, Chengyi Xiao, Rui Wanga, and Yang Yanga, Noncovalent pi-stacked robust topological organic framework, PNAS | Aug. 25, 2020 | vol. 117 | No. 34 | 20397-20403 (Year: 2020).*

(Continued)

*Primary Examiner* — Bijan Ahvazi
(74) *Attorney, Agent, or Firm* — Venable LLP; Ryan Ward

(57) ABSTRACT

A composition having a pi-pi interaction-constructed organic framework (pi-OF). The pi-OF includes a plurality of molecular structures, each molecular structure, including: (a) a centroid core having two spirobifluorene (SF) units, the two SF units forming a rigid biplanar conjugated cruciform-shaped spirofluorene, the two SF units forming an essentially orthogonal configuration; and (b) a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both. The composition also includes a bioactive agent absorbed into the pi-OF.

21 Claims, 33 Drawing Sheets

(56) References Cited

OTHER PUBLICATIONS

Nan Zhang, Shihao Ding, Kai Wang, Quan Lyu, and Wei Xiao Sun, Efficient transparent quantum-dot light-emitting diodes with an inverted architecture, vol. 11, No. 7/Jul. 1, 2021/Optical Materials Express 2145-2152. (Year: 2021).*
Meng, D. et al., "Noncovalent ?—stacked robust topological organic framework", Proceedings of the National Academy of Sciences, Aug. 11, 2020, vol. 117, No. 34, pp. 20397-20403.
Zhang, N. et al., "Efficient transpment quantum-dot light-emitting diodes with an inverted mchitecture", Optical Materials Express, Jul. 1, 2021, vol. 11, No. 7, pp. 2145-2152.
Rosi et al., "Hydrogen storage in microporous metal-organic frameworks", Science, (2003), vol. 300, pp. 1127-1129.
Corma, "From Microporous to Mesoporous Molecular Sieve Materials and Their Use in Catalysis", Chem. Rev., (1997), vol. 97, pp. 2373-2419.
Horcajada et al., "Porous metal-organic-framework nanoscale carriers as a potential platform for drug delivery and imaging", Nat. Mater., (Feb. 2010), vol. 9, pp. 172-178.
McKinlay et al., "BioMOFs: Metal-Organic Frameworks for Biological and Medical Applications", Angew. Chem., Int. Ed., (2010), vol. 49, pp. 6260-6266.
Davis, "Ordered porous materials for emerging applications", Nature, (Jun. 20, 2002), vol. 417, pp. 813-821.
Avci et al., "Self-assembly of polyhedral metal-organic framework particles into three dimensional ordered superstructures", Nat. Chem., (Jan. 2018), vol. 10, pp. 78-84.
Ma et al., "Single-crystal X-ray diffraction structures of covalent organic frameworks", Science, (Jul. 6, 2018), vol. 361, (5 pages).
Navarro, "The dynamic art of growing COF crystals", Science, (Jul. 6, 2018), vol. 361, Issue 6397, p. 35.
Jiang et al., "Covalent Chemistry Beyond Molecules", J. Am. Chem. Soc., (Feb. 10, 2016), vol. 138, pp. 3255-3265.
Huang et al., "Covalent organic frameworks: a materials platform for structural and functional designs", Nat. Rev. Mater., (Oct. 2016), vol. 1, (19 pages).
He et al., "A microporous hydrogen-bonded organic framework for highly selective C2H2/C2H4 separation at ambient temperature", J. Am. Chem. Soc., (2011), vol. 133, pp. 1457014573.
Li et al., "A rod-packing microporous hydrogen-bonded organic framework for highly selective separation of C2H2/CO2 at room temperature", Angew. Chem. Int. Ed., (2015), vol. 54, pp. 574-577.
Hu et al., "An ultrastable and easily regenerated hydrogen-bonded organic molecular framework with permanent porosity", Angew. Chem. Int. Ed., (2017), vol. 56, pp. 2101-2104.
Yaghi et al., "Selective binding and removal of guests in a microporous metalorganic framework", Nature, (Dec 14, 1995), vol. 378, pp. 703-706.
Yaghi et al., "Selective guest binding by tailored channels in a 3-D porous zinc(II)-benzenetricarboxylate network.", J. Am. Chem. Soc, (1997), vol. 119, pp. 2861-2868.
Evans et al., "Seeded growth of single-crystal two-dimensional covalent organic Submitted Manuscript: Confidential frameworks", Science, (Jul. 6, 2018), vol. 361, pp. 52-57.
Kondo et al., "Rational synthesis of stable channel-like cavities with methane gas adsorption properties: [{Cu2(pzdc)2 (L)}n] (pzdc= pyrazine-2,3-dicarboxylate; L=a pillar ligand)", Angew. Chem. Int. Ed., (1999), vol. 38, pp. 140-143.
Shen, et al., "Ordered macro-microporous 5 metal-organic framework single crystals", Science, (Jan. 12, 2018), vol. 359, (5 pages).
Chen et al., "Lowering coefficient of friction in Cu alloys with stable gradient nanostructures", Sci. Adv., (Dec 9, 2016), vol. 2, (7 pages).
Côté et al., "Porous, crystalline, covalent organic frameworks", Science, (Nov. 18, 2005), vol. 310, pp. 1166-117010.
Lyu et al., "Highly efficient red phosphorescent OLEDs based on non-conjugated silicon-cored spirobifluorene derivative doped with Ir-complexes", Adv. Funct. Mater., (2009), vol. 19, pp. 420-427.
Qiu et al., "Nonfullerene small molecular acceptors with a three-dimensional (3D) structure for organic solar cells", Chem. Mater., (2016), vol. 28, pp. 6770-6778.
Heredia et al., "Spirobifluorene-bridged donor/acceptor dye for organic dye-sensitized solar cells", Org. Lett., (2010), vol. 12, No. 1, pp. 12-15.
Han et al., "Improving the electron mobility of ITIC by end-group modulation: the role of fluorination and pi-extension", Sol. RRL., (2019), vol. 3, (5 pages).
Lin et al., "An electron acceptor challenging fullerenes for efficient polymer solar cells", Adv. Mater., (2015), vol. 27, pp. 1170-1174.
Han et al., "From molecular packing structures to electronic processes: theoretical simulations for organic solar cells", Adv. Energy Mater., (2018), vol. 8, (16 pages).
Bezzu et al., "Heme-like coordination chemistry within nanoporous molecular crystals", Science, (Mar. 26, 2010), vol. 327, pp. 1627-1630.
Msayib et al., "Nitrogen and hydrogen adsorption by an organic microporous crystal", Angew. Chem. Int. Ed., (2009), vol. 48, pp. 3273-3277.
Chen et al., "Multiphase design of autonomic self-healing thermoplastic elastomers", Nat. Chem., (2012), vol. 4, pp. 467-472.
Yamagishi et al., "Self-assembly of lattices with high structural complexity from a geometrically simple molecule", Science, (Sep. 21, 2018), vol. 361, (4 pages).
Cordier et al., "Self-healing and thermoreversible rubber from supramolecular assembly", Nature, (Feb. 2008), vol. 451, pp. 977-980.
Jiang et al., "Organic single-crystalline ribbons of a rigid "H"-type anthracene derivative and high-performance, short-channel field-effect transistors of individual micro/nanometer-sized ribbons fabricated by an "organic ribbon mask" technique", Adv. Mater., (2008), vol. 20, pp. 2735-2740.
Yavuz et al., "Theoretical Study of the Molecular Ordering, Paracrystallinity, And Charge Mobilities of Oligomers in Different Crystalline Phases", J. Am. Chem. Soc, (2015), vol. 137, pp. 2856-2866.
Tsutsui et al., "Unraveling Unprecedented Charge Carrier Mobility through Structure Property Relationship of Four Isomers of Didodecyl[1]benzothieno[3,2-b][1]benzothiophene", Adv. Mater., (2016), vol. 28, pp. 7106-7114.
Rühle et al., "Microscopic Simulations of Charge Transport in Disordered Organic Semiconductors.", J. Chem. Theory Comput., (2011), vol. 7, pp. 3335-3345.

* cited by examiner

G

H

I $^1H$ NMR Spectra of Compound 1 (400 MHz, $CDCl_3$, 298.5 K)

$^1H$ NMR Spectra of Compound 2 (400 MHz, $CDCl_3$, 298.5 K)

$^1H$ NMR Spectra of Compound 3 (400 MHz, $CDCl_3$, 298.5 K)

$^1$H NMR Spectra of Compound 4 (400 MHz, $CDCl_3$, 298.5 K)

$^1H$ NMR Spectra of SFIC (500 MHz, $C_2D_2Cl_4$, 373.2 K)

$^{13}C$ NMR Spectra of SFIC (500 MHz, $C_2D_2Cl_4$, 373.2 K)

A

B

NON-COVALENT PI-PI INTERACTION CONSTRUCTED ORGANIC FRAMEWORKS (PiOFs)

CROSS-REFERENCE TO RELATED APPLICATIONS

This patent application is a U.S. National Stage Application of PCT/US2022/074347, filed Jul. 29, 2022, which claims priority benefit from U.S. provisional patent application No. 63/229,910, filed on Aug. 5, 2021, the entire content of which is incorporated herein by reference.

STATEMENT OF GOVERNMENT INTEREST

This invention was made with government support under Grant Number FA2386-18-1-4094, awarded by the United States Air Force. The government has certain rights in the invention.

BACKGROUND

1. Technical Field

The field of currently claimed embodiments of this invention relates to porous materials, and more particularly to non-covalent π···π-Interaction-constructed organic frameworks (πOFs) and use in photo-electronics, detection and drug and bioactive agent delivery applications.

2. Discussion of Related Art

Ordered microporous materials have aroused extensive interest due to their outstanding performance and numerous existing and potential applications, such as gas storage and separation, heterogeneous catalysis, drug release and proton conduction. The important families of microporous crystalline materials include covalent organic frameworks (COFs), held together by strong covalent bonds, metal-organic frameworks (MOFs) linked via strong coordination bonds and hydrogen-bonded organic frameworks (HOFs) connected through weak hydrogen bonding, all of which have been developed over the past decade. These microporous materials not only expanded the concept of molecular architectures but also offer extensive applications that serve as an inspiration to explore novel multifunctional materials. However, among the numerous applications, integration of organic frameworks into organic electronics, such as organic field-effect transistors (OFET), organic light-emitting diodes (OLED) and solar cells, has been challenging due to poor electrical conductivity and solubility through coordination, covalent and hydrogen bonds.

Therefore, there remains a need for improved electronic and photonic materials among other applications. The following describes a novel material that can be used in many photo-electronics and detection applications, for example.

SUMMARY

An embodiment of the present invention is directed to a composition that includes a pi-pi interaction-constructed organic framework (pi-OF) and a bioactive agent absorbed into said pi-OF. The pi-OF includes a plurality of molecular structures, each molecular structure including a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit including a 3-(dicyanomethylidene) indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

Another embodiment of the present invention is directed to a method of administering a bioactive agent to an animal or a human that includes injecting the composition of the paragraph above into the animal or human and illuminating the composition after the injecting with light to cause at least a portion of the bioactive agent to be released in response to the illuminating.

Another embodiment of the present invention is directed to a molecular structure (SFIC) that includes a centroid core having two spirobifluorene (SF) units, the two SF units forming a rigid biplanar conjugated cruciform-shaped spirobifluorene, the two SF units forming an essentially orthogonal configuration, and a plurality of multijoint fragment units, each unit comprising a 3-(dicyanomethylidene) indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

Another embodiment of the present invention is directed to a pi-pi interaction-constructed organic framework (pi-OF) that includes a plurality of molecular structures, each molecular structure including a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

Another embodiment of the present invention is directed to a transistor device that includes a substrate; a plurality of electrodes disposed on the substrate; and a SFIC microplate. The SFIC microplate includes a molecular structure that includes a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both. The SFIC microplate is disposed on the plurality of electrodes.

Another embodiment of the present invention is directed to an organic light emitting device that includes a substrate electrode; an electron transport layer and a hole transport layer disposed on the substrate electrode; and a SFIC layer sandwiched between the electron transport layer and the hole transport layer. The SFIC layer has a molecular structure that includes a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1B:
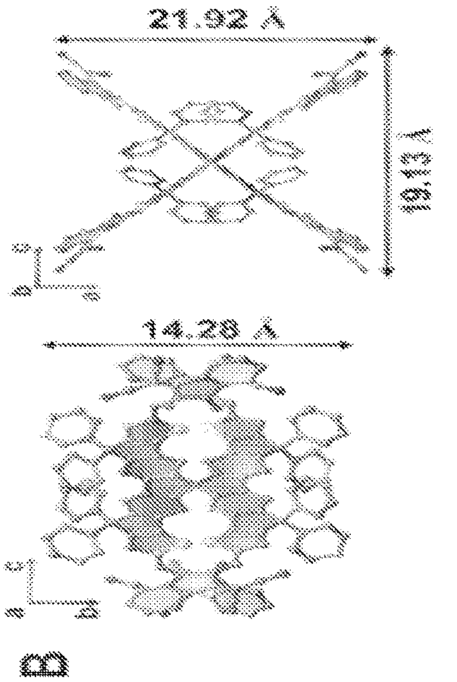
FIG. 1B shows the single-crystal X-ray molecular structure [top (Left) and side (Right) view] display a tetragonaldisphenoid motif, according to an embodiment of the present invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and detailed description sections, are incorporated by reference as if each had been individually incorporated.

The term "substrate" is intended to have a broad meaning that can include a single layer of a material, multiple layers, laminated layers, composite layers, flexible structures, rigid structures, organic materials, inorganic materials, or combinations thereof. For example, and without limitation, substrates can be glass, plastic, or crystalline materials (e.g., silicon or another semiconductor).

In the present description the term "pi" is sometimes used instead of the Greek letter "n". However, as understood by one of ordinary skill in the art, they are equivalent. For example, "π···π interaction" and "pi-pi interaction" are equivalent. Similarly, "pi-OF" and "πOF" are also equivalent.

Transport along π···π interactions in the 2D in-plane direction, on the other hand, is considered to be a key transport mechanism in organic semiconductors, laying the foundation for remarkable device performance. Therefore, π···π interaction-constructed porous materials with an ordered structure is of special interest. However, due to the inherent features of π···π interaction (weak, flexible and poor directionality), construction of porous material with a permanent porosity is a difficult task, as the structure will most likely easily collapse after solvent removal and decompose upon heating. We are unaware of a previous porous material held together by π···π interactions.

An aspect of the present invention is to provide a molecular structure SFIC The molecular structure SFIC includes a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each fragment unit comprising a 3-(dicyanomethylidene)indan-1-one (IC) unit, each IC unit is used as an end group (EG) to each end of the two spirobifluorene (SF) units. Each IC unit is configured to interact via a pi-pi interaction (π···π interaction) with a neighboring IC unit of an adjacent molecular structure or to interact via a CH-interaction with neighboring aromatic group (R1) of an adjacent molecular structure, or both.

In an embodiment, the biplanar conjugated cruciform-shaped spirobifluorene forms a rigid three-dimensional structure. In an embodiment, each SF unit has a spiro-conjugated structure acting as a tetrahedral node. In an embodiment, the SFIC molecular structure further includes thiophene units provided to increase the pi-conjugated plane of each SF unit. In an embodiment, each IC unit is a chromophore configured to absorb or emit radiation.

In an embodiment, the molecular structure (SFIC) exhibits a tetragonal-disphenoid-shaped molecular conformation and is configured to self-assemble into a 3D porous structure. In an embodiment, the molecular structure (SFIC) has thermal stability after heat treatment. In an embodiment, the molecular structure (SFIC) is recyclable.

In an embodiment, the two SF units forming a rigid biplanar conjugated cruciform-shaped spirobifluorene include:

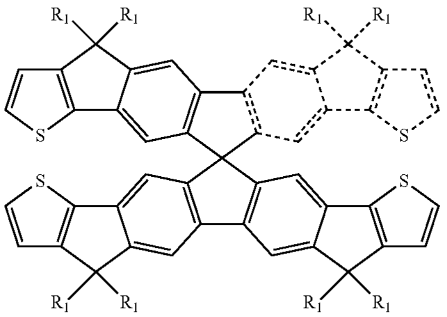

wherein R1 is an aromatic group.

In an embodiment, R1 is selected from the group consisting of:

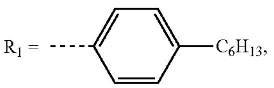

and

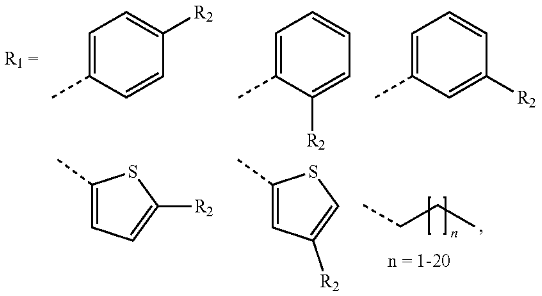

wherein $R_2$ is an alkyl chain.

In an embodiment, the two SF units forming a rigid biplanar conjugated cruciform-shaped spirobifluorene are selected from the group consisting of

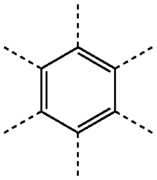

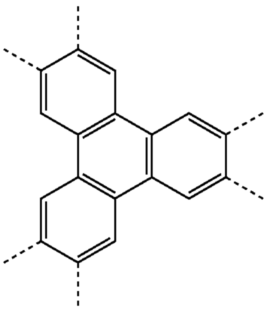

-continued

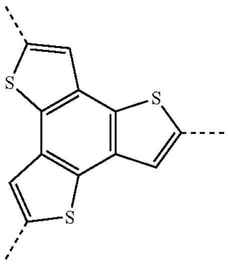

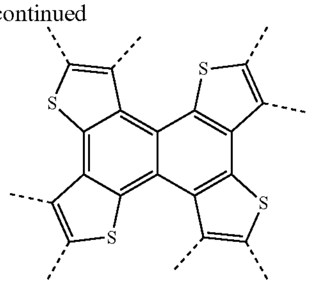

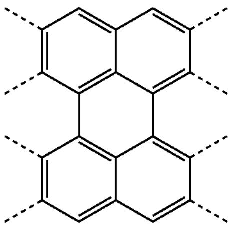

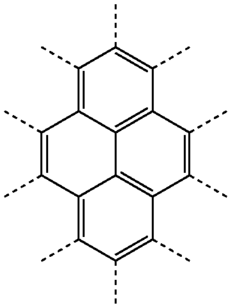

In an embodiment, each IC unit end group (EG) is selected from the group consisting of:

IC

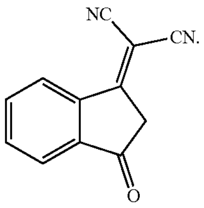

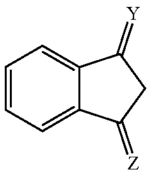

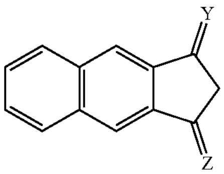

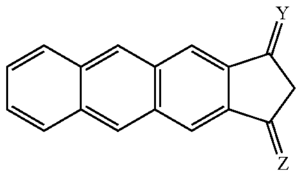

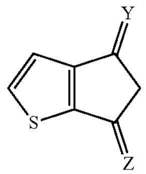

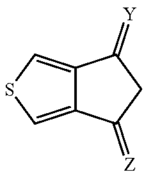

-continued

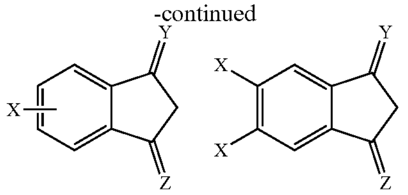

X = Me, F, Cl, Br, I

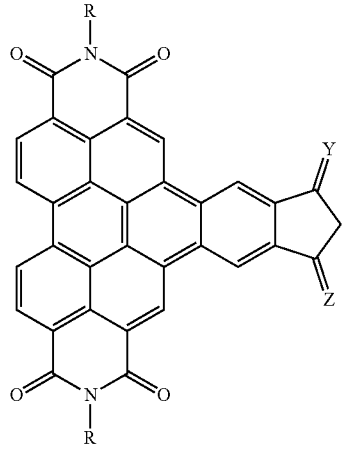

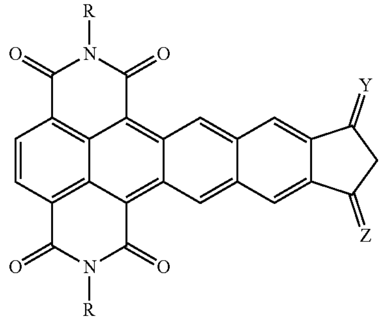

R = Any side chain

Y or Z = O or 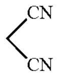 Y and Z could be same or different.

Another aspect of the present invention is to provide a non-covalent pi-pi interaction-constructed organic framework (pi-OF). The non-covalent pi-pi interaction-constructed organic framework (pi-OF) includes a plurality of molecular structures. Each molecular structure includes a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

In an embodiment, the biplanar conjugated cruciform-shaped spirobifluorene forms a rigid three-dimensional structure. In an embodiment, the SF has a spiro-conjugated structure acting as a tetrahedral node. In an embodiment, the non-covalent pi-pi interaction-constructed organic framework (pi-OF) further includes thiophene units to increase the pi-conjugated plane of each SF unit. In an embodiment, each IC unit is a chromophore configured to absorb or emit radiation. In an embodiment, the molecular structure exhibits a tetragonal-disphenoid-shaped molecular conformation and configured to self-assemble into a 3D porous structure. In an embodiment, each molecular structure has thermal stability after heat treatment.

In an embodiment, each molecular structure is connected to four adjacent molecular structures. In an embodiment, the adjacent molecular structures are rotated by 90 degrees relative to the each molecular structure. In an embodiment, each molecular structure is connected to four adjacent molecular structures through four pairs of $\pi\cdots\pi$ interactions through antiparallel EGs.

In an embodiment, the organic framework forms a final three-dimensional lamellar structure. In an embodiment, the non-covalent pi-pi interaction-constructed organic framework (pi-OF) has a plurality of 2D layers, wherein an orientation of molecular structures of adjacent 2D layers are identical and assemble into two repeating layers.

In an embodiment, the pi-OF framework forms a porous 3D structure that is held together by $\pi\cdots\pi$ interactions and further enhanced by intermolecular $CH\cdots\pi$ interactions. In an embodiment, the pi-OF framework can be used in organic field effect transistors (OFET), organic light-emitting diodes (OLED), solar cells or sensors. In an embodiment, the pi-OF can be used as a photoresist in the semiconductor photolithographic process, self-assembly into various shapes or patterns for patterning of metal circuits or semiconductors.

Another aspect of the present invention is to provide a transistor device including a substrate; a plurality of electrodes disposed on the substrate; and a SFIC micro-plate. The SFIC micro-plate has a molecular structure including a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both. The SFIC microplate is disposed on the plurality of electrodes.

In an embodiment, the plurality of electrodes include four electrodes disposed in a quadrangular arrangement, wherein the SFIC microplate is in contact with each of the four electrodes.

A further aspect of the present invention is to provide an organic light emitting device including a substrate electrode; an electron transport layer (ETL) and a hole transport layer (HTL) disposed on the substrate electrode; and a SFIC layer sandwiched between the electron transport layer and the hole transport layer. The SFIC layer has a molecular structure including a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units. Each IC unit is configured to interact via a pi-pi interaction with a neighboring IC unit of an adjacent molecular structure or to interact via a CH-interaction with neighboring aromatic group (R1) of an adjacent molecular structure, or both.

In an embodiment, the substrate includes indium titanium oxide (ITO) glass. In an embodiment, the electron transport layer comprises ZnMgO. The electron transport layer can be deposited on the substrate electrode. In an embodiment, hole transport layer comprises 4,4'-bis(9-carbazolyl) biphenyl (CBP). The hole transport layer can be deposited on the SFIC layer.

In an embodiment, the organic emitting device further includes a second electrode, the second electrode being deposited on the hole transport layer. In an embodiment, the second electrode includes a layer of gold (Au).

In an embodiment, the organic emitting device further includes an intermediate layer disposed between the second electrode and the hole transport layer. In an embodiment, the intermediate layer may include molybdenum oxide ($MoO_3$).

Further Examples: New supermolecular organic porous crystal materials developed by our group.

Figure 1A:
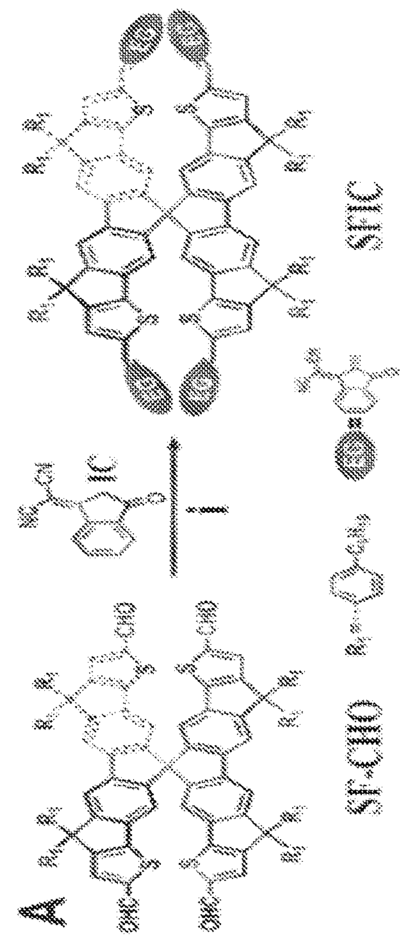
FIG. 1A depicts a synthetic route with reaction conditions of (i) 3-(dicyanomethylidene)indan-1-one (IC, 12 equivalents) and pyridine (1 mL) in chloroform at 70° C. with yield of 90%, according to an embodiment of the present invention.

We reported a novel robust noncovalent π···π-interaction-constructed organic framework, namely πOF, consisting of a permanent 3D porous structure that is held together by noncovalent π···π interactions and further enhanced by intermolecular CH···π interactions (*Proc. Natl. Acad. Sci. USA* (*PNAS*), 2020, 117, 20397-20403; *Adv. Mater.,* 2021, 33, 2006120). In some embodiments, the elaborate porous structure consists of only one type of fully conjugated aromatic tetragonal-disphenoid-shaped molecule with four identical 3-(dicyanomethylidene)indan-1-one planforms. Essentially, our robust noncovalent π···π interaction-stacked organic framework is composed of 3-(dicyanomethylidene)indan-1-one (IC) functional group with directional face-on packing as a multijoint fragment and spirobifluorene (SF) as the centroid core (FIG. 1A). Based on the fused-ring strategy, the thiophene units with lower resonance energy were introduced in the orthogonal direction of the spirofluorene centroid core to expand the π plane for stable intermolecular π···π interactions.

Figure 1C:
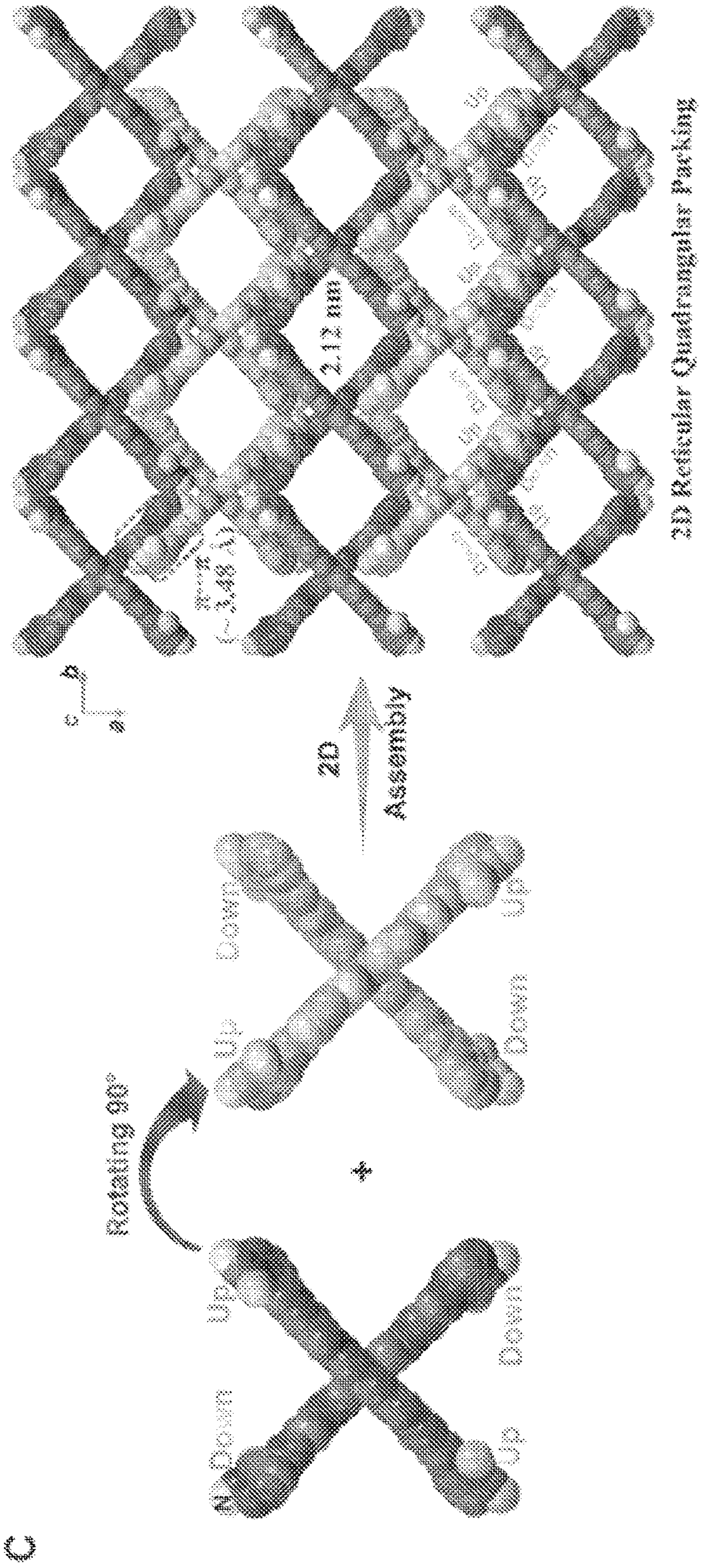
FIG. 1C shows the two-dimensional (2D) crystal assembly along the ac plane via π···π interactions, according to an embodiment of the present invention.
Figure 1D:
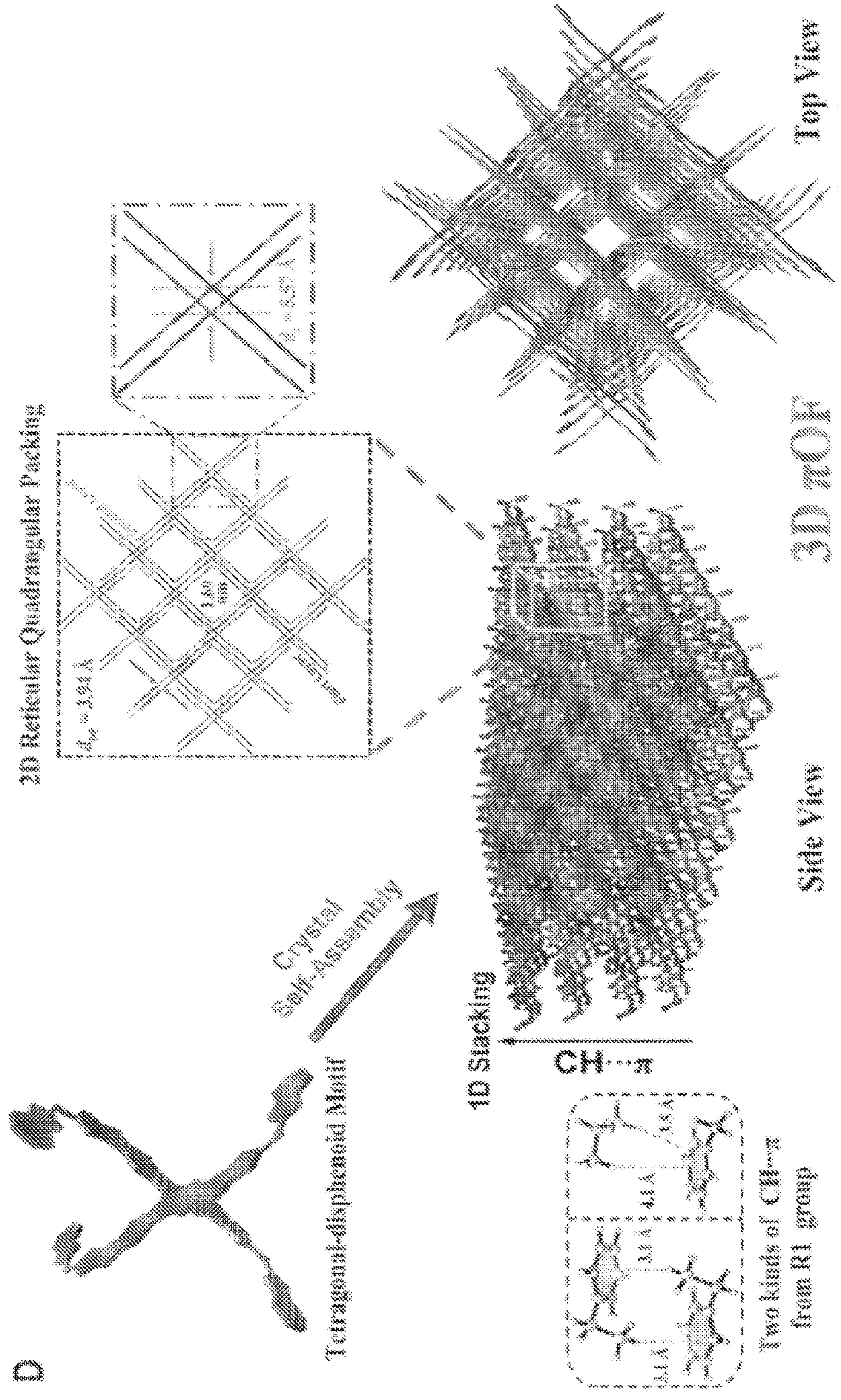
FIG. 1D depicts a molecular packing arrangement of the three-dimensional (3D) πOF structure is composed of 2D π···π (ac plane) interactions and one dimensional (1D) CH···π (b axis) interactions, according to an embodiment of the present invention.

3D structural characterizations: XRD analysis of single crystals indicated that the dimensions of SFIC conformers are ~21.92 Å in length, ~19.13 Å in width, and ~14.28 Å in height (FIG. 1B). Each crisscrossed SFIC molecule is connected to four adjacent SFIC molecules through four pairs of π···π interactions between IC units (FIG. 1C). Such packing assembles into a 2D porous framework, forming a final 3D lamellar structure through CH···π interactions of hexylbenzene side chains. The conformation of SFIC molecules between adjacent layers are identical so the 2D layers can assemble into ordered 3D frameworks. Between the repeated two layers, there will be a unidirectional slippage (between two parallel wings, $d_{sp}$) and bidirectional slippage (between two central carbon atoms, $d_8$) (FIG. 1D). Four SFIC molecules of each layer form a dimetric micropore, which has a diameter of 2.12 nm across the layer and a lower diameter of 1.69 nm between two layers due to the slippage of adjacent layers.

FIGS. 1A-1D show the molecular configuration and supramolecular crystal assembly based on SF as the centroid core and IC as the multijoint fragments, according to an embodiment of the present invention. FIG. 1A depicts a synthetic route with reaction conditions of (i) 3-(dicyanomethylidene)indan-1-one (IC, 12 equivalents) and pyridine (1 mL) in chloroform at 70° C. with yield of 90%, according to an embodiment of the present invention. FIG. 1B shows the single-crystal X-ray molecular structure [top (Left) and side (Right) view] display a tetragonaldisphenoid motif, according to an embodiment of the present invention. FIG. 1C shows the 2D crystal assembly along the ac plane via π···π interactions, according to an embodiment of the present invention. The directions of up and down refer to the direction of the N atom. FIG. 1D depicts a molecular packing arrangement of the 3D πOF structure is composed of 2D π···π (ac plane) interactions and 1D CH···π (b axis) interactions, according to an embodiment of the present invention. $d_{DP}$ and $d_s$ stand for packing and slippage distances between layers, respectively. The alkyl chains, hydrogen and oxygen atoms, and cyano groups are omitted for clarity.

Figure 8:
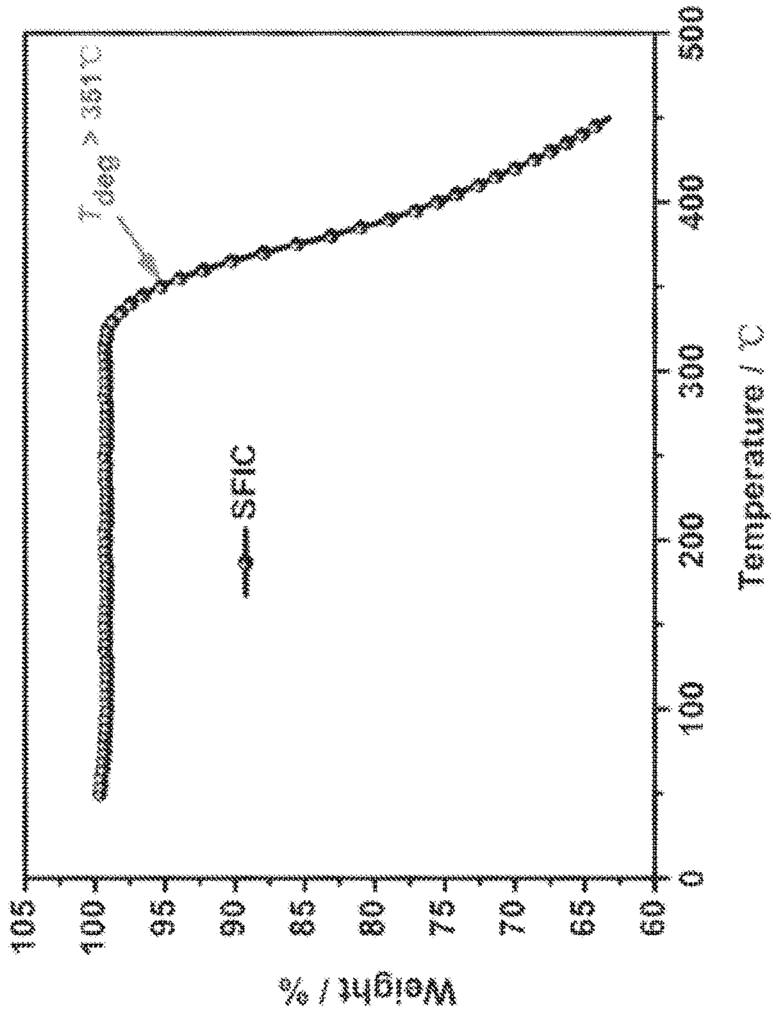
FIG. 8 shows a plot of weight in percent versus temperature (thermogravimetric or TGA curve) of SFIC under nitrogen flow, according to an embodiment of the present invention.

In an embodiment, a target product SFIC was obtained via Knoevenagel condensation between SF—CHO and 3-(dicyanomethylidene)indan-1-one (IC) in 90% yield (FIG. 1A). The structure was confirmed by 1HNMR, $^{13}C$ NMR and high-resolution mass spectrometry (see SI). SFIC is soluble in common organic solvents such as dichloromethane, chloroform, chlorobenzene and ortho-dichlorobenzene (o-DCB) at room temperature due to the cross-linked molecular scaffold and the branched alkyl chains. The thermal properties were evaluated by thermal gravimetric analysis (TGA) performed under nitrogen. SFIC showed high thermal stability with 5% weight loss at decomposition temperature of over 351° C. (FIG. 8). The molecular conformation of SFIC, which is a tetragonaldisphenoid shape, was confirmed by X-ray diffraction analysis of single crystals obtained by slow vapor diffusion (CHCl3/MeOH). The dimensions of SFIC conformer are ~21.92 Å in length, ~19.13 Å in width and ~14.28 Å in height (FIG. 1B). Two IC groups on the same wing are non-coplanar with a dihedral angle of 28.07°. Each crisscrossed SFIC molecule is connected to four adjacent SFIC molecules (which are rotated 900 relative to the centroid molecule) through four pairs of π···π interactions through antiparallel EGs (FIG. 1C). Such packing forms a 2D reticular quadrangular arrays which undergo perpendicular slipped 1D stacking through two different types of CH···π interactions (FIG. 1D and FIG. 10) of hexylbenzene side chains forming a final three-dimensional (3D) lamellar structure. We confirmed that the orientation of SFIC molecules of adjacent 2D layers are identical and assemble into two repeating layers with a 3.94 Å-long unidirectional slippage (between two parallel wings, $d_{sp}$) and 5.57 Å-long bidirectional slippage (between two central carbon atoms, $d_s$) (FIG. 1D). Closer investigation of the structure reveals that four discrete SFIC molecules of each layer form a dimetric micropore, which has a diameter of 2.12 nm (FIG. 1C) across the layer and a lower diameter of 1.69 nm (FIG. 1D) between two layers due to the slippage of adjacent layers.

Figure 2A:
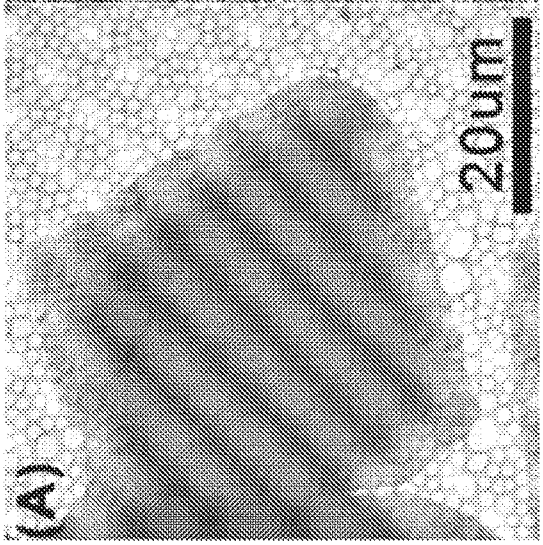
FIG. 2A depicts a transmission electron microscope (TEM) image of % OFs, according to an embodiment of the present invention.
Figure 2B:
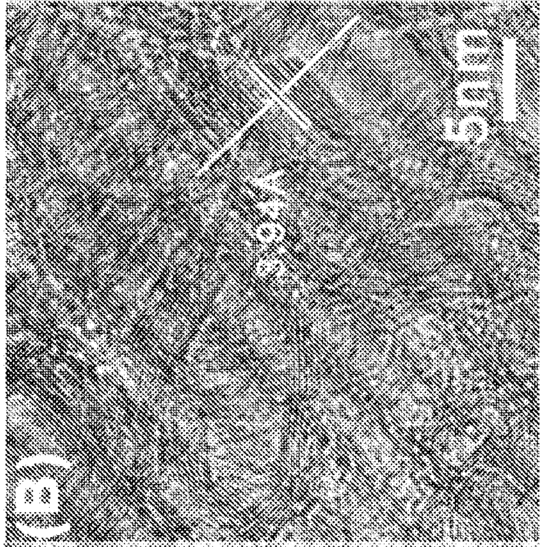
FIG. 2B shows a high resolution transmission electron microscope (HRTEM) image of SFIC πOF, according to an embodiment of the present invention.
Figure 2C:
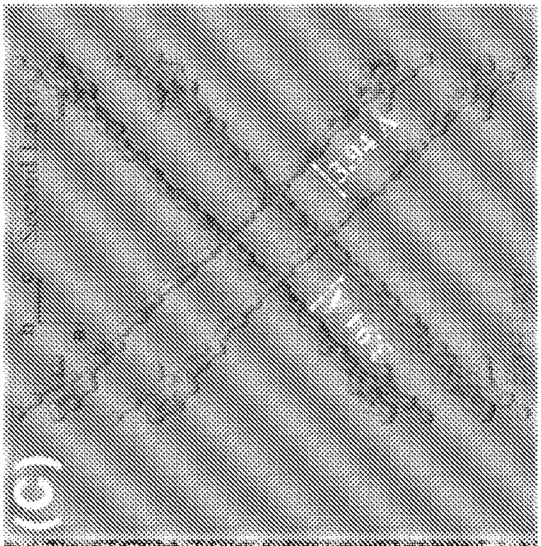
FIG. 2C shows a molecular crystal packing model of πOF, according to an embodiment of the present invention.
Figure 2D:
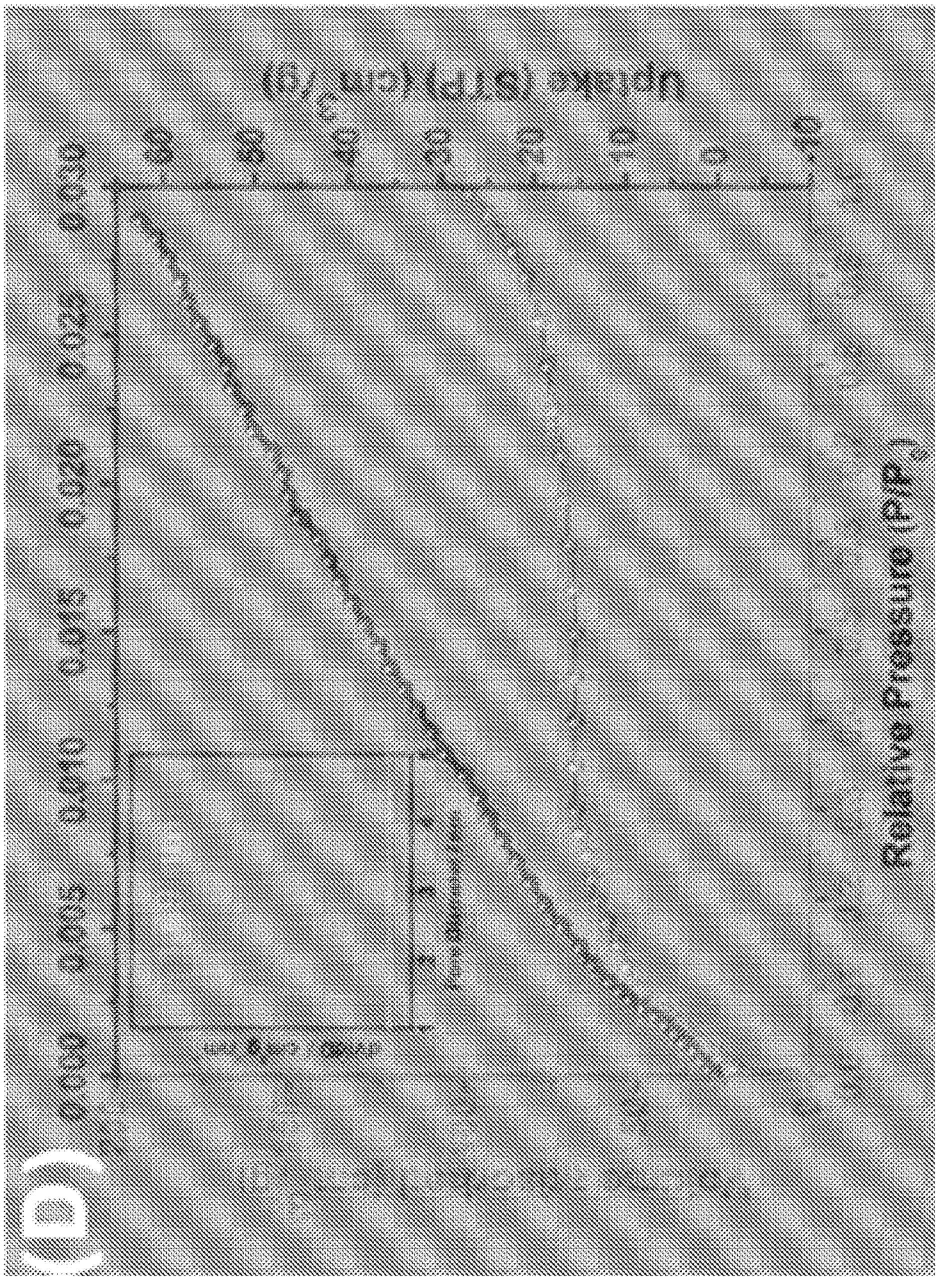
FIG. 2D shows a $CO_2$ (blue line) and $N_2$ (red line) adsorption isotherms of πOF, according to an embodiment of the present invention.
Figure 2E:
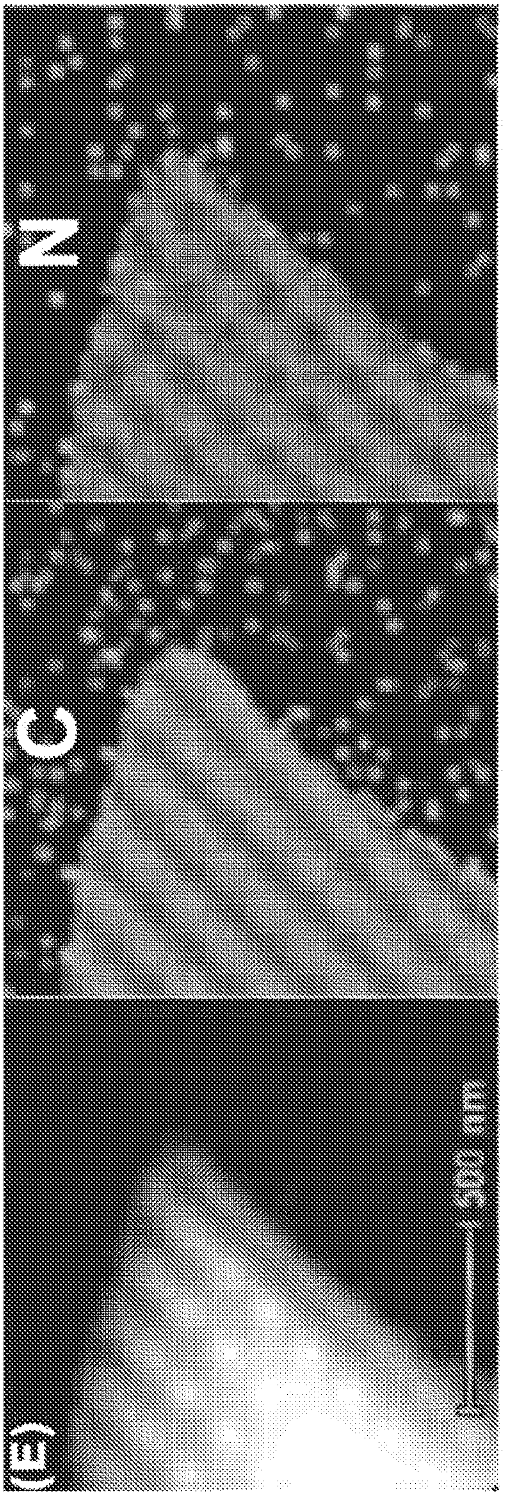
FIG. 2E shows EDS element mappings of πOFs, according to an embodiment of the present invention.
Figure 2F:
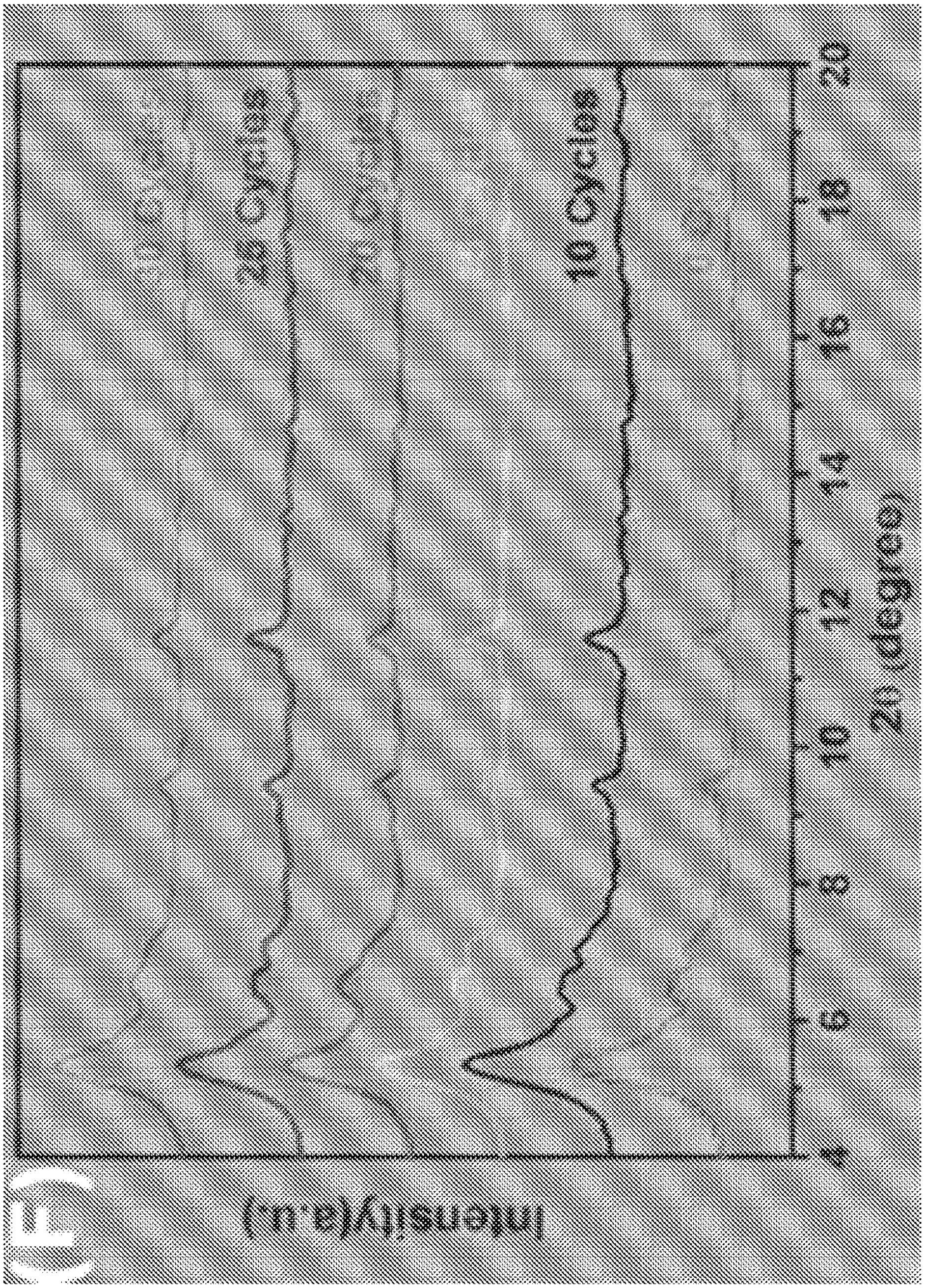
FIG. 2F depicts a recyclability test of $N_2$ adsorption desorption experiments of πOF, according to an embodiment of the present invention.
Figure 2G:
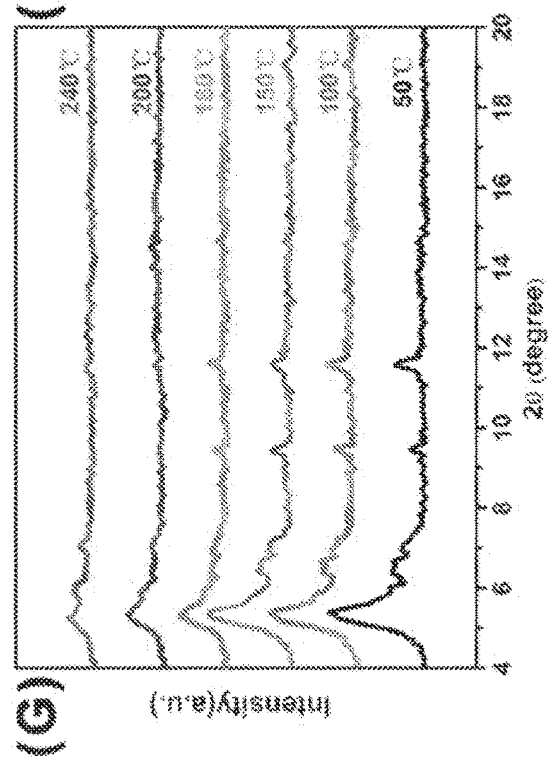
FIG. 2G depicts a variable-temperature powder X-ray diffraction (PXRD) patterns of πOF, according to an embodiment of the present invention.

FIGS. 2A-2I show the morphology and sorption characterizations of πOFs, according to an embodiment of the present invention. FIG. 2A depicts a transmission electron microscope (TEM) image of πOFs, according to an embodiment of the present invention. FIG. 2B shows a HRTEM image of SFIC πOF, according to an embodiment of the present invention. FIG. 2C shows a molecular crystal packing model of XOF, according to an embodiment of the present invention. FIG. 2D shows a $CO_2$ (blue line) and $N_2$ (red line) adsorption isotherms of πOF, according to an embodiment of the present invention. The inset is the pore size distribution analysis based on the BJH method. FIG. 2E shows EDS element mappings of πOFs, according to an embodiment of the present invention. FIG. 2F depicts a recyclability test of $N_2$ adsorption desorption experiments of πOF, according to an embodiment of the present invention. FIG. 2G depicts a variable-temperature PXRD patterns of πOF, according to an embodiment of the present invention.

Figure 2H:
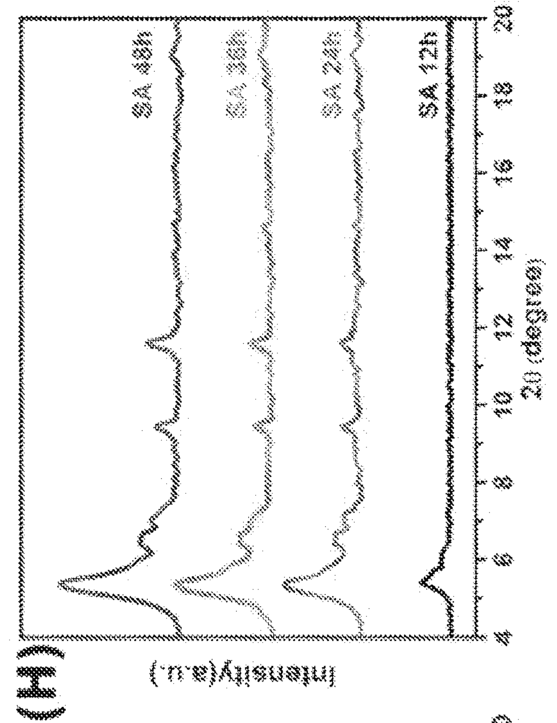
FIG. 2H shows a time dependent powder X-ray diffraction (PXRD) patterns of πOF (post heat-treatment at 240° C.) processed by solvent annealing (methanol/chloroform), according to an embodiment of the present invention.
Figure 2I:
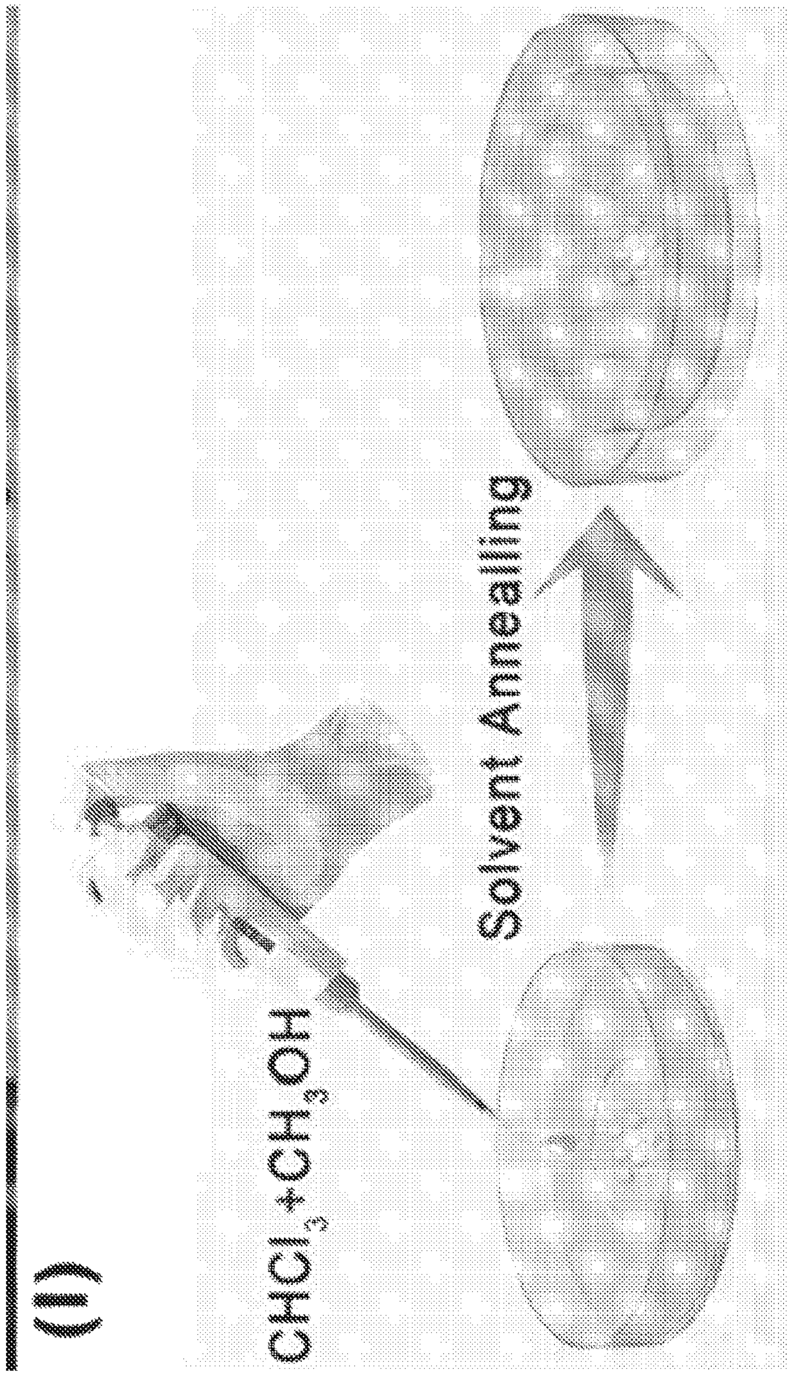
FIG. 2I shows the procedure of solvent annealing using methanol/chloroform, according to an embodiment of the present invention.

FIG. 2H shows a time dependent PXRD patterns of πOF (post heat-treatment at 240° C.) processed by (I) solvent annealing (methanol/chloroform), according to an embodiment of the present invention. The rhomboid-shaped morphology of πOF with diagonal lengths of 50.5 m and 59.5 μm was observed using TEM (FIG. 2A), with the thickness thinning towards the edges of the crystal. The obvious crystal lattice fringes of πOF can be observed in high-resolution TEM (HRTEM) image (FIG. 2B), demonstrating the high crystallinity of the prepared ROF. The lattice fringe was measured to be about 3.94 Å, which is identical to the unidirectional slippage distance between the two parallel wings of two SFIC molecules from adjacent layers (FIG. 2C). As shown in FIG. 2D, the as-prepared πOF exhibited high $CO_2$ uptake capacity of 62.41 cm3·g−1 (blue line) due to rich porous structure. Furthermore, the powdery sample of guest-free πOF presented a typical type I sorption isotherm for $N_2$ bearing a steep slope in the high relative pressure ($P/P_0$) range for microporous structure within the 1-2 nm range. The microporous structure was further confirmed using the t-plot analysis shown in FIG. 11. The corresponding Brunauer-Emmett-Teller (BET) surface area was over 248.92 m2·g−1 (red circles in FIG. 2D) and pore volume of 0.41 cm3·g−1. The pore size distribution of πOFs based on the Barret-Joyner-Halenda (BJH) model showed a single peak at 1.69 nm (see, inset in FIG. 2D), which is consistent with the uniform dimetric pores of crystal packing structure. The elemental mapping images (FIG. 2E) displayed a highly uniform dispersion of C and N elements throughout the entire πOF. Porous material with super-microporous range of 1-2 nm shown in this work is a significant achievement that will bridge the gap between mesoporous materials and microporous zeolites. The porous crystals after activation, particularly when guest-free, are less stable than other porous materials that are linked by dynamic covalent bonds or metal coordination bonds, while some hydrogen-bonded porous crystals (HOF) are able to keep the original crystal framework after the removal of guest molecules. Few of the non-classical hydrogen-bond-constructed (C—H···X) porous crystals could survive beyond 130° C. (27-28). Compared to conventional hydrogen bonds, and even the non-classical ones, π···π interactions are far more labile. Surprisingly, our more labile πOF based on SFIC is significantly more thermally robust than the reported hydrogen-bonded ones, showing no change up to 180° C. in variable-temperature powder XRD (PXRD) patterns (FIG. 2G). The structure remained identical to that of the simulated one from the single-crystal structure, with peaks at 2θ=5.3°, 9.2° and 11.50 assigned to (020), (031) and (400) lattice planes. Further heating up to 200° C. and 240° C., the PXRD patterns changed suddenly, indicating a transition into a different crystalline phase.

Self-healing materials have received tremendous attention recently. However, in the case of solid materials, presence of notable healing properties often results in low thermostability. SFIC πOF, on the contrary, showed excellent thermal stability with decomposition temperature of over 351° C. with a 5% weight loss. After heat-treatment at 240° C., 7° F. self-healed retrieving its parent porosity upon solvent annealing (methanol/chloroform vapor) at room temperature (FIG. 2I), and the original diffraction peaks were completely recovered 24 h after solvent annealing and the intensity gradually increased with time (FIG. 2H). FIG. 21 shows a procedure of solvent annealing using methanol/chloroform, according to an embodiment of the present invention. Meanwhile, we also tested the reusability of πOF with $N_2$ adsorption-desorption measurements. After every 5 cycles of $N_2$ adsorption desorption experiment, the PXRD of πOF was measured to examine the change in the original framework structure. πOF retained its original crystalline structure and skeleton even after 30 cycles, as it can be seen from the unaltered positions and strength of peaks in PXRD profiles (FIG. 2F). These results suggest that πOF is of admirable stability and is highly reusable, suggesting noteworthy self-healing ability.

Figure 3A:
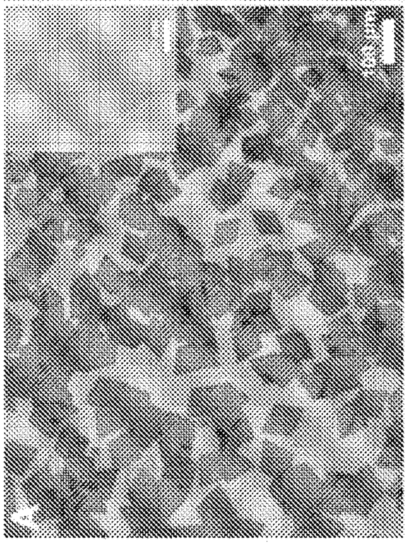
FIG. 3A is an optical microscopy (OM) image of SFIC micro-plates (drop-casted in CHCl3 (1 mg/mL)) self-assembled on an OTS treated SiO2/Si substrate at room temperature, according to an embodiment of the present invention.
Figure 3B:
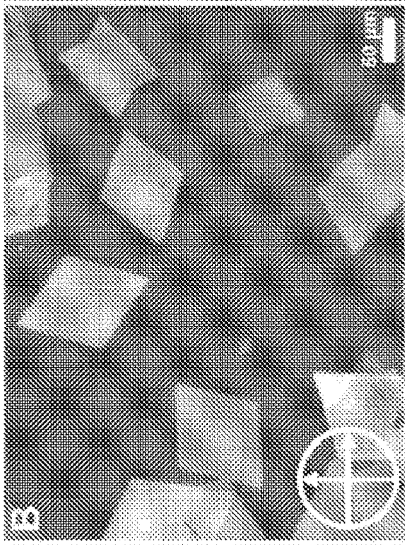
FIGS. 3B and 3C are cross-polarized optical microscopy (CPOM) images of the single-crystal micro-plates of SFIC, according to an embodiment of the present invention.
Figure 3C:
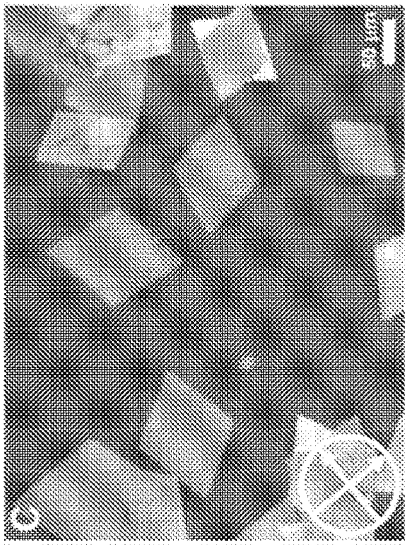
Figure 3D:
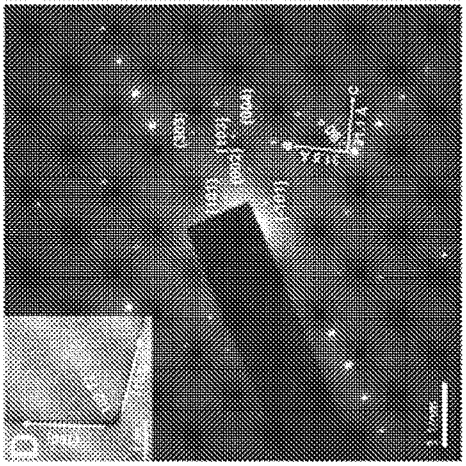
FIG. 3D is a TEM image and its corresponding selected area diffraction (SAED) patterns, according to an embodiment of the present invention.
Figure 3E:
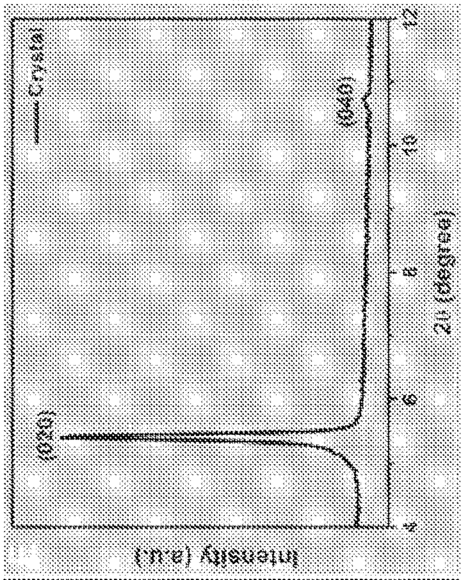
FIG. 3E is a one-dimensional (1D) out-of-plane X-ray diffraction (XRD) pattern of a single crystal data, according to an embodiment of the present invention.
Figure 3F:
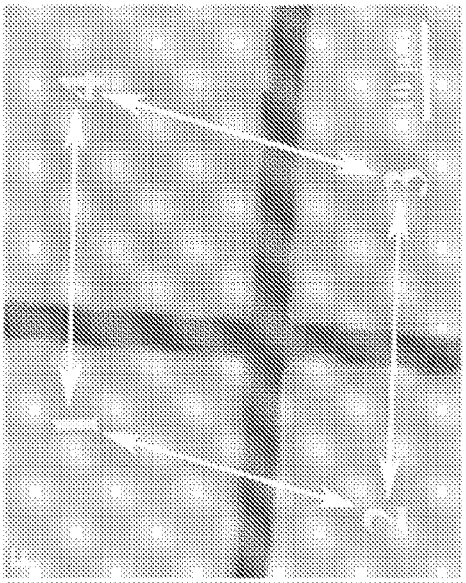
FIG. 3F is a transistor with four electrodes probing charge transport properties along different crystal planes, according to an embodiment of the present invention.
Figure 3G:
FIG. 3G is a schematic diagram of SFIC micro-/nano-crystal transistor, according to an embodiment of the present invention.
Figure 3H:
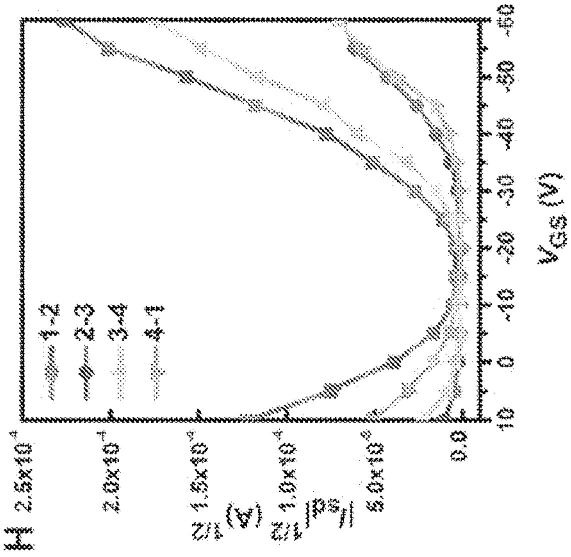
FIG. 3H is a plot of current to voltage for a P-type transistor, according to an embodiment of the present invention.
Figure 3I:
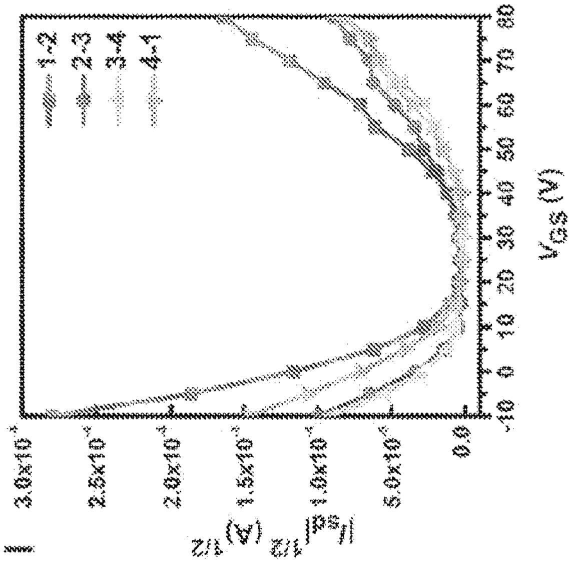
FIG. 3I is a plot of current to voltage for a N-type transistor, according to an embodiment of the present invention.

FIGS. 3A-3I show Single-crystal transistor (OFET) characterization of SFIC, according to an embodiment of the present invention. FIG. 3A is an optical microscopy (OM) image of SFIC micro-plates (drop-casted in $CHCl_3$ (1 mg/mL)) self-assembled on an OTS treated $SiO_2$/Si substrate at room temperature, according to an embodiment of the present invention. FIGS. 3B and 3C are cross-polarized optical microscopy (CPOM) images of the single-crystal micro-plates of SFIC, according to an embodiment of the present invention. FIG. 3D is a TEM image and its corresponding SAED patterns, according to an embodiment of the present invention. FIG. 3E is a 1D out-of-plane XRD pattern of a single crystal data, according to an embodiment of the present invention. FIG. 3F is a transistor with four electrodes probing charge transport properties along different crystal planes, according to an embodiment of the present invention. FIG. 3G is a schematic diagram of SFIC micro-/nano-crystal transistor, according to an embodiment of the present invention. FIG. 3H is a plot of current to voltage for a P-type transistor, according to an embodiment of the present invention. FIG. 31 is a plot of current to voltage for a N-type transistor, according to an embodiment of the present invention.

To evaluate the intrinsic charge transport properties of πOF, the single-crystal micro-plates of SFIC were prepared by a typical drop-casting method in CHCl3 solution onto the noctadecyltrichlorosilane (OTS) modified SiO2/Si substrates. Optical microscope (OM) images and bright-field TEM images (top-left inset) of the SFIC micro-plates with a rhomboid shape and long-range regularity are presented in FIGS. 3A and 3D. The change in crystal intensities in the cross polarized optical microscopy (CPOM) images indicate the single crystal nature of the micro-plates (FIGS. 3B and 3C). The out-of-plane XRD with strong and sharp multiple Bragg diffractions in FIG. 3E indicate high degree of crystalline structures and highly ordered lamellar structure of SFIC micro-plates. Two strong diffraction peaks at 2θ=5.410 and 10.74° are observed in the XRD analysis for the micro-plates (FIG. 3E), which could be assigned to (020) and (040) lattice plane, respectively, based on the data from the single-crystal structure. The corresponding selected area electron diffraction (SAED) patterns (FIG. 3D) of SFIC micro-plates showed the ordered and bright diffractions at different locations, indicating the single-crystal nature of the micro-plates. The SAED diffraction patterns of SFIC are equal to a repeating period of 31.5 Å along one side of a rhomboid micro-plate direction and a repeating period of 21.1 Å along the other side of a rhomboid micro-plate, which can be assigned to the [100] and [103] directions based on prior single-crystal X-ray analysis. Besides, according to the law of consistency of interfacial angles: the measured interfacial angles of [100] direction and [103] direction from the images was 102.72°, which was equal to the calculated interfacial angles according to the single-crystal structure. The out-of-plane XRD data together with SAED pattern and single-crystal XRD data reveal that the SFIC micro-plates are of the same phase as in the previously obtained single crystals. The field effect transistor devices based on the rhomboid micro-crystal of SFIC-πOF were fabricated by an "organic ribbon mask" technique with four electrodes and channels to explore the directional charge transport properties (FIG. 3F). The transfer characteristics of four different crystal planes tested under ambient conditions are shown in FIG. 3H and FIG. 31, and the mobility data is summarized in Table S2. The OFET device based on SFIC micro-plates show ambipolar characteristics, a concurrent existence of both hole (FIG. 3H) and electron (FIG. 3I) charge-carrier transport behavior. The same directional conducting channels, 1↔2 and 3↔4 or 2↔3 and 4↔1, show similar mobilities (cm2 V−1 s−1) (μh(1−2)=2.28×10−3, μe(1-2)=6.92×10−4, μh(3-4)=1.13×10−3, μe(3−4)=2.02×10−4, or μh(2−3)=5.43×10−4, μe(2−3)=1.29×10−4, μh(4−1)=3.17×10−4, μh(4−1)=1.69×10−4) (Table. S2). And the channels of 1↔2 and 3↔4 show higher mobility than the 2↔3 and 4↔1 channels, especially for hole mobility (about one order of magnitude higher). These results imply that the reticular quadrangular lattice of SFIC-πOF possesses anisotropic properties, which are further studied using density functional theory (DFT) calculations.

Figures 4A, 4B, 4C, 4D, 4E:
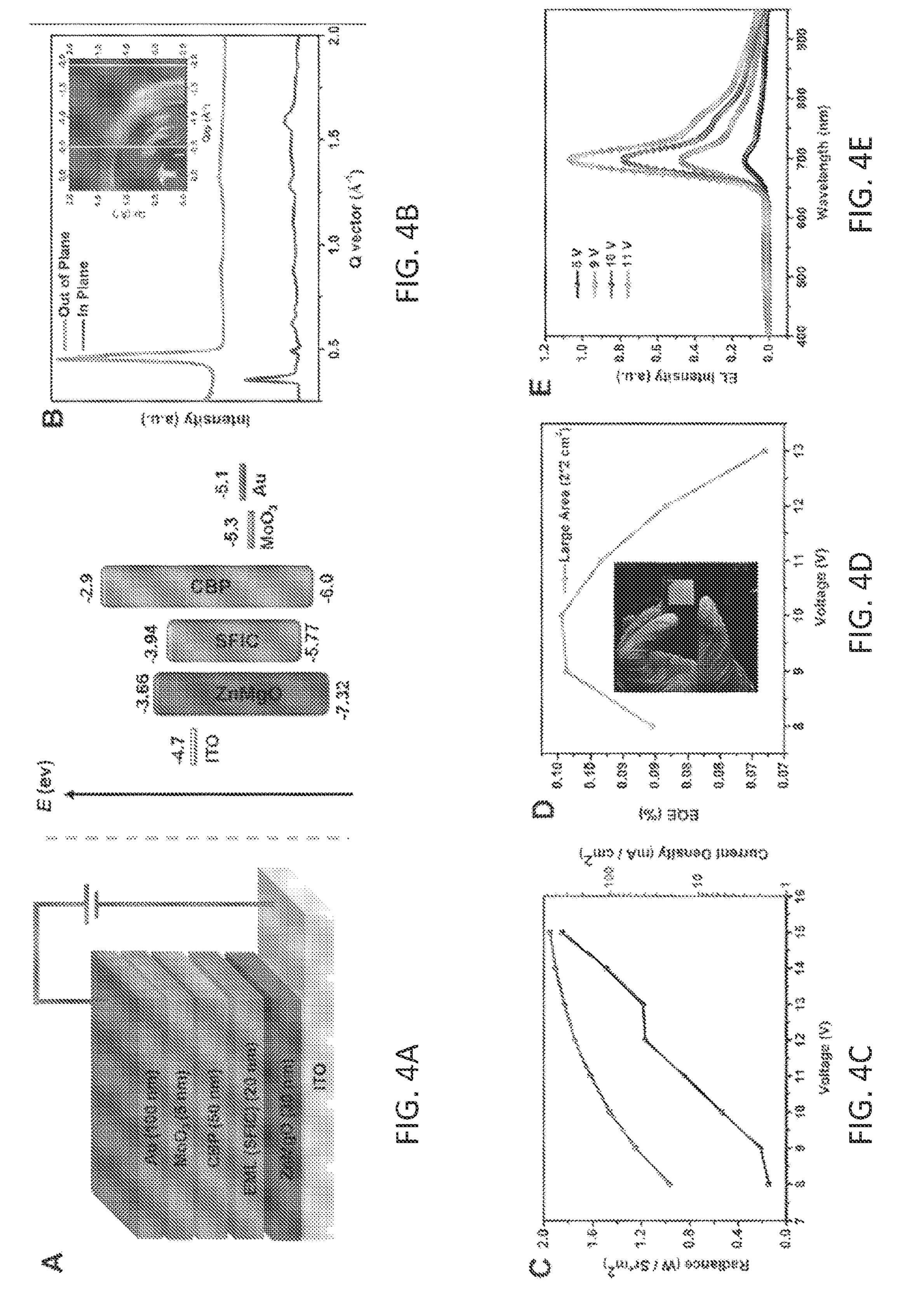
FIG. 4A is a schematic device structure and energy level diagram, according to an embodiment of the present invention.
FIG. 4B is a radially-integrated intensity plot of out of plane and in plane 1D Grazing-Incidence Wide-Angle X-ray Scattering (GIWAXS) pattern of SFIC film (the inset is two-dimensional (2D) GIWAXS pattern of SFIC film, according to an embodiment of the present invention.
FIG. 4C is a radiance and current density, according to an embodiment of the present invention.
FIG. 4D is a external quantum efficiency (EQE) as a function of applied voltage with a large emitting area of 2×2 cm2, according to an embodiment of the present invention.
FIG. 4E shows voltage-dependent electroluminescence (EL) spectra with a large emitting area of 2×2 cm2, according to an embodiment of the present invention.

FIGS. 4A-4E SFIC emitter-based organic light-emitting diode (OLED) characterization, according to an embodiment of the present invention. FIG. 4A is a schematic device structure and energy level diagram, according to an embodiment of the present invention. FIG. 4B is a radially-integrated intensity plot of out of plane and in plane 1D Grazing-Incidence Wide-Angle X-ray Scattering (GIWAXS) pattern of SFIC film (the inset is 2D GIWAXS pattern of SFIC film, according to an embodiment of the present invention. FIG. 4C is a radiance and current density, according to an embodiment of the present invention. FIG. 4D is a EQE as a function of applied voltage with a large emitting area of 2×2 cm2, according to an embodiment of the present invention. The inset in FIG. 4D is a photo image of a working SFIC emitter-based OLED, according to an embodiment of the present invention. FIG. 4E is a Voltage-dependent EL spectra with a large emitting area of 2×2 cm2, according to an embodiment of the present invention.

To elucidate the correlation between single crystal and the packing orientation of the film, the single crystal data and the two-dimensional grazing incidence wide-angle X-ray scattering (2DGIWAXS) analysis are compared in FIG. 4B. In the corresponding 1D GIWAXS profile in out of plane line cut (FIG. 4B), there are three main diffraction spots at Qz=0.42−1.38 Å−1, which are identified as (020), (040) and (060) lattice plane orientations based on the crystal data. These out of plane signals indicate that SFIC self-organizes into a lamellar structure perpendicular to the substrate along b axis, which is in agreement with the crystal packing model along the b axis. In addition, from the in-plane direction, there is one major arc shape signal peak with a Q value of 1.55-1.65 Å-1 (FIG. 4B and inset), which indicates the existence of a distinct π···π stacking along the ac plane parallel to the substrate. This is consistent with the 2D packing model of crystal via π···π interaction along the ac plane. The GIWAXS analysis reflected the assembly structure of SFIC film, which matches well the single crystal data. Solution-processed SFIC formed a uniform_film offering the potential for large-area application in photoelectronics.

Figure 12A:
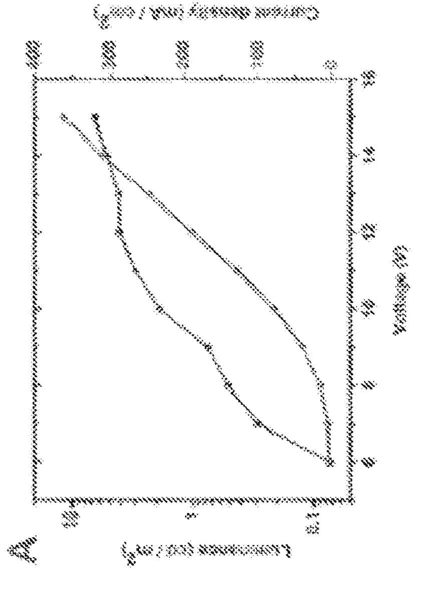
FIG. 12A shows the radiance and current density as a function of applied voltage in SFIC emitter-based OLED, according to an embodiment of the present invention.
Figure 12B:
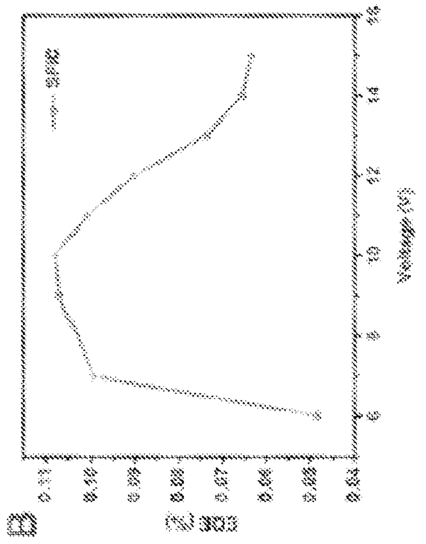
FIG. 12B shows EQE as a function of applied voltage in SFIC emitter-based OLED, according to an embodiment of the present invention.
Figure 12C:
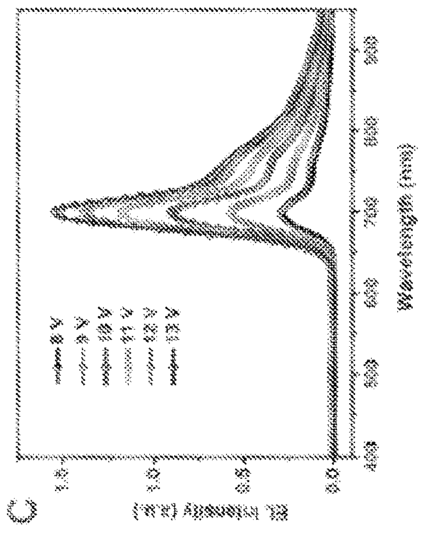
FIG. 12C shows voltage-dependent EL spectra of SFIC emitter based OLED, according to an embodiment of the present invention.

We also were able to fabricate OLEDs with SFIC used as an emitter as shown in FIG. 4A, where ZnMgO and 4,4'-bis(9-carbazolyl) biphenyl (CBP) were used as electron-transporting layer an hole-transporting layer, respectively. Corresponding energy alignment is presented on the right side of FIG. 3A. The current density and radiance rose rapidly after turning on the device (FIG. 4C), implying efficient charge injection and transport in the device. The external quantum efficiency (EQE) of the OLED reached 0.1% at 10 V with a current density of 80 mA cm−2 (FIGS. 4D and 4C) on a large-area device 2×2 cm2, which is close to the EQE of 0.11% achieved from a small area device (FIGS. 12A and 12B). Inset of FIG. 4D is a photo image of the working OLED with an emitting area of 2×2 cm2. The excellent emitting homogeneity indicates the merits of film forming ability of SFIC on a large scale. The bias voltage dependent EL spectra of large-area device are shown in FIG. 4E, where EL emission profile was kept constant under various bias voltages ranging from 8 V to 11 V with main peaks at 700 nm (belonging to the near-infrared). Similar results were observed with a small device (FIG. 12C). The full width at half maximum (FWHM) were about 37 nm suggesting that SFIC is a promising candidate for crimson emission.

Figure 5A:
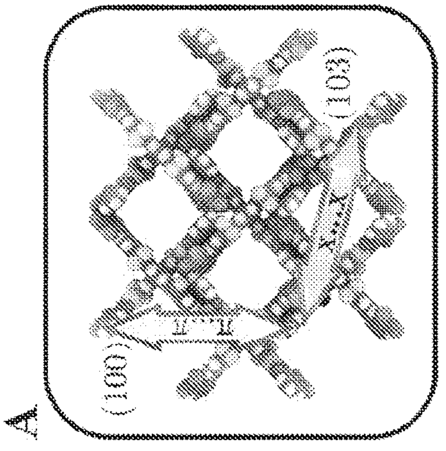
FIG. 5A shows a crystal packing, green spheres represent alkyl-chains, according to an embodiment of the present invention.
Figure 5B:
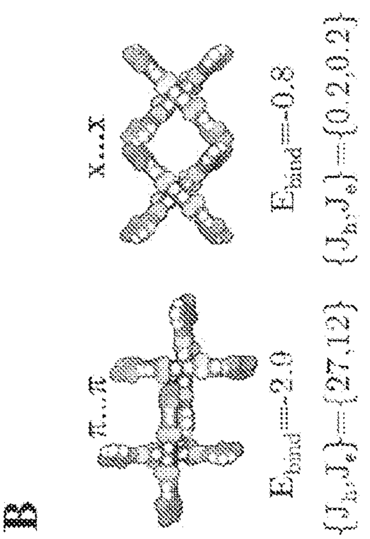
FIG. 5B show calculated binding energies (in eV units), hole transfer (Je) and electron transfer integrals (Je) (in meV units), according to an embodiment of the present invention.
Figure 5C:
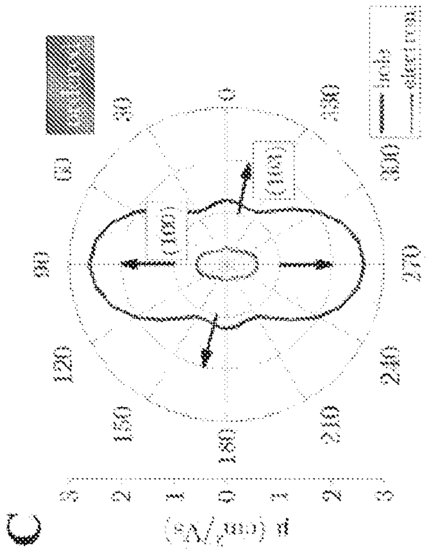
FIG. 5C is an angular plot showing direction-resolved hole and electron mobilities in ordered phase, according to an embodiment of the present invention.
Figure 5D:
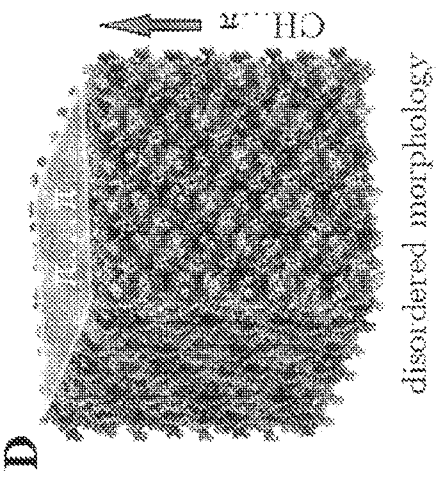
FIG. 5D shows atomistic morphology of the disordered phase, according to an embodiment of the present invention.
Figure 5E:
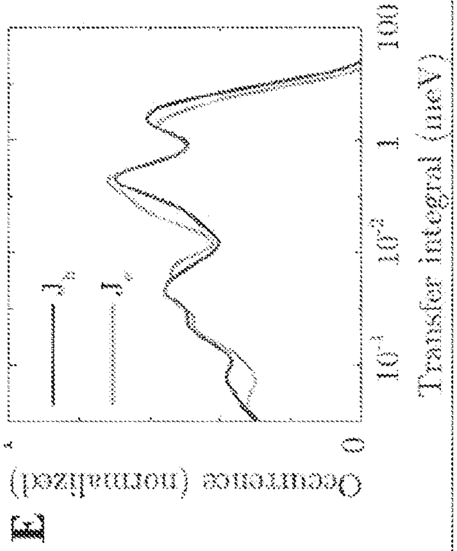
FIG. 5E shows hole and electron transfer integral distributions in all transport directions, according to an embodiment of the present invention.
Figure 5F:
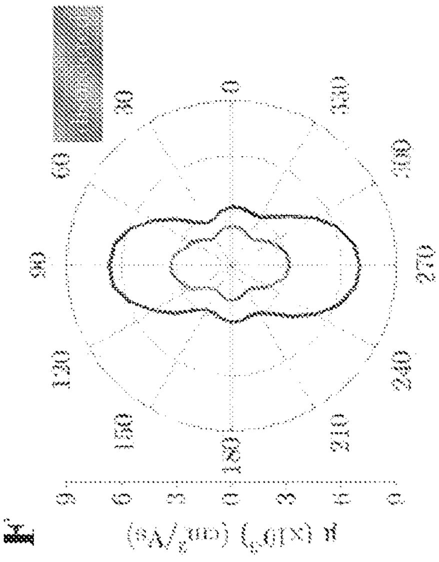
FIG. 5F is an angular plot showing direction-resolved hole and electron mobilities in disordered phase, according to an embodiment of the present invention.

FIGS. 5A-5F depicts a computational characterization of hole/electron transport, according to an embodiment of the present invention. FIG. 5A shows a crystal packing, green spheres represent alkyl-chains, according to an embodiment of the present invention. FIG. 5B show calculated binding energies (in eV units), hole transfer (Je) and electron transfer integrals (Je) (in meV units), according to an embodiment of the present invention. FIG. 5C is an angular plot showing direction-resolved hole and electron mobilities in ordered phase, according to an embodiment of the present invention. FIG. 5D shows atomistic morphology of the disordered phase, according to an embodiment of the present invention. FIG. 5E shows hole and electron transfer integral distributions in all transport directions, according to an embodiment of the present invention. FIG. 5F is an angular plot showing direction-resolved hole and electron mobilities in disordered phase, according to an embodiment of the present invention.

Figure 14B:
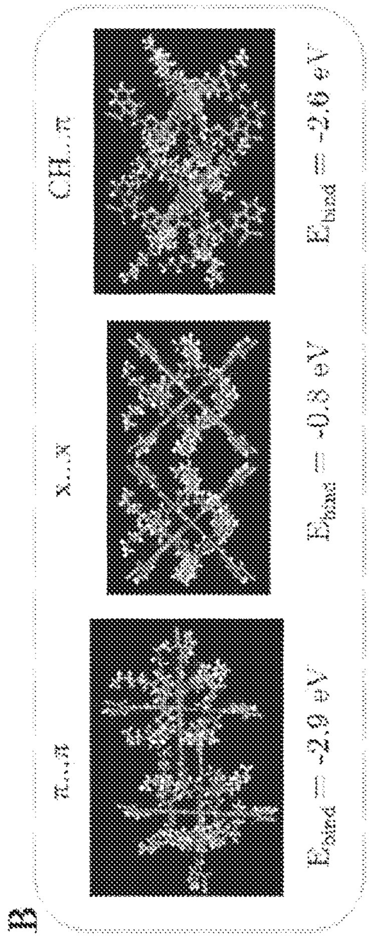
FIG. 14B shows three possible SFIC pair interactions present in the crystal and the corresponding B97D/6-31G (d,p)-calculated dimer binding energies, according to an embodiment of the present invention.

We performed extensive theoretical calculations for the computational characterization of hole/electron transport in SFIC. To be parallel to FIG. 3A-3I, we first focused on the packing along (100) and (103) planes, which rendered the π···π and π···π interactions, respectively (FIGS. 5A and 5B). First principles calculations (FIGS. 14A-14F) revealed that the dimer binding energies and transfer integrals of π···π interactions are found to be considerably larger than those of x···x, due to relatively strong π···π binding. In the SFIC crystal, hole transfer integral (Jh) of π···π are more than a factor of two stronger than electron transfer integral (Je), whereas they are the same in x···x. The intramolecular reorganization energies of hole (Δh) and electron (Δe) transfer are found to be the same (Δh=λe=82 meV) (see also FIG. 14B). Transport calculations put forth that, charge-carrier mobilities on the order of 1−3 cm2/Vs can be achieved for a defect-free SFIC crystal. In addition, (i) μh>μe over the π···π plane independent of the transport direction, attributed to Jh>Je along π···π and (ii) mobility along (100) is larger than (103) for both hole and electron mobilities, since transfer integrals along π···π are considerably larger than those of x···x (e.g., 27 meV vs. 0.2 meV) (see, also FIG. 14C). (i) and (ii) are both consistent with the OFET results in FIGS. 3A-3I. Mobility calculations in the disordered phase (FIG. 5D and FIG. 14D) show that the charge-transport in SFIC is fragile against structural disorder arising from the thermal fluctuations, attributed to the considerable decrease in mobility relative to the crystal phase (FIG. 5F), even though directional mobility and μh>μe are maintained. On the other hand, the mobilities along CH···π are much lower due to the lack of π···π interactions. The site-energy disorder of hole transport (Δh) and electron transport (Δe), arising from local charge-phonon coupling, are found to be similar and 60 meV (i.e., Submitted Δh≈Δe=60 meV) as shown in FIG. 14E, whereas the non-local hole-phonon coupling are larger than non-local electron-phonon coupling (FIG. 5E). Thus, computations reveal that the charge-transport and mobility in SFIC is mainly controlled by the intermolecular interactions, which emphasizes the significance of various interactions in the SFIC crystals. In summary, we have developed a π···π-interaction-5 constructed organic framework (πOF). This kind of 3D ordered microporous structure offers excellent stability and the ability of self-healing and also shows remarkable transport properties with applications in solution processed OFET and OLED devices that take advantage of a π···π transfer. The πOF not only extends the concept of porous molecular frameworks, but also provides a whole new direction towards applications of porous materials in the electronics.

Materials and Methods: ZnMgO dispersion was purchased from Suzhou ever display advanced materials Co., Ltd. CBP was purchased from Lumtec Company. All other chemicals and solvents were purchased from commercial suppliers and used without further purification unless otherwise specified. 1H NMR (400 MHz or 500 MHz) and 13C NMR (125 MHz) spectra were recorded in deuterated solvents on a Bruker ADVANCE 500 or 400 NMR spectrometer. J values are expressed in Hz and quoted chemical shifts are in ppm. The signals have been designated as follows: s (singlet), d (doublet), t (triplet), q (quartet), sd (singlet doublet), dd (doublet doublet) and m (multiplet). High resolution mass spectra (HRMS) were determined on IonSpec 4.7 Tesla Fourier Transform Mass Spectrometer. UV-Vis absorption spectra of the film and solution were obtained using a U-4100 spectrophotometer (Hitachi) equipped with integrating sphere, in which monochromatic light was incident to the substrate side and solution in a 1-cm quartz cell. Cyclic voltammograms (CVs) were recorded on an Epsilon electrochemical workstation using glassy carbon discs as the working electrode, Pt wire as the counter electrode, Ag/AgCl electrode as the reference electrode at a scanning rate of 100 mV/s. 0.1 M tetrabutylammoniumhexafluorophosphate (Bu4NPF6) dissolved in $CH_3CN$ was used as the supporting electrolyte. The microscope images of all the micro-/nanocrystals were acquired by an optical microscope (Vision Engineering Co., UK), which was coupled to a CCD camera. Grazing incident wide angle X-ray scattering (GIWAXS) measurement was performed at Advanced Light Source on the 7.3.3. beamline. All the samples were deposited on the silicon wafer with 100 nm silicon oxide. Samples were irradiated by 10 KeV at a fixed X-ray incident angle of 0.180 with an exposure time of 10 s, the wavelength of incident X-ray is 0.124 nm. Transmission electron microscopy (TEM) was carried out on a JEM 2100 LaB6 at 200 kV. The energy-dispersive X-ray analysis (EDS) and HRTEM images were recorded on a Tecnai F20 transmission electron microscopy under a working voltage of 200 kV. The X-ray diffraction (XRD) data were carried out on a Bruker D8-advance X-ray power diffractometer with Cu-Kα radiation (α=1.5406 Å). $N_2$ adsorption-desorption isotherms were obtained on a Micromeritics ASAP 2460 analyzer (USA) at liquid nitrogen temperature (77 K). The samples were degassed in a vacuum at 80° C. for 6 h prior to the measurement. Pore size distributions were estimated using non-local density functional theory (NLDFT) and BJH (Barret-Joyner-Halenda) model. The surface areas were calculated by the BET (Brunauer-Emmett-Teller) method. The $CO_2$ sorption isotherms were measured by an automatic adsorption equipment (Autosorb-iQ-MP).

Synthetic Details

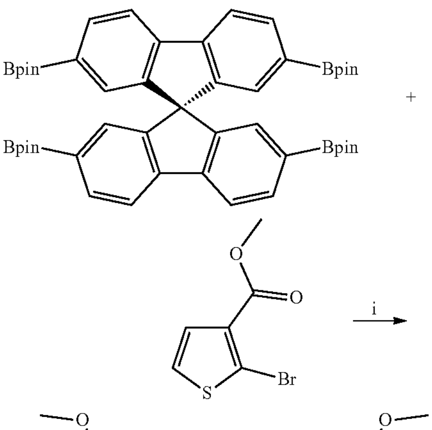

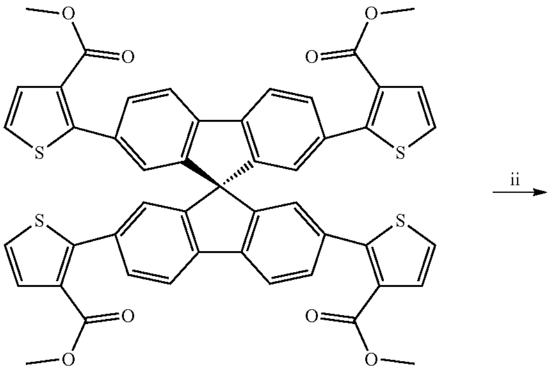

1

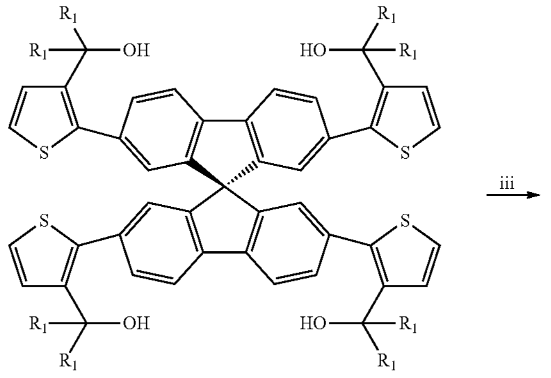

2

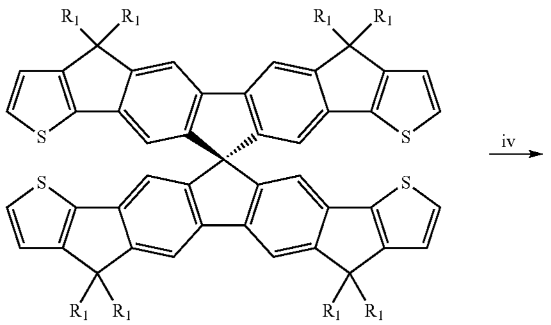

3

-continued

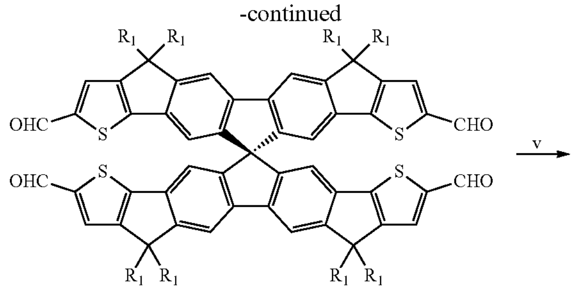

4

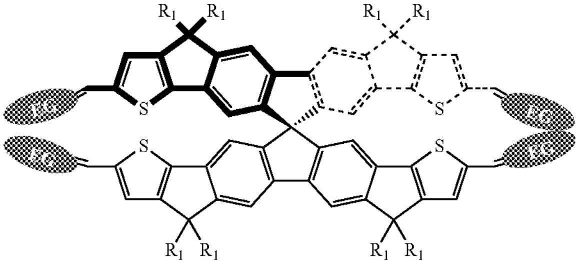

SFIC

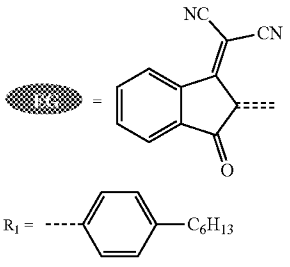

The reaction conditions were (i) Methyl 2-bromothiophene-3-carboxylate (4.5 equiv.), 2,2',7,7'-tetrakis(pinacolatoboryl)-9,9'-Spirobi[9H-fluorene](1.0 equiv), $Pd(PPh_3)_4$ (0.3 equiv), $K_2CO_3$ (2 M)/THF (1:2), 95° C., 72 h. Yield: 80%. (ii) 1-bromo-4-hexylbenzene (22 equiv.), magnesium turnings (26.4 equiv.), THF, RT to 70° C., 20 h. Yield: 85%. (iii) Boron trifluoride diethyl etherate (diluted by chloroform), chloroform, 70° C., 24 h. Yield: 75%. (iv) DMF, $POCl_3$, 0° C. to 90° C., 20 h. Yield: 70%. (v) 2-(3-oxo-2,3-dihydro-1H-inden-1-ylidene) malononitrile (12 equiv.), pyridine (1 ml), chloroform, 70° C., Yield: 90%.

-continued

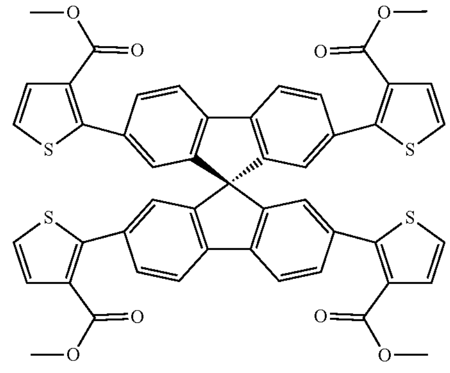

1

Compound 1: A Schlenk flask was charged with 2,2',7,7'-tetrakis(pinacolatoboryl)-9,9'-Spirobi[9H-fluorene](500 mg, 0.61 mmol, 1.0 equiv), Methyl 2-bromothiophene-3-carboxylate(606 mg, 2.74 mmol, 4.5 equiv), THF (6 ml) and $K_2CO_3$ aqueous solution (2 M, 3 ml). The mixture was degassed with argon for 15 min. $Pd(PPh_3)_4$ (211 mg, 0.183 mmol, 0.3 equiv) was added under an argon atmosphere. The mixture was refluxed for 72 h and then cooled to room temperature. 50 mL of water was added and the mixture was extracted with dichloromethane (3×50 mL). The organic phase was dried over anhydrous $MgSO_4$. After removing the solvent, the residue was purified by column chromatography on silica gel, eluted with Hexane/$CH_2Cl_2$ (1:5 v/v) to afford the compound 1 (428 mg, 80% yield) as a pale yellow solid.

$^1$H NMR (400 MHz, $CDCl_3$, 298.5 K) δ=7.90-7.88 (dd, $J_1$=0.36 Hz, $J_2$=7.92 Hz, 4H), 7.57-7.55 (dd, $J_1$=1.68 Hz, $J_2$=7.92 Hz, 4H), 7.42-7.40 (d, J=5.36 Hz, 4H), 7.16-7.14 (d, J=5.36 Hz, 4H), 6.96-6.95 (sd, J=1.16 Hz, 4H), 3.27 (s, 12H).

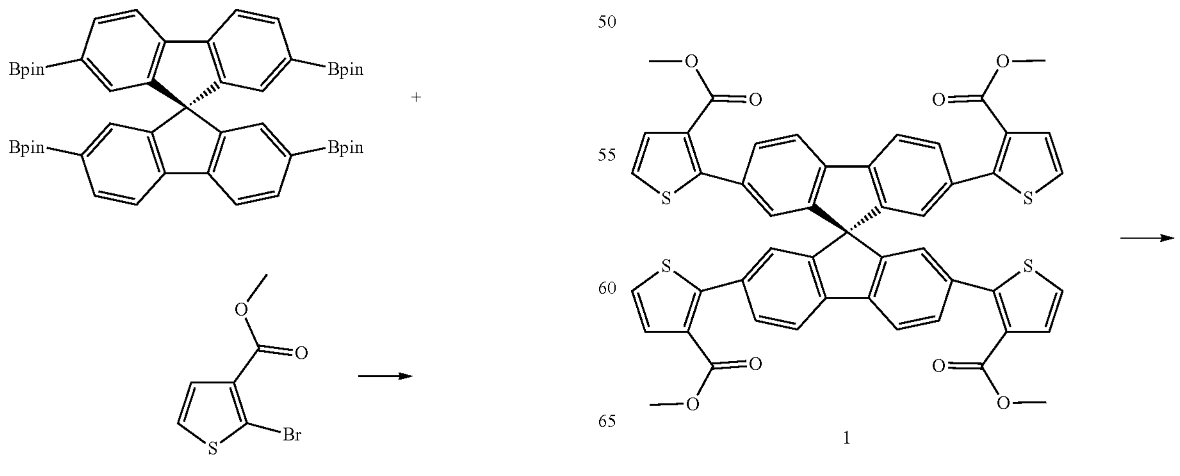

1

-continued

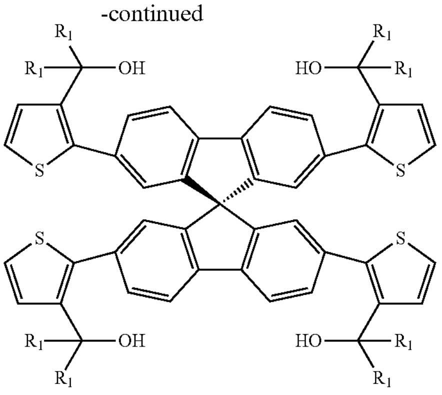

2

Compound 2: A Grignard reagent was freshly prepared by reacting 1-bromo-4-hexylbenzene (3.395 g, 14.475 mmol, 22 equiv) with magnesium turnings (410 mg, 16.975 mmol, 26.4 equiv) in dry THF (13 ml). To a solution of compound 1 (600 mg, 0.643 mmol, 1 equiv) in dry THF (30 ml) was added dropwise the prepared Grignard regent under the argon at room temperature. The reaction mixture was refluxed at 70° C. for 20 h and then quenched with water, followed by extraction with diethyl ether (50 mL×3) and water (100 mL). The collected organic layer was dried over $MgSO_4$. After removal of the solvent under reduced pressure, the crude product was purified by column chromatography on silica gel, eluted with Hexane/$CH_2Cl_2$ (1:2 v/v) to afford the compound 2 as colorless oil liquid. (1.12 g, 85% yields).

$^1$H NMR (400 MHz, $CDCl_3$, 298.5 K) δ=7.52-7.50 (d, J=7.88 Hz, 4H), 7.11-7.09 (m, 4H), 6.98-6.96 (m, 4H), 6.88 (s, 32H), 6.57 (s, 4H), 6.33-6.32 (m, 4H), 2.93 (s, 4H), 2.55-2.51 (t, $J_1$=8.16 Hz, $J_2$=7.24 Hz, 16H), 1.57-1.56 (m, 16H), 1.33 (s, 48H), 0.92-0.91 (m, 24H).

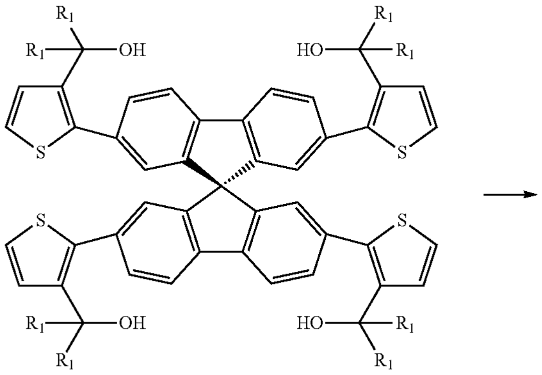

2

-continued

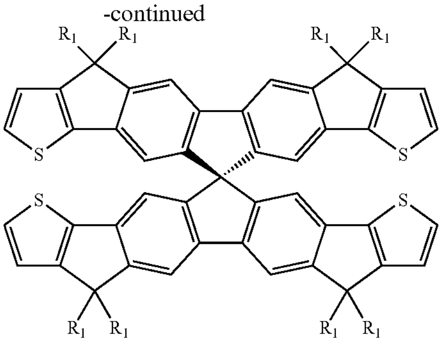

3

Compound 3: The Compound 2 (1.0 g, 0.489 mmol) was dissolved in 150 ml $CHCl_3$. Then a diluted solution of boron trifluoride diethyl etherate (3 ml) in CHCl3 (50 ml) was added dropwise over a period of 30 min at room temperature. The reaction mixture was stirred at 70° C. for 24 h and then cooled to room temperature. The mixture was extracted with water (3×50 mL). The organic phase was dried over anhydrous $MgSO_4$. After removing the solvent, the residue was purified by column chromatography on silica gel, eluted with Hexane/$CH_2Cl_2$ (1:1 v/v) to afford the compound 3 (724 mg, 75% yield) as a yellow sticky solid.

$^1$H NMR (400 MHz, $CDCl_3$, 298.5 K) δ=7.70 (sd, J=0.48 Hz, 4H), 7.21-7.19 (d, J=8.28 Hz, 16H), 7.17-7.16 (d, J=4.84 Hz, 4H), 7.10-7.08 (d, J=8.32 Hz, 16H), 6.92-6.91 (d, J=4.88 Hz, 4H), 6.88 (s, 4H), 2.60-2.56 (t, $J_1$=7.68 Hz, $J_2$=7.96 Hz, 16H), 1.54-1.50 (m, 16H), 1.31 (m, 48H), 0.86 (m, 24H).

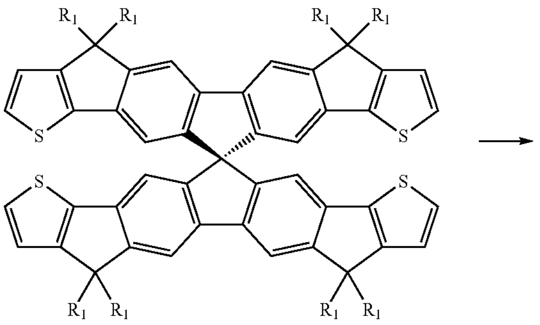

3

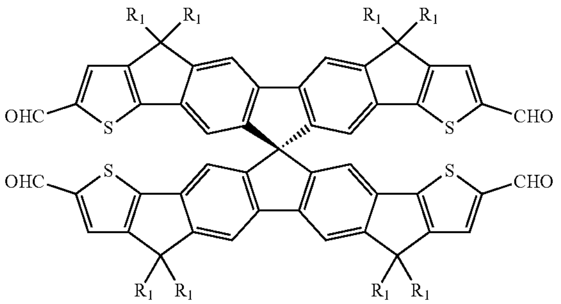

4

Compound 4: To a cold solution of compound 3 (300 mg, 0.15 mmol) in DMF (30 mL), $POCl_3$ (1 ml) was added dropwise at 0° C. under Ar. After being stirred at 90° C. for 20 h, the mixture was poured into ice water (200 ml), neutralized with NaOH, and then extracted with dichloromethane. The combined organic layer was washed with water and brine and dried over anhydrous $MgSO_4$. After removal of solvent, it was purified using chromatography on silica gel using hexane/dichloromethane (1:1) as eluent, yielding a yellow-colored solid (222 mg, 70%).

$^1H$ NMR (400 MHz, $CDCl_3$, 298.5 K) δ=9.75 (s, 4H), 7.78 (s, 4H), 7.58 (s, 4H), 7.18-7.16 (d, J=8.32 Hz, 16H), 7.13-7.10 (d, J=8.4 Hz, 16H), 7.00 (s, 4H), 2.61-2.57 (t, $J_1$=7.92 Hz, $J_2$=7.64 Hz, 16H), 1.63-1.59 (m, 16H), 1.36-1.25 (m, 48H), 0.89-0.87 (m, 24H).

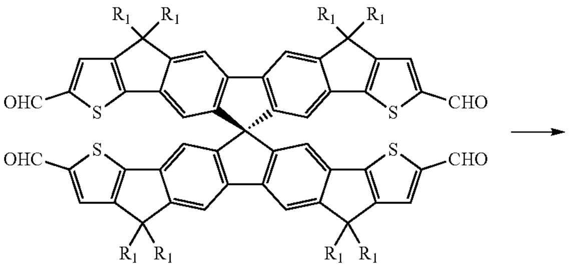

4

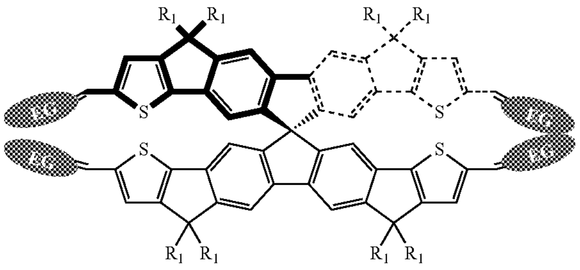

SFIC

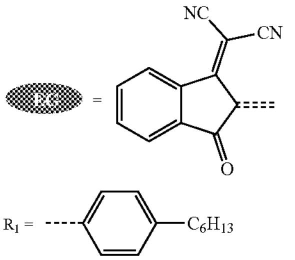

Compound SFIC: Compound 4 (100 mg, 0.048 mmol, 1 equiv) and 2-(3-oxo-2,3-dihydro-1Hinden-1-ylidene) malononitrile (112 mg, 0.575 mmol, 12 equiv) were dissolved in CHCl3 (35 ml), then pyridine (1 ml) was added under argon. The mixture was then refluxed for 18 h, cooled to room temperature, poured into $CH_3OH$ (200 mL) and filtered. The crude product was purified with column chromatography using hexane/dichloromethane (1:1) as eluent to obtain pure SFIC as a black solid (120 mg, 90%).

$^1H$ NMR (500 MHz, $C_2D_2Cl_4$, 373.2 K) δ=8.83 (s, 4H), 8.68-8.66 (d, J=7.70 Hz, 4H), 8.04 (s, 4H), 7.89-7.87 (d, J=7.30 Hz, 4H), 7.78-7.71 (m, 12H), 7.31-7.28 (m, 20H), 7.25-7.23 (d, J=8.25 Hz, 16H), 2.71-2.68 (t, $J_1$=7.60 Hz, $J_2$=7.90 Hz, 16H), 1.76-1.70 (m, 16H), 1.46-1.39 (m, 48H), 0.96-0.0.94 (t, $J_1$=$J_2$=7.00 Hz, 24H); $^{13}C$ NMR (125 MHz, $C_2D_2Cl_4$, 373.2 K): δ=187.76, 160.52, 158.92, 158.18, 157.09, 149.62, 143.09, 142.01, 140.90, 140.57, 140.02, 139.18, 138.18, 137.08, 136.92, 134.91, 134.26, 128.73, 127.98, 125.14, 123.61, 122.40, 119.06, 117.80, 114.54, 35.54, 31.63, 30.84, 29.08, 22.46, 13.91; HRMS (MALDI (N), 100%): calcd (%) for $C_{193}H_{168}N_8O_4S_4$: 2789.20769; found, 2789.20576.

Figure 6:
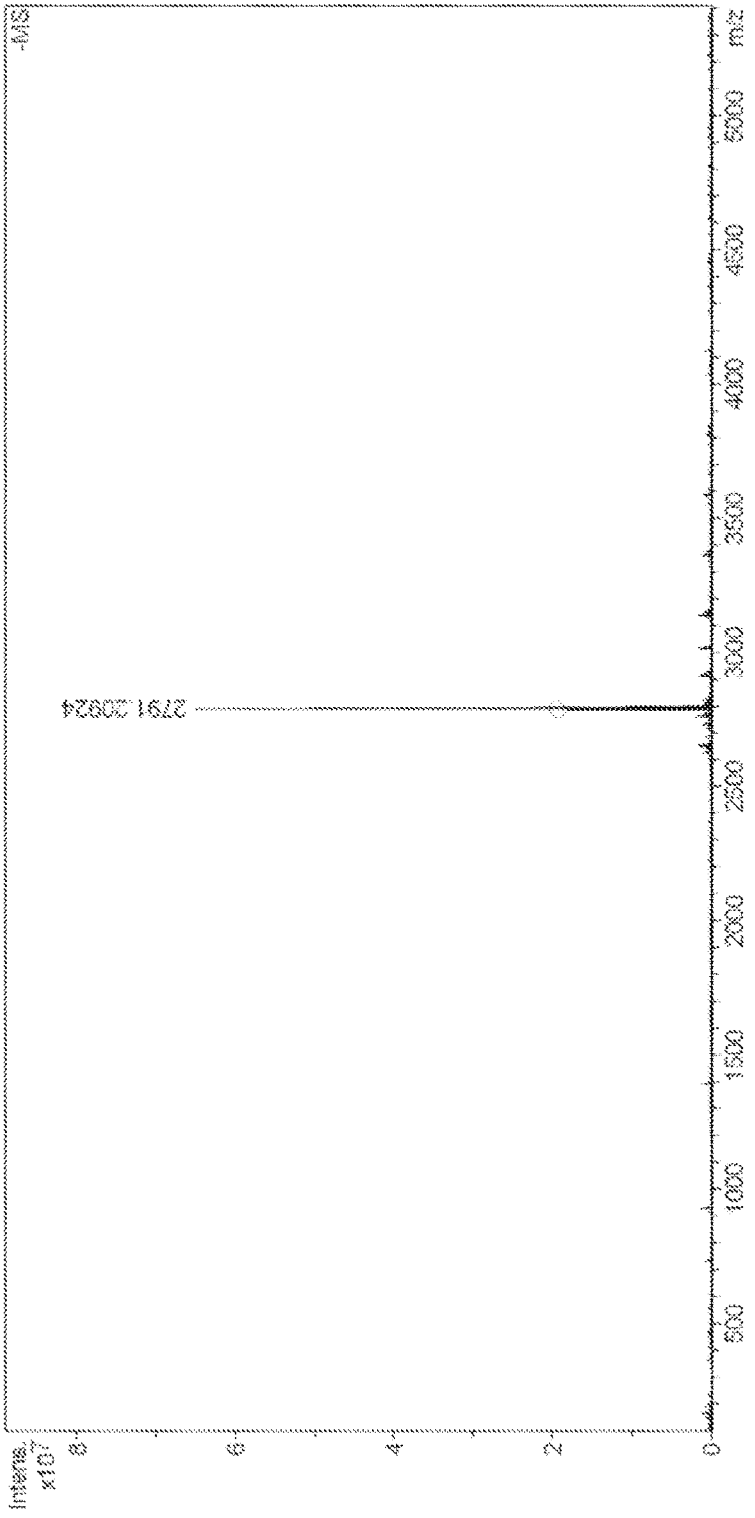
FIG. 6 is a high resolution matrix assisted laser desorption time of flight (HR-MALDI-TOF) mass spectrum of SFIC, according to an embodiment of the present invention.
Figure 7:
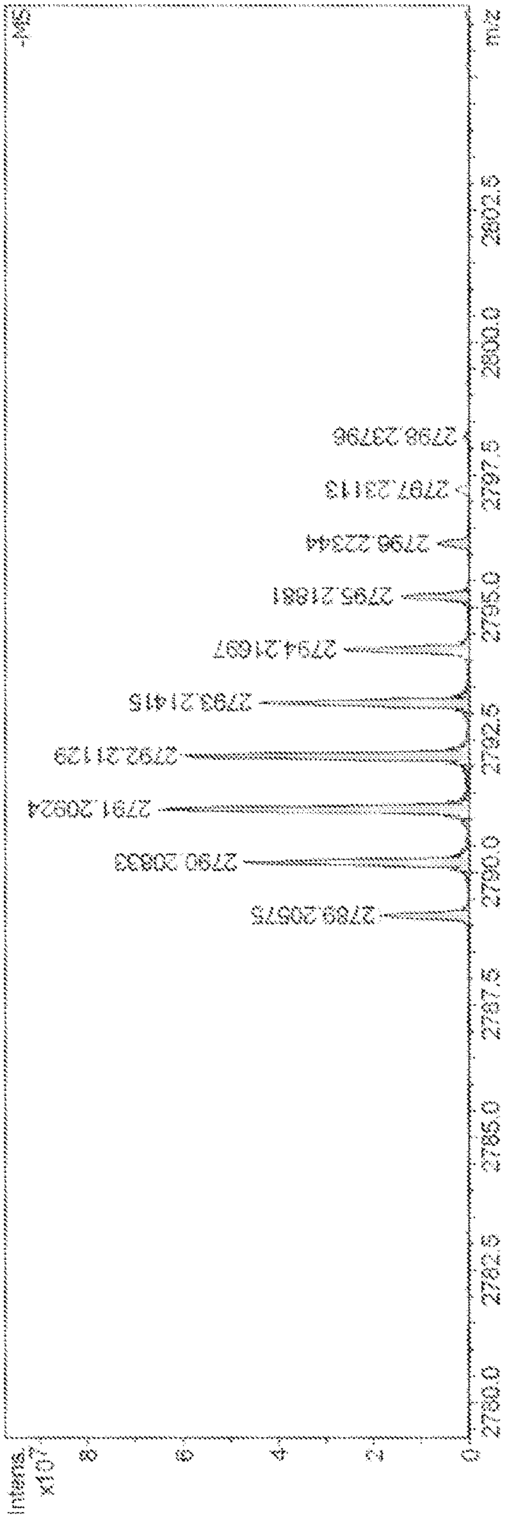
FIG. 7 is a HR-MALDI-TOF mass spectrum of SFIC focused within the range m/z between 2780 and 2802, according to an embodiment of the present invention.

FIG. 6 is a HR-MALDI-TOF mass spectrum of SFIC, according to an embodiment of the present invention. FIG. 7 is a HR-MALDI-TOF mass spectrum of SFIC focused within the range m/z between 2780 and 2802, according to an embodiment of the present invention.

FIG. 8 shows a plot of weight in percent versus temperature (TGA curve) of SFIC under nitrogen flow, according to an embodiment of the present invention.

X-ray Crystal Structure: The single crystals of SFIC were obtained by slow vapor diffusion method under the $CHCl_3$ (good solvent) and $CH_3OH$ (poor solvent). Single crystal data collections were performed on a MM007HF Saturn724+ diffractometer using Cu Ka radiation (1.54184 Å) at about 170 K. Using Olex2, these structures were solved with the ShelXS and refined with the ShelXL-2014 refinement package using the Least Squares minimization. Refinement was performed on F2 anisotropically for all the non-hydrogen atoms by the full-matrix least-squares method. The hydrogen atoms were placed at the calculated positions and were included in the structure calculation without further refinement of the parameters. Because of the very large thermal motion and disorder of solvent molecules in the lattice, the diffuse residual electron density was difficult to model accurately and thus, a treatment by SQUEEZE (from PLATON) was used for solvate molecules in SFIC, which leads to large solvent accessible voids in structures. Despite many attempts, the diffraction intensity peaks of SFIC stayed weak due to insufficient quality of single crystals, which led to their high R values and alerted of level A in checkCIF reports.

Table 1 provides Crystallographic data and structure refinement details for SFIC.

TABLE 1

| | SFIC |
|---|---|
| T (K) | 173 (2) |
| λ (Å) | 1.54184 |
| cryst syst | orthorhombic |
| space group | P n n a |
| a, (Å) | 31.0504 (13) |
| b, (Å) | 32.263 (2) |
| c, (Å) | 21.7390 (13) |
| α, (deg) | 90.00 |
| β, (deg) | 90.00 |
| γ, (deg) | 90.00 |
| V, (Å$^3$) | 21778 (2) |
| Z | 8 |
| $D_{calc}$, (g/cm$^3$) | 0.851 |
| μ (mm$^{-1}$) | 0.734 |
| F(000) | 5912 |
| Theta range, (deg) | 2.48-76.56 |
| reflns collected | 1274665 |
| indep reflns/$R_{int}$ | 21524/0.2642 |
| params | 946 |
| GOF on $F^2$ | 1.063 |
| $R_1$, $wR_2$ [I > 2σ(I)] | 0.1575/0.3702 |
| $R_1$, $wR_2$ (all data) | 0.2312/0.4184 |

Figure 9:
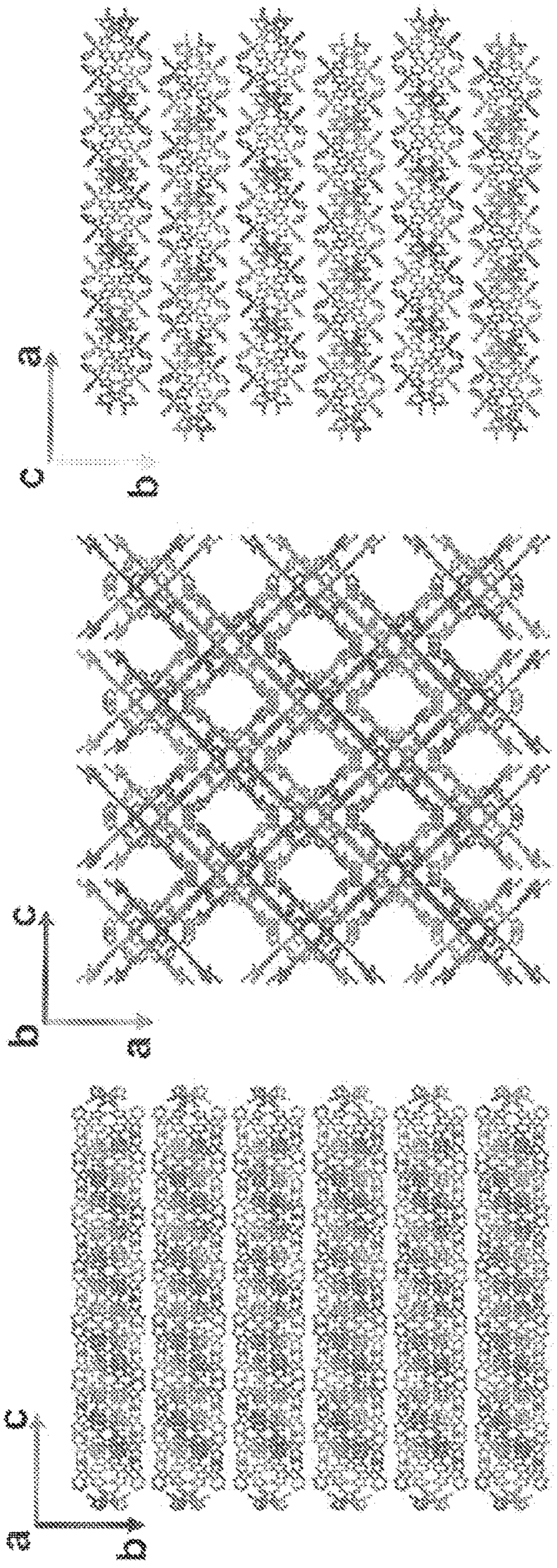
FIG. 9 shows a crystal 3D-stacking model of SFIC, according to an embodiment of the present invention.
Figure 10:
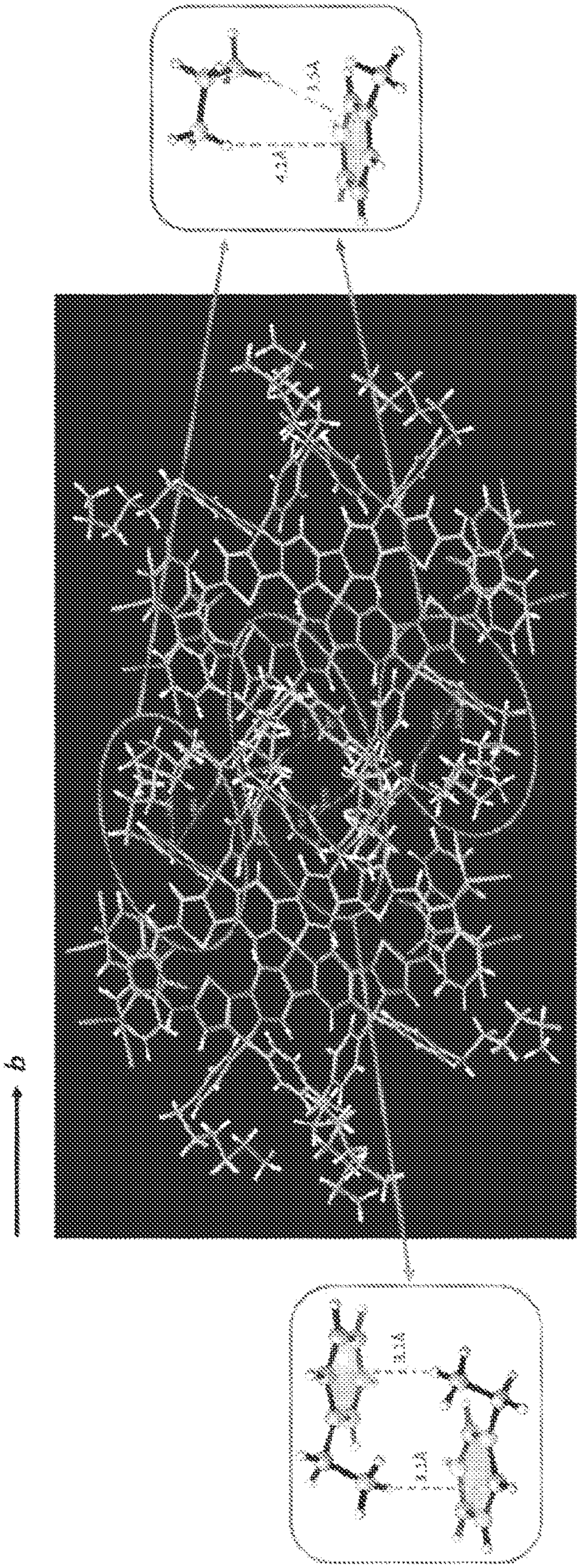
FIG. 10 shows the CH···π interactions between two layers in the crystal along the b axis, according to an embodiment of the present invention.
Figure 11:
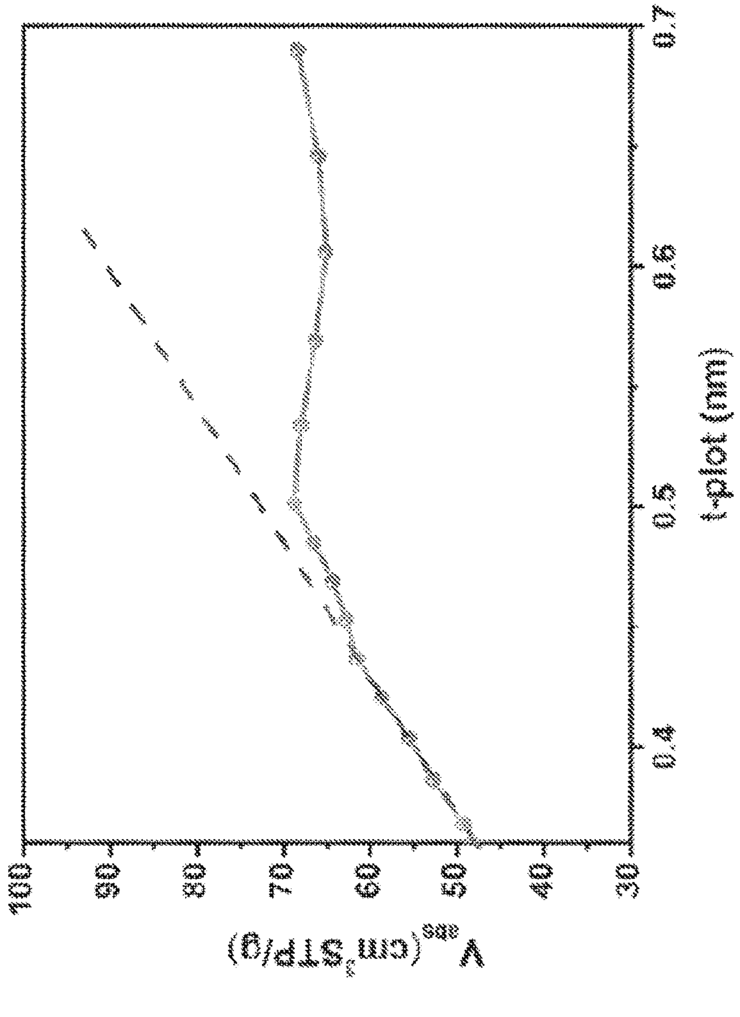
FIG. 11 shows the t-Plot for nitrogen adsorption of SFIC at 77K, according to an embodiment of the present invention.

FIG. 9 shows a crystal 3D-stacking model of SFIC, according to an embodiment of the present invention. FIG. 10 shows the CH···π interactions between two layers in the crystal along the b axis, according to an embodiment of the present invention. FIG. 11 shows the t-Plot for nitrogen adsorption of SFIC at 77K, according to an embodiment of the present invention.

Transistor Device Fabrication and Characterization: The substrates were cleaned first with pure water, then piranha solution (H2SO4/H2O2=7:3), pure water and finally with pure isopropyl alcohol, and then blown dry with high-purity nitrogen gas. Treatment of the Si/SiO2 wafers with OTS was carried out by the vapor-deposition method. The clean wafers were dried under vacuum at 90° C. for 0.5 h to eliminate moisture. When the temperature decreased to 70° C., a small drop of OTS was placed around the wafers. Subsequently, this system was heated to 120° C. and maintained for 2 h under vacuum. Micro-/nano-crystals were formed using a dilute CHCl3 solution (1 mg mL-1). Bottom-gate top-contact OFETs based on the micro-/nano-crystals were constructed on an OTS modified $Si/SiO_2$ substrate (n-type Si wafer containing 300 nm-thick SiO2) using an "organic ribbon mask" technique. Prior to self-assembly of micro-/nano-crystals, the OTS modified $Si/SiO_2$ substrate was cleaned with pure n-hexane, pure chloroform and pure isopropyl alcohol. Then, micro-/nano-crystals were produced on $Si/SiO_2$ substrates through drop casting. Subsequently, 40 nm thick source and drain electrodes were deposited on the micro-/nano-crystals by thermal evaporation. Electrical characteristics of the devices were tested with a Keithley 4200-SCS semiconductor parameter analyzer and a Micromanipulator 6150 probe station in a glove box at room temperature. The mobilities were calculated from the saturation region with the following equation: IDS=(W/2L) Cip (VG-VT) 2, where IDS is the drain-source current, W is the channel width, L is the channel length, p is the field effect mobility, Ci is the capacitance per unit area of the gate dielectric layer and VG and VT are the gate voltage and threshold voltage, respectively. This equation defines the important characteristics of electron mobility (μ), on/off ratio (Ion/off) and threshold voltage (VT), which could be deduced from the equation using the current-voltage plot.

Table 2 provides Field-effect electron (e) and hole (h) mobilities of four OFET devices with different crystal planes.

TABLE 2

| Device | W/L (μm) | $\mu h^{max}$ ($cm^2\ V^{-1}\ s^{-1}$) | $V_t$/V | On/off Ratio |
|---|---|---|---|---|
| 1-2 | 14.72/2.92 | $2.28 \times 10^{-3}$ (h) | −29.06 | $3.49 \times 10^3$ |
| | | $6.92 \times 10^{-4}$ (e) | 41.33 | $6.49 \times 10^3$ |
| 2-3 | 15.56/2.36 | $5.43 \times 10^{-4}$ (h) | −41.21 | $1.98 \times 10^4$ |
| | | $1.29 \times 10^{-4}$ (e) | 36.81 | $9.95 \times 10^2$ |
| 3-4 | 22.64/3.47 | $1.13 \times 10^{-3}$ (h) | −31.00 | $3.61 \times 10^4$ |
| | | $2.02 \times 10^{-4}$ (e) | 48.30 | $7.25 \times 10^3$ |
| 4-1 | 20.56/3.33 | $3.17 \times 10^{-4}$ (h) | −35.86 | $1.01 \times 10^4$ |
| | | $1.69 \times 10^{-4}$ (e) | 44.32 | $3.13 \times 10^3$ |

OLED device fabrication and characterization: The ITO-covered glass slides were cleaned with detergent water, acetone and ethanol each for 30 min by sonication, and finally blown dry with high-purity nitrogen gas. Before deposition of emission layer, ZnMgO nanoparticles dispersed in n-butyl alcohol (40 mg/ml) were spin-coated on ITO substrate, and treated at 120° C. for 15 min. After, SFIC dissolved in chloroform (2 mg/ml) was spin-coated onto ZnMgO-coated ITO glass, followed by annealing at 80° C. for 2 min. The device fabrication process was completed by depositing CBP, M003 and Au layers in thermal evaporation chamber with a vacuum pressure below 4×10−4 Pa. The current-voltage characteristics were measured with a computer controlled Keithley 2400 source meter. Electroluminescence spectra were collected using a photonic multichannel analyzer PMA-12 (Hamamatsu C10027-01). The external quantum efficiency of the devices (calculated in the range of 380-780 nm) was obtained by measuring the light intensity in the forward direction using an integrating sphere (Hamamatsu A10094). All the measurements were carried out under ambient atmosphere at room temperature.

FIGS. 12A and 12B show OLED characterization of SFIC on a standard device, according to an embodiment of the present invention. FIG. 12A shows the radiance and current density as a function of applied voltage in SFIC emitter-based OLED, according to an embodiment of the present invention. FIG. 12B shows EQE as a function of applied voltage in SFIC emitter-based OLED, according to an embodiment of the present invention. FIG. 12C shows voltage-dependent EL spectra of SFIC emitter based OLED, according to an embodiment of the present invention.

Figure 13B:
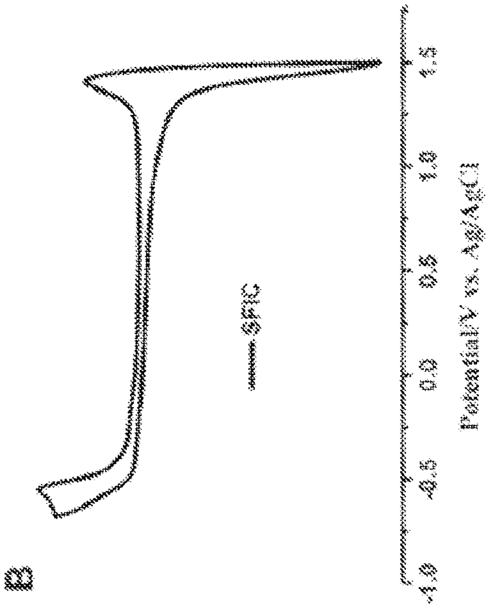
FIG. 13B shows the cyclic potential versus Ag/AgCl or voltammogram of SFIC film, according to an embodiment of the present invention.
Figure 13A:
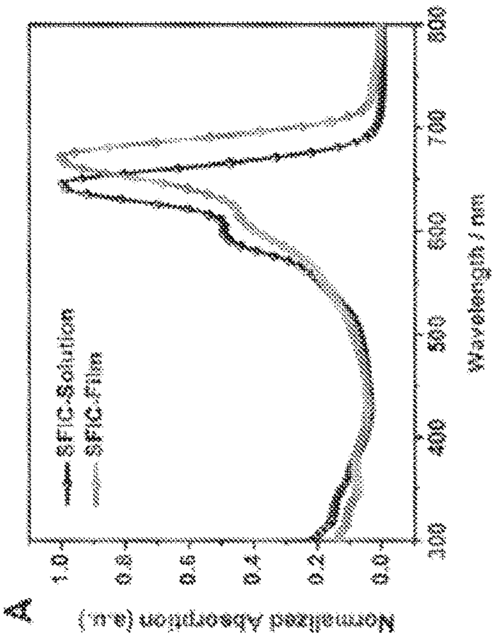
FIG. 13A shows ultraviolet and visible (UV-VIS) absorption spectra of SFIC in CHCl3 (black) and film (red), according to an embodiment of the present invention.

FIG. 13A shows UV-VIS absorption spectra of SFIC in $CHCl_3$ (black) and film (red), according to an embodiment of the present invention. FIG. 13B shows the cyclic potential versus Ag/AgCl or voltammogram of SFIC film, according to an embodiment of the present invention.

Table 3 provides a Summary of optical and electronic properties of SFIC.

TABLE 3

| | $\lambda^a_{max-s}$ [nm] | $\lambda^b_{max-f}$ [nm] | $\lambda^a_{onset-s}$ [nm] | $\lambda^b_{onset-f}$ [nm] | $E^c_{LUMO}$ [eV] | $E^d_{HOMO}$ [eV] | $E^e_{g-E}$ [eV] | $E^f_{g-opt-f}$ [eV] |
|---|---|---|---|---|---|---|---|---|
| SFIC | 644 | 671 | 681 | 709 | −3.94 | −5.77 | 1.83 | 1.75 |

a λmax was measured in CHCl3 solution. b λmax was measured in film. c Estimated from the onset potential of the first reduction wave and calculated according to ELUMO=−(4.4+ Eonsetre) eV. d Estimated from the onset potential of the first oxidation wave and calculated according to EHOMO=−(4.4+Eonset ox) eV. e Eg-E (eV) calculated according to Eg-E=(ELUMO−EHOMO) eV. f Obtained from the edge of the absorption spectra in film according to Eg=(1240/λonset).

Multi-scale computational characterization of charge-transport: Atomistic morphologies and charge-transport in bulk SFIC are calculated from Molecular Dynamics (MD) and kinetic Monte Carlo (kMC) simulations, respectively. The initial bulk supercell of SFIC was grown from the duplications of the experimental unit-cell along a, b, c crystallographic directions given in Table 1. A supercell containing a total of 576 SFIC molecules (217,152 atoms) were considered for these simulations. AMBER software with GAFF force-fields for molecular mechanics parameters were employed for all MD simulations. Partial atomic charges of SFIC using RESP were obtained based on the Merz-Singh-Kollman (MSK)scheme from B3LYP/6-31G(d) optimized geometries in the gas-phase (33). In the MD simulations, the supercell was first gradually heated from 0 K to 300 K for 2 ns, while keeping the heavy-atom positions restrained in order to avoid catastrophic changes. It was then relaxed for 2 ns at 300 K using a Langevin thermostat and another 2 ns equilibration run was performed with reduced restraint, with Berendsen barostat to maintain the pressure at 1 atm (34). Finally, all heavy-atom restraints were removed, and a final 20 ns production run was performed. The atomistic morphology seen in FIG. 5D and FIGS. 14A-14F are a snapshot of this production run. For charge-transport simulations, we employed incoherent transport mechanism and calculated hole and electron mobilities from the rate-based kinetic Monte Carlo simulations based on localized charge approximation. The hole (A+A+→A++A) and electron (A+A−→A−+A) transport rates are evaluated by the non-adiabatic Marcus-Levich-Jortner (MLJ) expression including quantum-mechanical corrections by equation (1).

$$k_{ij} = \frac{2\pi}{\hbar} J_{ij}^2 \frac{1}{\sqrt{4\pi\lambda_{out}k_B T}} \sum\nolimits_v \exp[-S]\frac{S^v}{v!}\exp\left[-\frac{(\lambda_{out} + \Delta E_{ij} + v\hbar\omega)^2}{4\lambda_{out}k_B T}\right] \quad (1)$$

where Jij is the transfer integral, S is the Huang-Rhys factor, S=λi/ℏω is the internal reorganization energy and ℏω is the mode frequency, λout is the external reorganization energy (λ=λin+λout), and ΔEij=Ei−Ej is site-energy difference. A value of 200 meV is used for both ℏω and λout (35). The internal reorganization energies are calculated from: Δh=E0(q+)−E0(q0)+E+(q0)−E+(q+) and λe=E0(q−)−E0(q0)+E−(q0)−E−(q−) using B3LYP/6-31G(d). The internal reorganization energies of SFIC are found to be 82 meV for both hole and electron transport, which results in a total λ=282 meV of reorganization energy. The binding energies of the π···π, x···x and CH···π dimers are calculated using B97D/6-31G(d,p) and from Ebind=Ec−(Ea+Eb), where Ec is the energy of the complex, Ea and Eb are the constituting monomers. Transfer integrals are evaluated using ZINDO method and site-energies are calculated using Thole model, where RESP partial charges are calculated from MSK and atomic polarizabilities are reparametrized from B3LYP/6-31G(d) calculated molecular polarizabilities. kMC simulations are performed for a single hole (or electron) carrier in an electric field ($\vec{E}$) in the equilibrated cell and periodic boundary conditions are imposed (resulting in a charge density of ~1023 m−3). Hole and electron mobilities are calculated from μ=v·ê/E. All DFT calculations are performed in Gaussian09 (36) and all charge-transport calculations and simulations are performed in VOTCA_package (37).

Figure 14A:
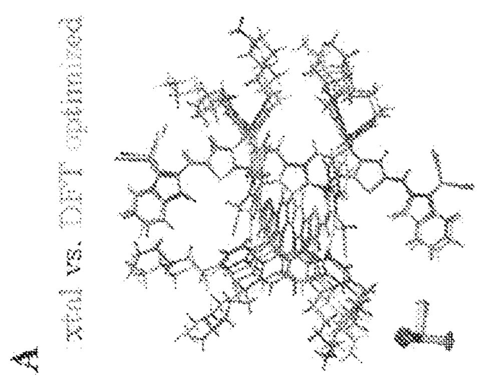
FIG. 14A shows a comparison of single SFIC geometry from x-ray measurements and B3LYP/6-31G(d) gas-phase optimization calculations, according to an embodiment of the present invention.
Figure 14C:
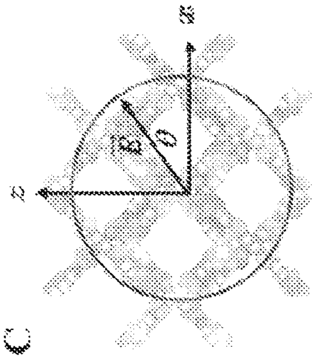
FIG. 14C is a diagram showing electric field variation for direction-resolved transport calculations, according to an embodiment of the present invention.
Figure 14D:
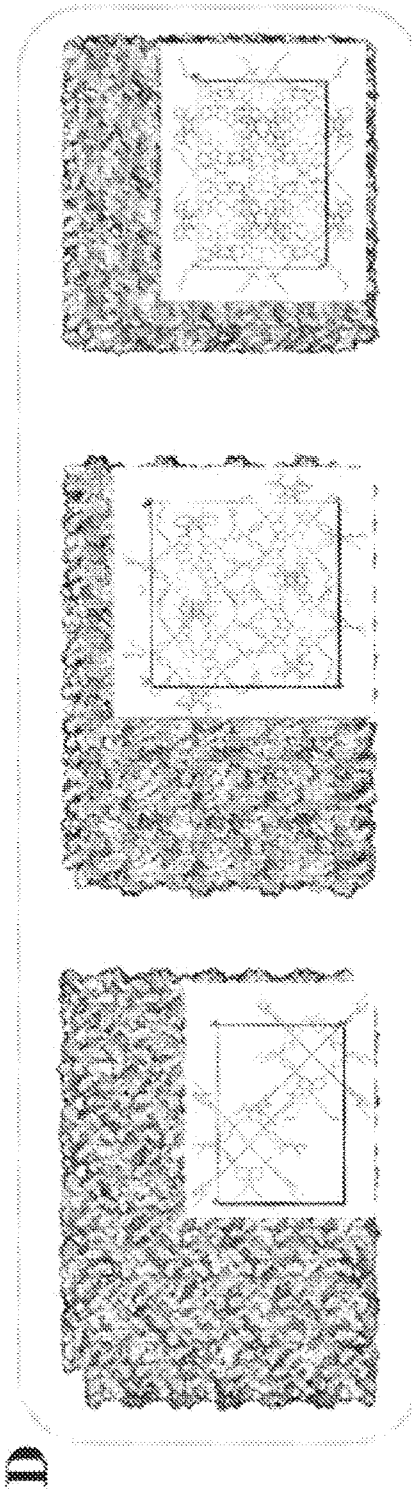
FIG. 14D is a MD-equilibrated atomistic morphologies of SFIC along three different packing directions, according to an embodiment of the present invention.
Figure 14E:
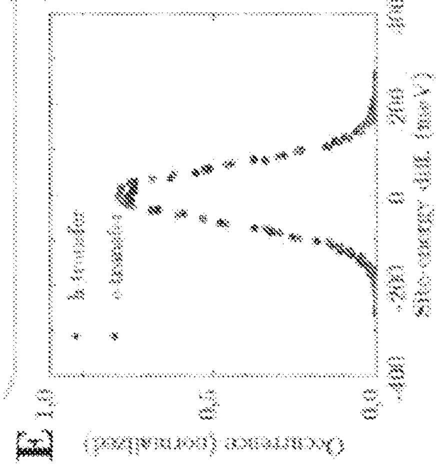
FIG. 14E is a calculated site energy difference distributions, based on Thole model, for hole and electron transfers, according to an embodiment of the present invention.
Figure 14F:
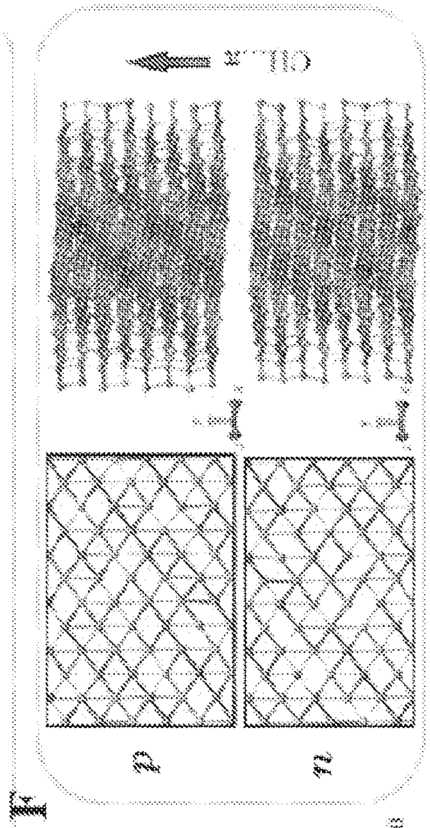
FIG. 14F shows connectivity graphs in SFIC based on the strength of the hole (p) and electron (n) transfer integrals, according to an embodiment of the present invention.
Figure 15A:
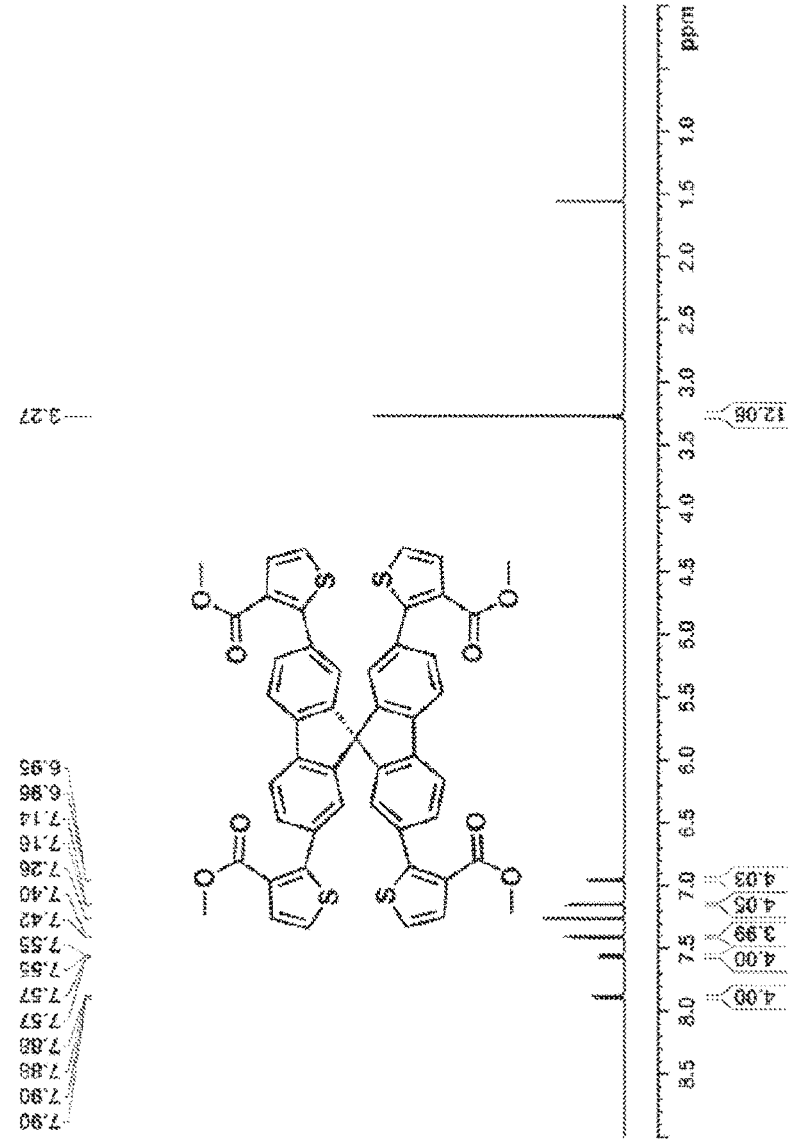
FIGS. 15A-15F shows various nuclear magnetic resonance (NMR) spectra of various compounds used and SFIC, according to an embodiment of the present invention.
Figure 15B:
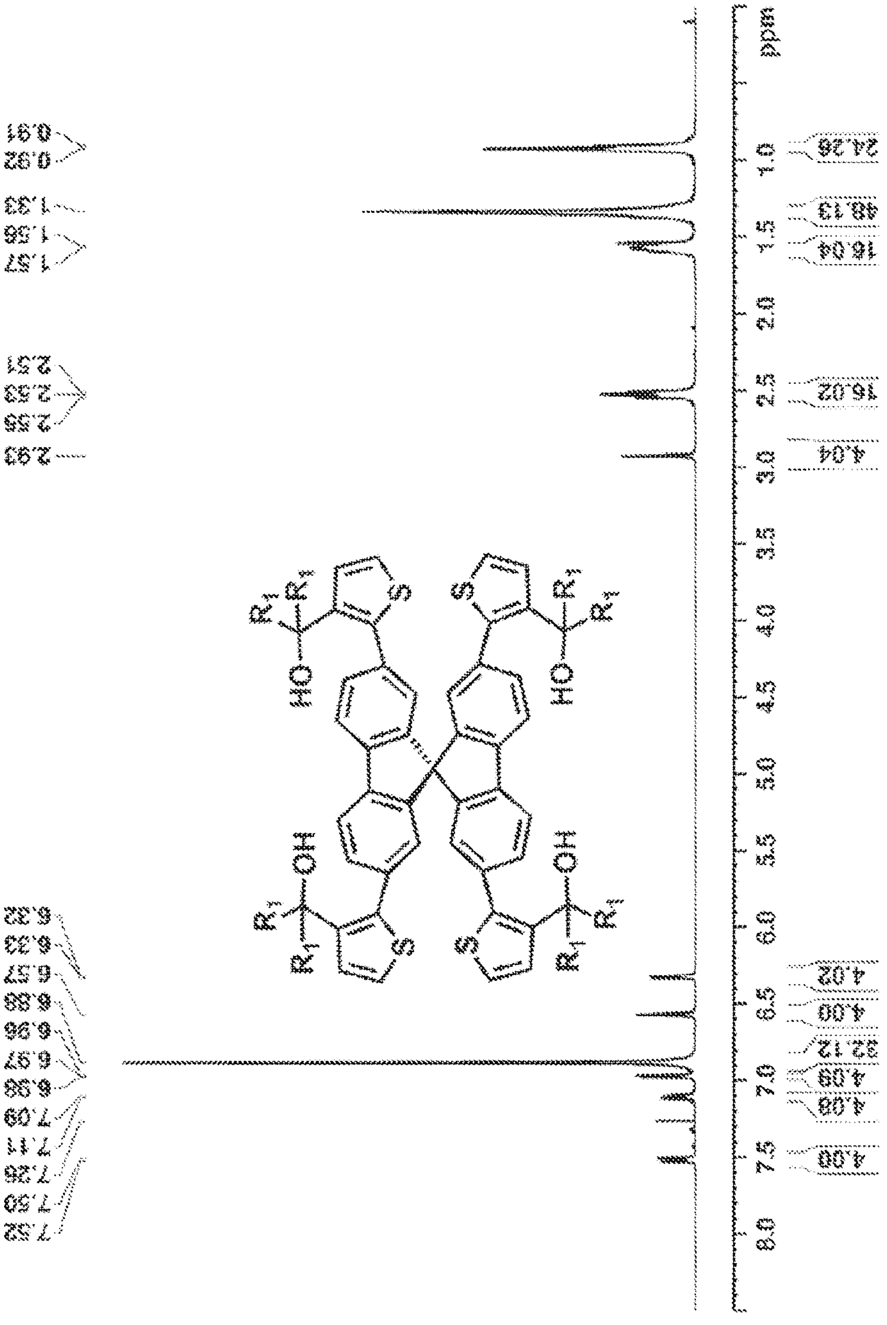
Figure 15C:
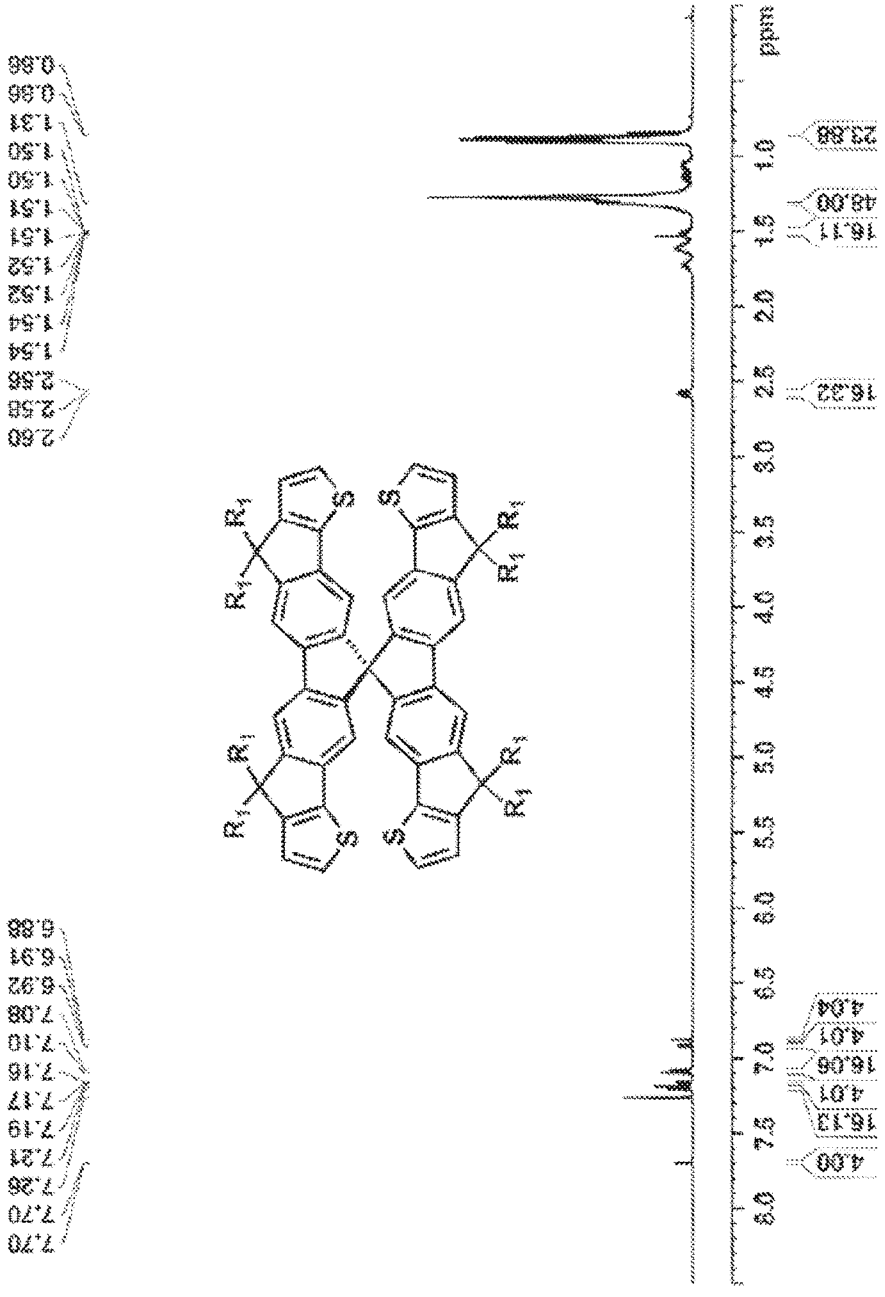
Figure 15D:
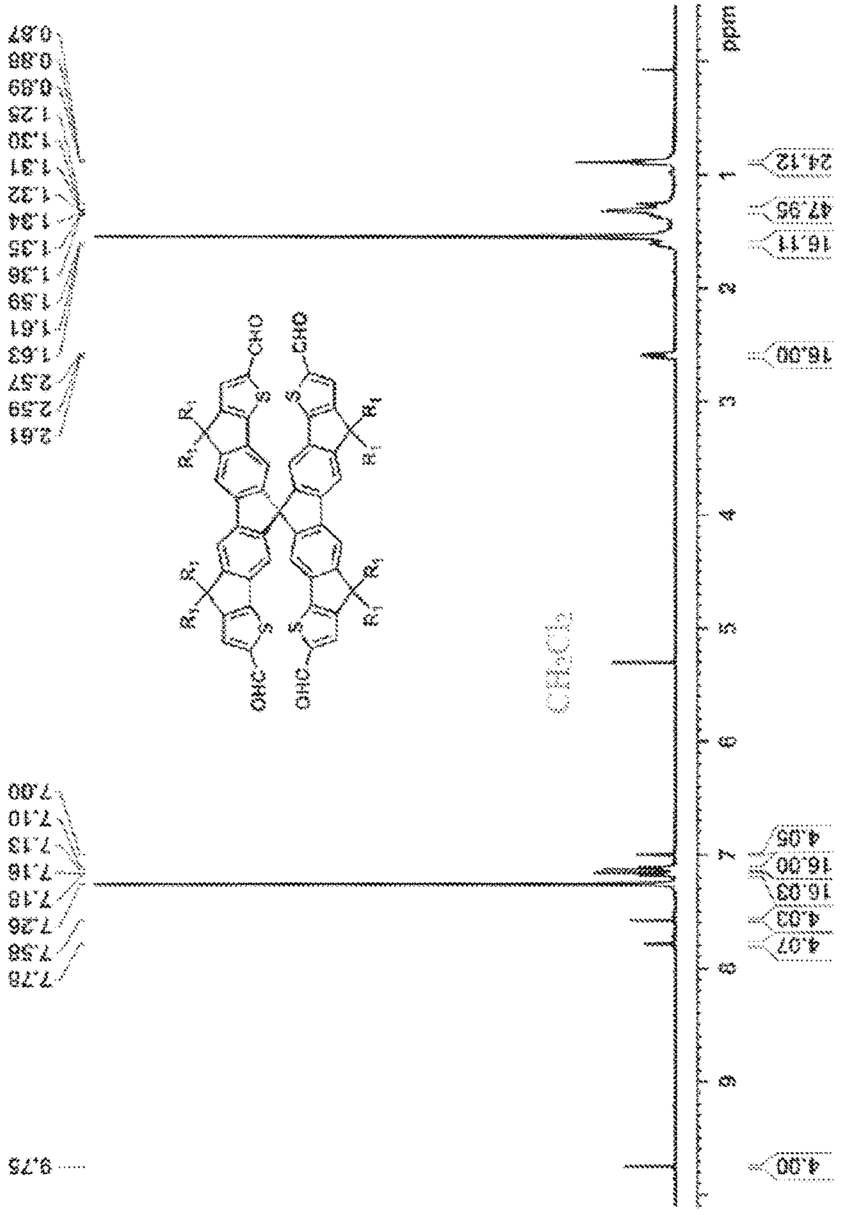
Figure 15E:
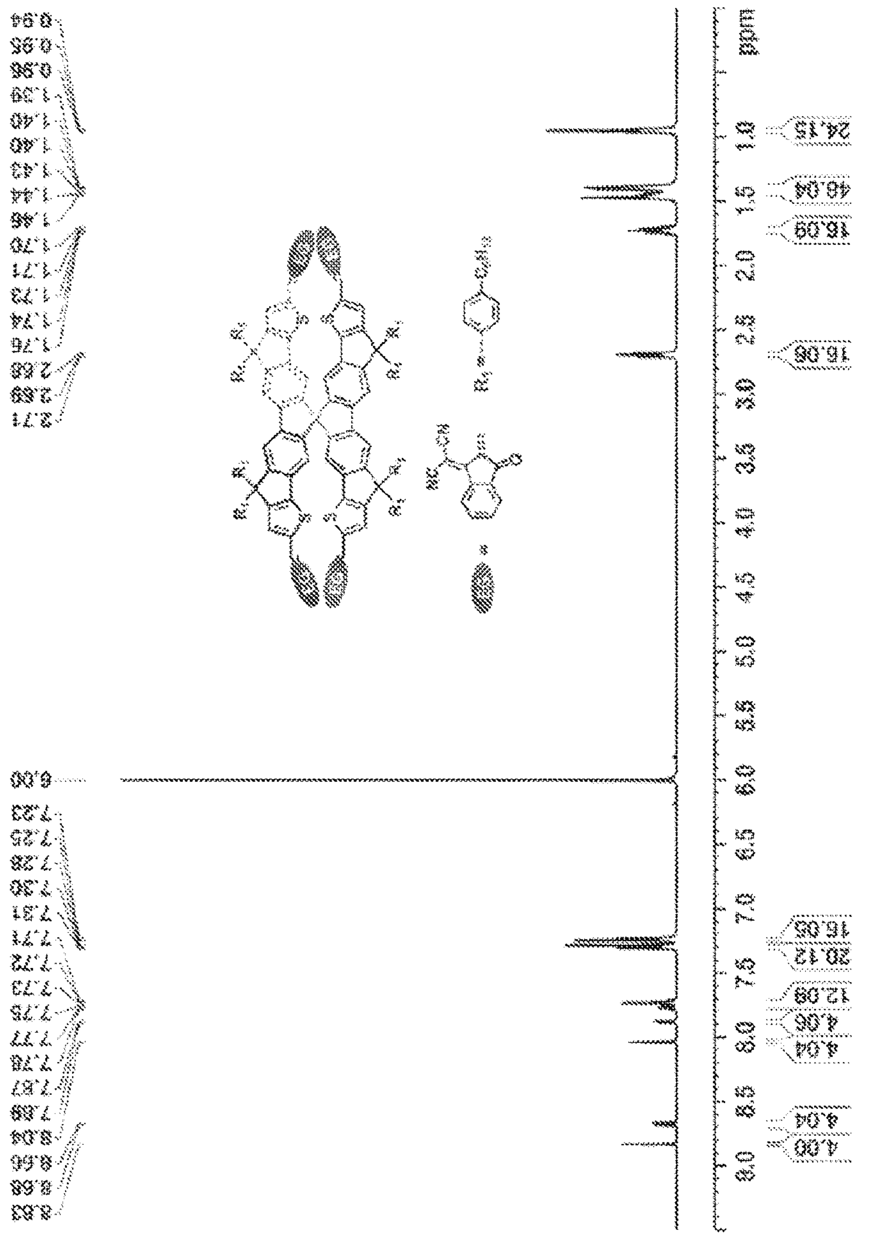
Figure 15F:
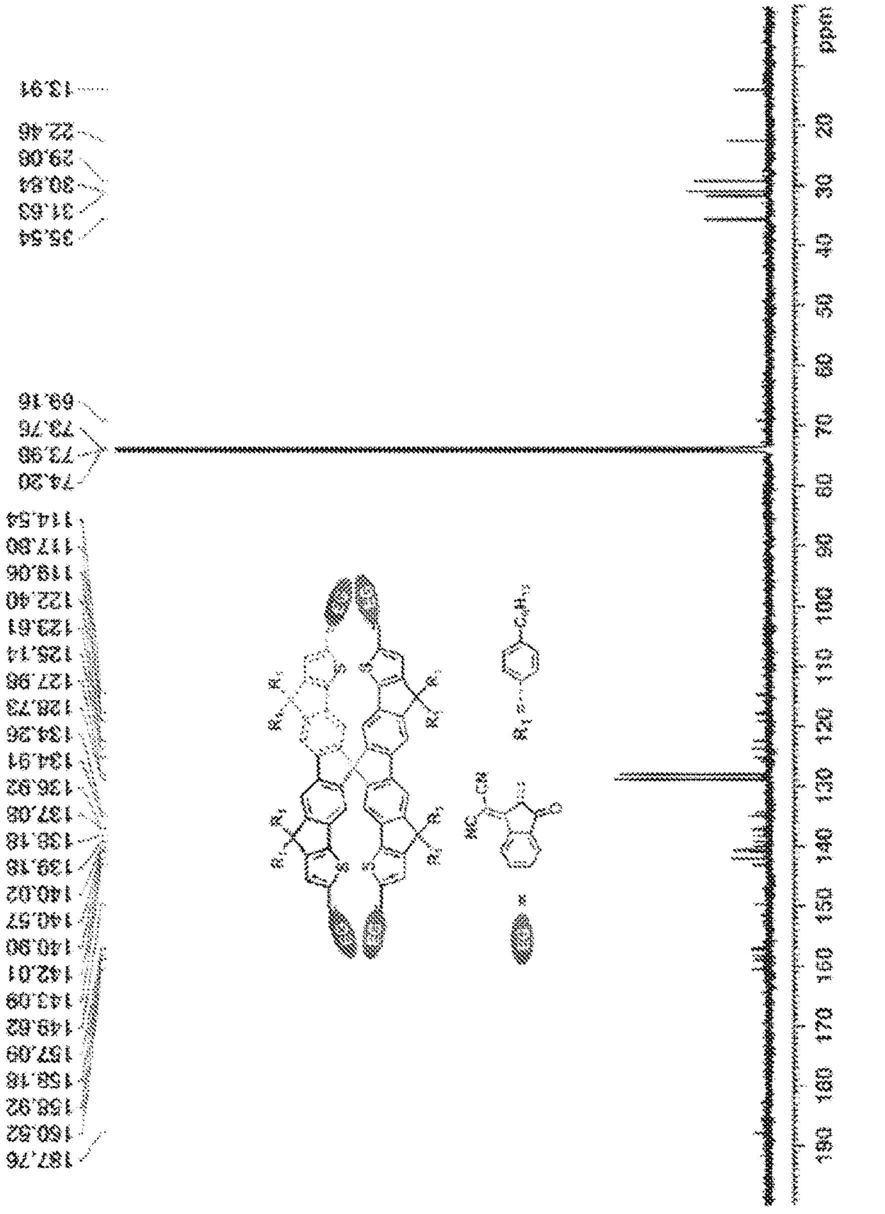

FIG. 14A shows a comparison of single SFIC geometry from x-ray measurements and B3LYP/6-31G(d) gas-phase optimization calculations, according to an embodiment of the present invention. FIG. 14B shows three possible SFIC pair interactions present in the crystal and the corresponding B97D/6-31G(d,p)-calculated dimer binding energies, according to an embodiment of the present invention. FIG. 14C is a diagram showing electric field variation for direction-resolved transport calculations, according to an embodiment of the present invention. FIG. 14D is a MD-equilibrated atomistic morphologies of SFIC along three different packing directions, according to an embodiment of the present invention. FIG. 14E is a calculated site energy difference distributions, based on Thole model, for hole and electron transfers, according to an embodiment of the present invention. FIG. 14F shows connectivity graphs in SFIC based on the strength of the hole (p) and electron (n) transfer integrals, according to an embodiment of the present invention. Green dots are site positions. For J>1 meV the bonds are in red and for 0.1 meV<J<1 meV range the bonds are in blue. Missing bonds are less than 0.1 meV. (left column) The connectivity on a single π···π plane, (right column) the connectivity for all directions, according to an embodiment of the present invention.

Material properties: Although the noncovalent π···π and CH···π interactions are weak, the πOF shows excellent stability, as demonstrated by variable-temperature and recycling-test PXRD experiments, and exhibit self-healing properties, in which the parent porosity is recovered upon solvent annealing at room temperature. It also shows near-infrared light emission at 700 nm. Furthermore, πOFs are novel organic porous materials based on noncovalent π···π interactions between molecular units. The framework can be disrupted by optical excitation according to its bandgap. Here, we propose to exploit stimuli-responsive drug delivery by using novel organic porous materials based on noncovalent π···π interactions for controllable release of drug.

Drug delivery and release applications: Organic porous crystal materials have created numerous opportunities for biomedical applications. COFs are a representative platform for developing organic porous materials with designable structure and properties. Drug loading and delivery takes advantage of the large specific surface area of organic porous materials. Bai et al. reported nanoscale polyimide-based COFs loaded with antitumor drugs and demonstrated considerable therapeutic effect. Besides, depending on the chemical composition and modifications, organic porous materials have demonstrated tunable properties in different application scenarios. For example, targeted drug delivery has been reported by adding targeting ligands on nanoscale COFs. 2D COFs were also developed as photosensitizers or photothermal agents for photodynamic therapy and photothermal therapy, respectively.

Stimuli-responsive delivery of drugs is an effective way to achieve spatially and temporally controlled drug release. In recent years, various stimuli-responsive strategies have been employed, sensitive to external triggers or biological signals. For example, molecular conformational change of liposomes mediated by hyperthermia can accelerate the release of therapeutics. Conventional organic porous materials, such as COFs, are restricted by covalent bonding, so it is difficult to manipulate the drug release process via stimuli signals. πOFs are novel organic porous materials based on π···π interactions between molecular units. The framework can be disrupted by optical excitation according to its bandgap. Here, we propose to exploit stimuli-responsive drug delivery by using novel organic porous materials based on π···π interactions.

Drug loading capability of SFIC: πOFs can provide a universal platform for drug loading. We investigated the drug loading capability of SFIC by mixing it with an antitumor drug R848, which can drive the polarization of tumor-associated macrophages and control tumor growth. Both SFIC and R848 were dispersed in methanol and the mixture was stirred by ultrasound. The hydrophobic interaction between the drug and SFIC allows the attachment and encapsulation of R848 in porous SFIC. The mixture was centrifuged after stirring and the amount of R848 in supernatant was measured by high performance liquid chromatography (HPLC). FIG. 12C exhibit the standard curve of R848 in methanol solution. The encapsulation efficiency and loading capability of R848 in SFIC were calculated by the following equations (2) and (3).

$$\text{Encapsulation efficiency (\%)} = \frac{\text{Amount of drug in } SFIC}{\text{Total amount of drug}} \times 100\% \quad (2)$$

$$\text{Loading capability (\%)} = \frac{\text{Amount of drug in } SFIC}{\text{Total weight of } SFIC \text{ and drug in } SFIC} \times 100\% \quad (3)$$

FIGS. 15A-15F shows various NMR spectra of various compounds used and SFIC, according to an embodiment of the present invention.

Figure 16:
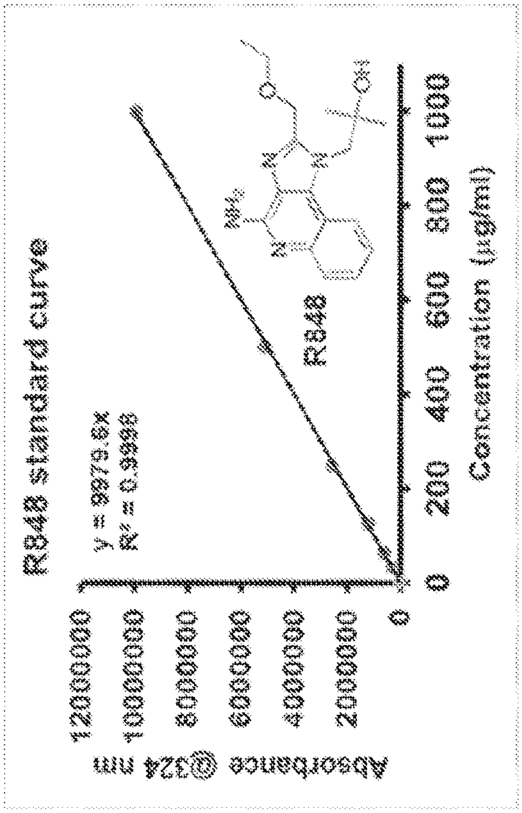
FIG. 16 shows the optical absorbance of R848 correlates with its concentration, and inset is the molecular structure of R848, according to an embodiment of the present invention.

FIG. 16 shows the optical absorbance of R848 correlates with its concentration, and inset is the molecular structure of R848, according to an embodiment of the present invention.

Table 3 exhibits the encapsulation efficiency and drug loading capability with different stirring time. The loading capability was 9.8% by simply mixing R848 with SFIC for 10 minutes. Increasing the time of ultrasonic stirring did not show significant influence on the loading capability. We will further explore drug loading methods for πOFs to improve the loading capability. For example, as SFIC can restore its crystalline structure after solvent annealing, R848 will be dissolved in the dichloromethane solution of SFIC and encapsulated in SFIC during the annealing process. Besides, we will also modify the chemical compounds of SFIC molecules to enhance the interaction between drug molecules and SFIC. Both hydrophobic and hydrophilic drugs can be encapsulated in the πOFs with tunable physical/chemical affinity due to the designable structure of the platform.

The encapsulation efficiency and drug loading capability of R848 in SFIC with different ultrasonic stirring time. Data are shown as mean±standard deviations (n=3).

TABLE 4

| Stirring time | Encapsulation efficiency | Drug loading capability |
|---|---|---|
| 10 min | 17.6% ± 1.1% | 9.8% ± 0.6% |
| 20 min | 17.5% ± 1.0% | 9.7% ± 0.6% |

Figure 17A:
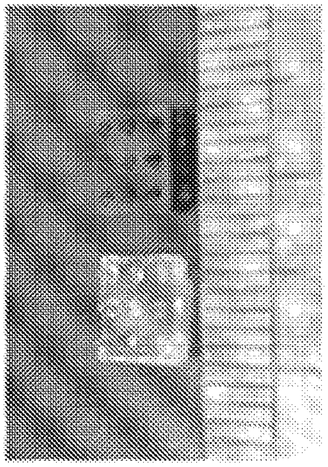
FIG. 17A shows dimensions of polymeric microneedles encapsulated in polyethylene glycol diacrylate matrix, according to an embodiment of the present invention.
Figure 17B:
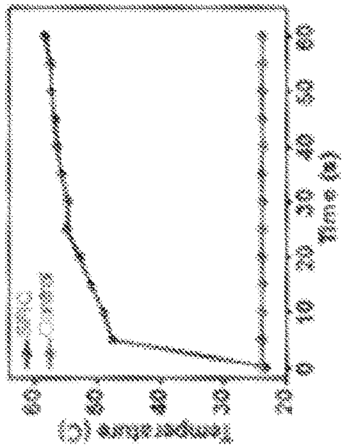
FIG. 17B displays the temperature increase of Poly(ethylene glycol) diacrylate (PEGDA) microneedles induced by the loaded SFIC under 671 nm laser ablation, according to an embodiment of the present invention.
Figure 17C:
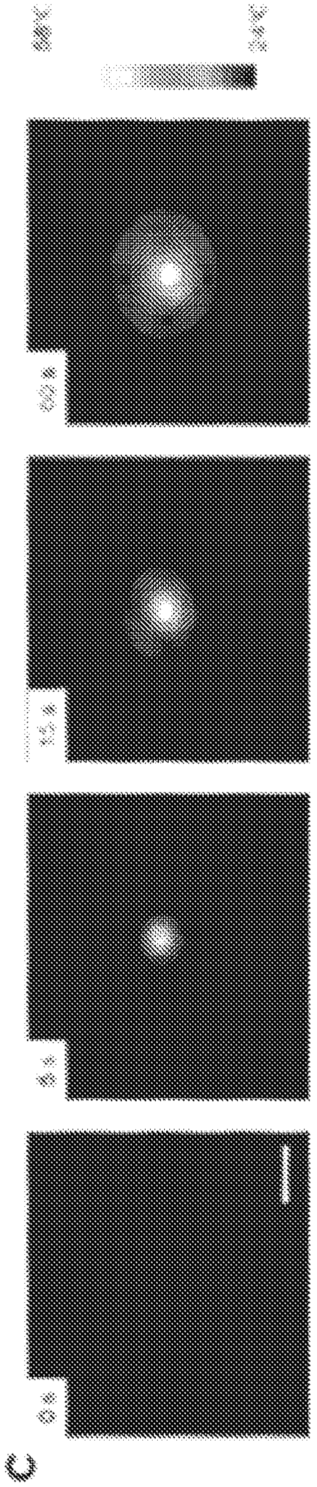
FIG. 17C shows thermal imaging of the microneedles, according to an embodiment of the present invention.

Photothermal effect of SFIC: πOFs can induce photothermal effect due to its strong absorption of light in or close to the near-infrared region. For example, SFIC has the maximum absorption at around 708 nm with its optical bandgap of 1.75 eV. We investigated the photothermal effect of SFIC encapsulated in polyethylene glycol diacrylate (PEGDA) microneedles as shown in FIG. 17A. FIG. 17A shows dimensions of polymeric microneedles encapsulated in polyethylene glycol diacrylate matrix, according to an embodiment of the present invention. Polymeric microneedles have been widely used for transdermal drug delivery. FIG. 17B displays the temperature increase of PEGDA microneedles induced by the loaded SFIC under 671 nm laser ablation, according to an embodiment of the present invention. The irradiation power was measured as 22.5 mW. The maximum temperature increased to more than 50° C. within 15 s, which can meet the requirement of hyperthermia (41-47° C.). The control group is pure PEGDA microneedles and did not show significant thermal effect under the same irradiation. Thermal imaging of microneedles was shown in FIG. 17C. Based on this feature, we will use SFIC as a photothermal agent for cancer therapy. We will also investigate the light-triggered release of antitumor drugs, such as R848, from SFIC. Moreover, to reduce the tissue toxicities of photothermal therapy, tissue-transparent second near-infrared light (1000-1350 nm) will be utilized. Compared to SFIC, πOFs with a narrower bandgap will be developed to absorb second near-infrared light for photothermal therapy and photoacoustic imaging.

FIGS. 14A-14C show the photothermal effect of SFIC in PEGDA microneedles, according to an embodiment of the present invention. FIG. 14A shows photographs of PEGDA microneedles w/o (left) or w/(right) SFIC, according to an embodiment of the present invention. FIG. 14B shows temperature curves of microneedles w/ or w/o SFIC under 671 nm laser ablation in 1 minute, according to an embodiment of the present invention. FIG. 14C shows thermal imaging of microneedles loaded with SFIC, scale bar, 5 mm, according to an embodiment of the present invention Further Embodiments: Our work is geared towards building upon our previous work on πOF derivatives and developing novel NIR porous materials. We can take advantage of spatial dimensionality in molecules and polarity differences of functional building blocks of small molecules. Increasing dimensionality with the use of branched scaffolds will enable us to generate functional structures that combine multiple conjugation pathways. We can vary the topology and molecular features (e.g., polarity and linking of building blocks) of small molecules to achieve desirable optical properties, better packing morphologies, enhanced inter- and intramolecular interactions, and predictable porous properties. We can design the ability to entrap drugs with high payloads and targeting and highly controllability of the drug release to avoid the 'burst effect' (important release within the first minutes). As these electronic and optical properties are the basis of NIR porous noncovalent crystalline materials, a clear understanding of structure-property relationships and assembly of in organic subunits can accelerate progress towards exploring efficient NIR porous noncovalent crystalline materials for controllable drug delivery.

Figure 18:
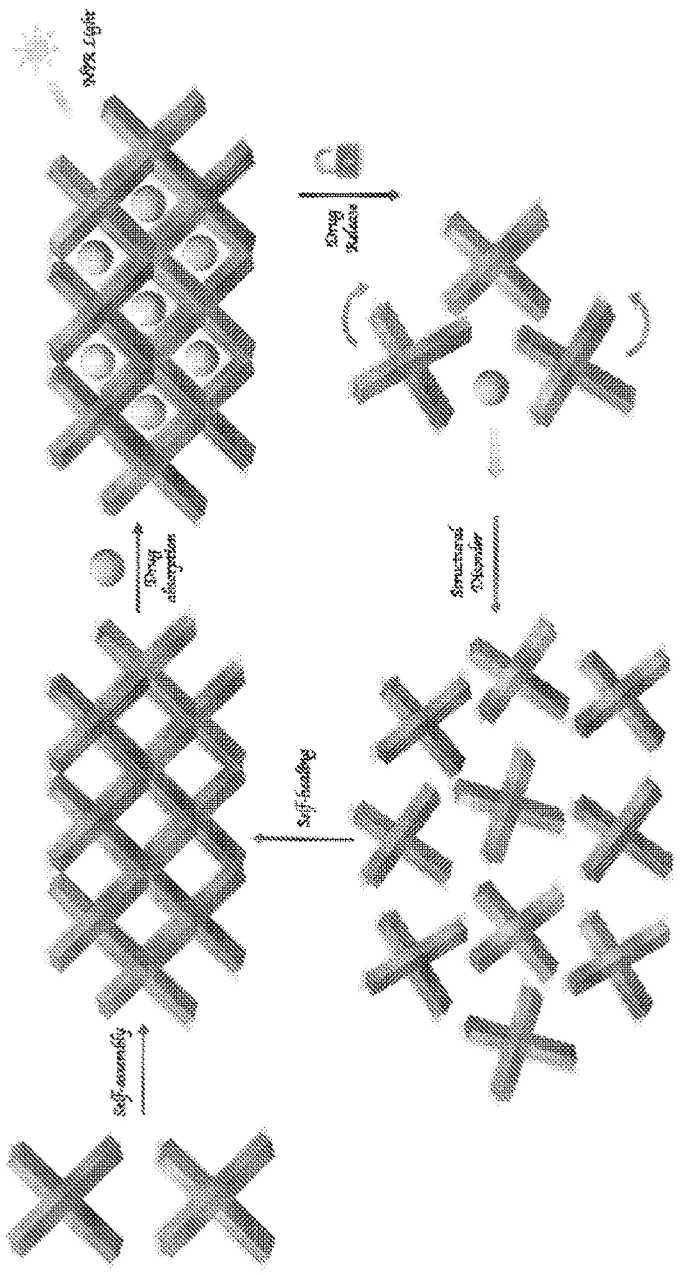
FIG. 18 is a schematic diagram for the drug delivery progress of πOF, according to an embodiment of the present invention.

FIG. 18 is a schematic diagram for the drug delivery progress of πOF, according to an embodiment of the present invention. (Due to the inherent labile feature of π···π interactions, the porous structures can collapse under the stimuli of light or heat and render burst release, achieving controllable release of the drug. On the other hand, the pore size of πOF can be tuned by direct slippage of units with π···π interaction, allowing the delivery and release of drugs with different molecular scales. Furthermore, since the absorption of πOF is usually in or close to the near-infrared region, it has a strong absorption of light and can thus induce photothermal effect, which may to some extent possess therapeutic applications with the drug delivery and release.)

We can use the antitumor efficacy of πOF-mediated drug delivery and photothermal therapy. The π···π stacking organic frames can collapse via external stimuli to release the drugs loaded in the materials πOFs. Optical excitation can be performed to trigger the drug release from πOFs as well as rendering photothermal therapeutic effects simultaneously. Based on this feature, multiple combinational therapeutics can be developed for cancer therapy. A B16F10 (ATCC® CRL-6475™) melanoma model can be developed in C57BL/6 mice (8-10 weeks old) and can be used to evaluate the antitumor efficacy leveraged by πOF-loaded microneedles (Mater. Horiz., 2020, 7, 3028-3033). R848 can be encapsulated in SFIC loaded in PEGDA microneedles that can be applied to the tumor site. We can first characterize the light-triggered transdermal delivery of R848 from the microneedle. R848 can alter the tumor microenvironment by driving the polarization of tumor-associated macrophages to an anti-tumorigenic phenotype. Flow cytometry can be performed to investigate the phenotype of macrophages before and after the transdermal administration of R848. We can also focus on the thermal effect induced by SFIC in the microneedle. The immunogenic death (ICD) of cancer cells can be studied by testing the expression of an ICD marker calreticulin. Tumor-associated antigens released during immunogenetic death of tumor cells can be engulfed by the anti-tumorigenic macrophages. This process can promote the cytotoxic activity of T cells against tumor cells and promote the efficacy of cancer therapy. The recruitment of cytotoxic T cells can be studied by flow cytometry and histological imaging. The antitumor efficacy can be evaluated by monitoring the tumor volume and mouse survival. The expression of antitumor cytokines can also be tested by enzyme-linked immunosorbent assay.

πOFs can also be used for NIR-triggered insulin administration. The insulin injection is required for people with type 1 and type 2 diabetes. Based on patient's blood glucose level, the dose of insulin should be adjusted to ensure efficacy and safety. NIR-triggered insulin administration can provide a convenient way for dose adjustment of insulin. Instead of syringe, microneedles can reduce the irritation of injection and have been developed for insulin delivery in animal models. We can first investigate the insulin encapsulation and release in πOFs. The insulin-πOF complex can be loaded in microneedles for transdermal delivery of insulin. The formulation of insulin-πOF complex and microneedles can be optimized to make sure NIR-triggered insulin release, which can be quantified by ELISA. We can further evaluate the efficacy of the proposed formulation by applying the microneedle to a diabetic mouse model. By monitoring the blood glucose level of the mouse model, the relationship between NIR radiation and insulin doses will be established (FIG. 19).

Figure 19:
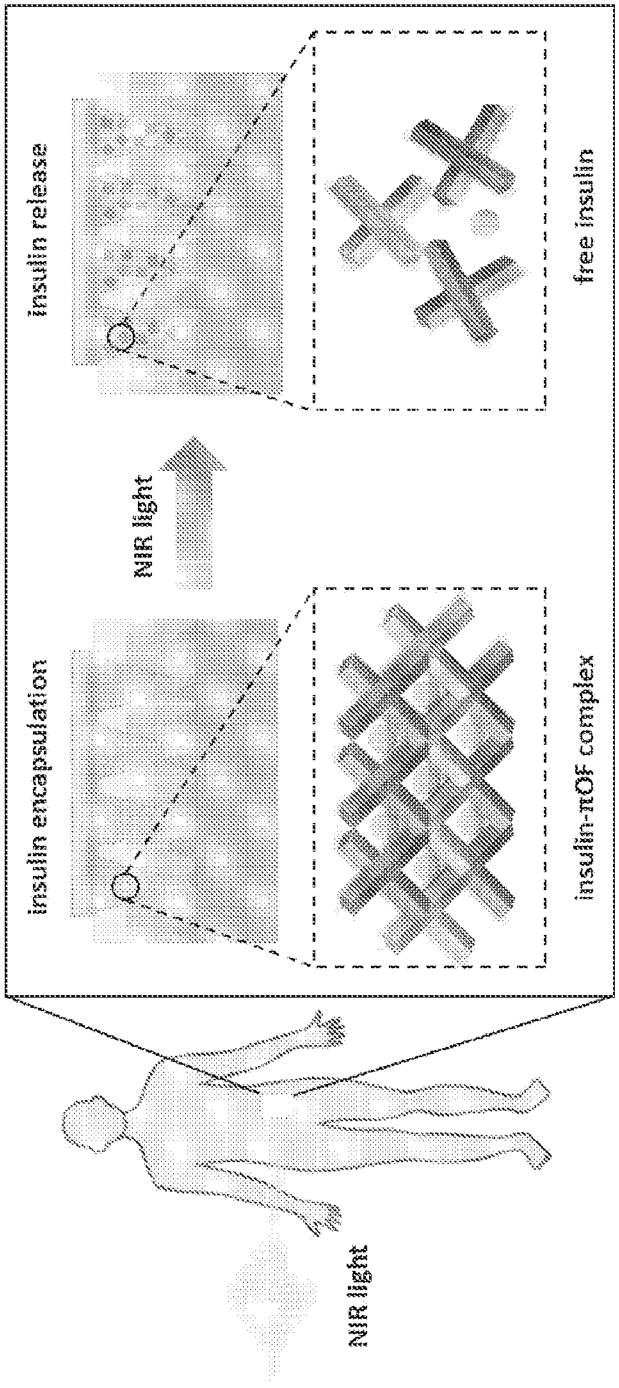
FIG. 19 is a schematic diagram for the NIR-triggered insulin delivery system using NIR-responsive πOF-loading microneedle-array patches, according to an embodiment of the present invention

FIG. 19 is a schematic diagram for the NIR-triggered insulin delivery system using NIR-responsive πOF-loading microneedle-array patches, according to an embodiment of the present invention. Insulin-πOF complexes are loaded into microneedle-array patches for painless and light-triggered insulin delivery, according to an embodiment of the present invention. Harmless NIR light wound induce the dissociation of Insulin-πOF complexes and realize controlled release of insulin when the bandgap of πOF molecule is narrowed by molecular engineering.

The attached documents provide various examples of the materials and devices described above and methods of synthesis and manufacture.

Astoundingly, PiOF may also have superconducting properties, which could endow the electronics, electrical, and magnetic related industry with a new perspective. In addition, PiOF may also have energy storage applications, such as the electrodes for supercapacitor and Li-ion batteries (or other batteries which use ions as charges, such as Na+ or Mg2+.)

REFERENCES AND NOTES

1. N. L. Rosi et al., Hydrogen storage in microporous metal-organic frameworks. *Science* 300, 1127-1129 (2003).
2. A. Corma, From microporous to mesoporous molecular sieve materials and their use in catalysis. *Chem. Rev.* 97, 2373-2419 (1997).
3. P. Horcajada et al., Porous metal-organic-framework nanoscale carriers as a potential platform for drug delivery and imaging. *Nat. Mater.* 9, 172-178 (2010).
4. A. C. McKinlay et al., BioMOFs: metal-organic frameworks for biological and medical applications. *Angew. Chem., Int. Ed.* 49, 6260-6266 (2010)
5. M. E. Davis, Ordered porous materials for emerging applications. *Nature* 417, 813-821 (2002).
6. C. Avci et al., Self-assembly of polyhedral metal-organic framework particles into three dimensional ordered superstructures. *Nat. Chem.* 10, 78-84 (2017).
7. T. Ma et al., Single-crystal X-ray diffraction structures of covalent organic frameworks. *Science* 361, 48-52 (2018).
8. J. A. R. Navarro, The dynamic art of growing COF crystals. *Science* 361, 35 (2018).
9. J. Jiang, Y. Zhao, O. M. Yaghi, Covalent chemistry beyond molecules. *J. Am. Chem. Soc.* 138, 3255-3265 (2016).
10. N. Huang, P. Wang, D. Jiang, Covalent organic frameworks: a materials platform for structural and functional designs. *Nat. Rev. Mater.* 1, 16068 (2016).
11. Y. He, S. Xiang, B. Chen, A microporous hydrogen-bonded organic framework for highly selective C2H2/C2H4 separation at ambient temperature. *J. Am. Chem. Soc.* 133, 14570 (2011).
12. P. Li et al., A rod-packing microporous hydrogen-bonded organic framework for highly selective separation of C2H2/CO2 at room temperature. *Angew. Chem. Int. Ed.* 54, 574-577 (2015).
13. F. Hu et al., An ultrastable and easily regenerated hydrogen-bonded organic molecular framework with permanent porosity. *Angew. Chem. Int. Ed.* 56, 2101-2104 (2017).
14. O. M. Yaghi, G. Li, H. Li, Selective binding and removal of guests in a microporous metalorganic framework. *Nature* 378, 703-706 (1995).
15. O. M. Yaghi, C. E. Davis, G. Li, H. Li, Selective guest binding by tailored channels in a 3-D porous zinc(II)-benzenetricarboxylate network. *J. Am. Chem. Soc.* 119, 2861-2868 (1997).
16. A. M. Evans et al., Seeded growth of single-crystal two-dimensional covalent organic Submitted Manuscript: Confidential frameworks. *Science* 361, 52-57 (2018).
17. M. Kondo et al., Rational synthesis of stable channel-like cavities with methane gas adsorption properties: [{Cu2(pzdc)2(L)}n](pzdc=pyrazine-2,3-dicarboxylate; L=a pillar ligand). *Angew. Chem. Int. Ed.* 38, 140-143 (1999).
18. K. Shen, et al., Ordered macro-microporous 5 metal-organic framework single crystals. *Science* 359, 206-210 (2018).
19. X. Chen et al., Lowering coefficient of friction in Cu alloys with stable gradient nanostructures. *Sci. Adv.* 2, e1601942 (2016).
20. A. P. Côté et al., Porous, crystalline, covalent organic frameworks. *Science* 310, 1166-117010 (2005).
21. Y Y. Lyu et al., Highly efficient red phosphorescent OLEDs based on non-conjugated silicon-cored spirobifluorene derivative doped with Ir-complexes. *Adv. Funct. Mater.* 19, 420-427 (2009).
22. N. Qiu et al., Nonfullerene small molecular acceptors with a three-dimensional (3D) structure for organic solar cells. *Chem. Mater.* 28, 6770-6778 (2016).
23. D. Heredia et al., Spirobifluorene-bridged donor/acceptor dye for organic dye-sensitized solar cells. *Org. Lett.* 12, 12-15 (2010).
24. G. Han, Y. Guo, L. Ning, Y. Yi, Improving the electron mobility of ITIC by end-group modulation: the role of fluorination and π-extension. *Sol. RRL.* 3, 1800251(2019).

25. Y. Lin, et al., An electron acceptor challenging fullerenes for efficient polymer solar cells. *Adv. Mater.* 27, 1170-1174 (2015).

26. G. Han, Y. Yi, Z. Shuai, From molecular packing structures to electronic processes: theoretical simulations for organic solar cells. *Adv. Energy Mater.* 8, 1702743 (2018).

27. C. G. Bezzu, M. Helliwell, J. E. Warren, D. R. Allan, N. B. McKeown, Heme-like coordination chemistry within nanoporous molecular crystals. *Science* 327, 1627-1630 (2010).

28. K. J. Msayib et al., Nitrogen and hydrogen adsorption by an organic microporous crystal. *Angew. Chem. Int. Ed.* 48, 3273-3277(2009). 29. Y. Chen, A. M. Kushner, G. A. Williams, Z Guan, Multiphase design of autonomic self-healing thermoplastic elastomers. *Nat. Chem.* 4, 467-472 (2012).

30. H. Yamagishi et al., Self-assembly of lattices with high structural complexity from a geometrically simple molecule. *Science* 361, 1242-1246 (2018).

31. P. Cordier, F. Tournilhac, C. Soulie-Ziakovic, L. Leibler, Self-healing and thermoreversible rubber from supramolecular assembly. *Nature* 451, 977-980 (2008).

32. L. Jiang, et al., Organic single-crystalline ribbons of a rigid "H"-type anthracene derivative and high-performance, short-channel field-effect transistors of individual micro/nanometer-sized ribbons fabricated by an "organic ribbon mask" technique. *Adv. Mater.* 20, 2735-2740 (2008).

33. D. A. Case, et al. (2012), AMBER 12, University of California, San Francisco.

34. I. Yavuz, B. N. Martin, J. Park, K. N. Houk, Theoretical Study of the Molecular Ordering, Paracrystallinity, And Charge Mobilities of Oligomers in Different Crystalline Phases. *J. Am. Chem. Soc.* 137, 2856-2866 (2015) and references therein.

35. Y. Tsutsui, et al., Unraveling Unprecedented Charge Carrier Mobility through Structure Property Relationship of Four Isomers of Didodecyl[1]benzothieno[3,2-b][1] benzothiophene. *Adv. Mater.* 28, 7106-7114 (2016) and references therein.

36. M. J. Frisch, et al. Gaussian 09, Revision D.01; Gaussian Inc: Wallingford, CT, 2009.

37. V. Rühle et al. Microscopic Simulations of Charge Transport in Disordered Organic Semiconductors. *J. Chem. Theory Comput.* 7, 3335-3345 (2011).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A composition comprising:

a π-π interaction-constructed organic framework (pi-OF), comprising:

a plurality of molecular structures, each molecular structure, comprising:

a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each multijoint fragment unit comprising a 3-(dicyanomethylidene) indan-1-one (IC) unit, each IC unit is used as an end group (EG) to each end of the two spirobifluorene (SF) units;

wherein said each IC unit is configured to interact via a π-π interaction with a neighboring IC unit of an adjacent molecular structure or to interact via a CH— interaction with neighboring aromatic group (R1) of an adjacent molecular structure, or both; a bioactive agent absorbed into said π-OF, and wherein the two SF units forming a rigid biplanar conjugated cruciform-shaped spirobifluorene are selected from the group consisting of

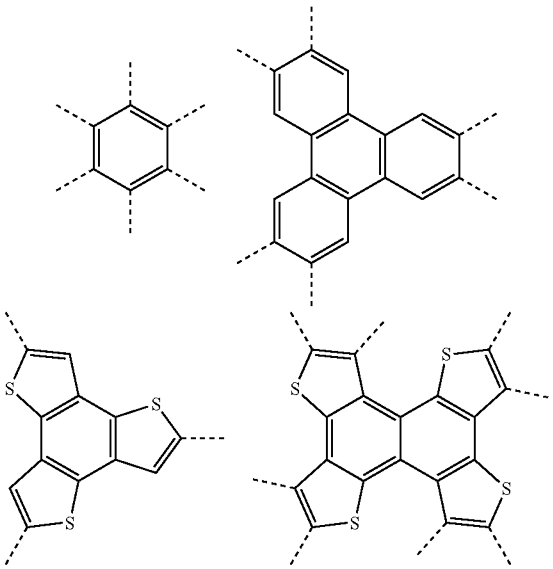

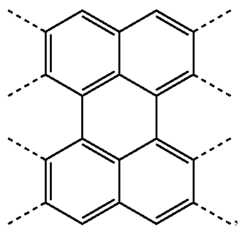

, and

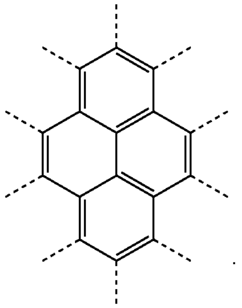

.

2. The composition according to claim 1, wherein the rigid biplanar conjugated cruciform-shaped spirobifluorene forms a rigid three-dimensional structure.

3. The composition according to claim 1, wherein the SF has a spiro-conjugated structure acting as a tetrahedral node.

4. The composition according to claim 1, further comprising thiophene units to increase a π-conjugated plane of each SF unit.

5. The composition according to claim 1, wherein said each IC unit is a chromophore configured to absorb or emit radiation.

6. The composition according to claim 1, wherein each molecular structure exhibits a tetragonal-disphenoid-shaped molecular conformation and configured to self-assemble into a 3D porous structure.

7. The composition according to claim 1, wherein each molecular structure has thermal stability after heat treatment.

8. The composition according to claim 1, wherein each molecular structure is connected to four adjacent molecular structures.

9. The composition according to claim 8, wherein the adjacent molecular structures are rotated by 90 degrees relative to said each molecular structure.

10. The composition according to claim 1, wherein each molecular structure is connected to four adjacent molecular structures through four pairs of π···π interactions through antiparallel EGs.

11. The composition according to claim 1, wherein the π-π interaction, constructed organic framework forms a final three-dimensional lamellar structure.

12. The composition according to claim 1, comprises a plurality of 2D layers, wherein an orientation of molecular structures of adjacent 2D layers are identical and assemble into two repeating layers.

13. The composition according to claim 1, wherein the π-OF forms a porous 3D structure that is held together by π···π interactions and further enhanced by intermolecular CH···π interactions.

14. A molecular structure (SFIC), comprising:

a centroid core having two spirobifluorene (SF) units, the two SF units forming a rigid biplanar conjugated cruciform-shaped spirobifluorene, the two SF units forming an essentially orthogonal configuration; and a plurality of multijoint fragment units, each unit comprising a 3-(dicyanomethylidene)indan-1-one (IC) unit, each IC unit is used as an end group (EG) to each end of the two spirobifluorene (SF) units, wherein said each IC unit is configured to interact via a π-π interaction with a neighboring IC unit of an adjacent molecular structure or to interact via a CH-interaction with neighboring aromatic group (R1) of an adjacent molecular structure, or both, and wherein the two SF units forming a rigid biplanar conjugated cruciform-shaped spirobifluorene are selected from the group consisting of

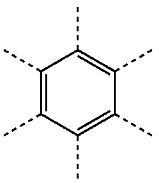
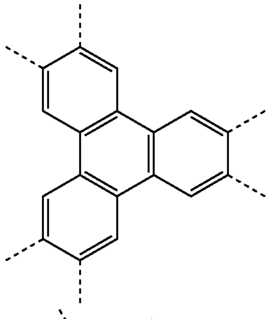
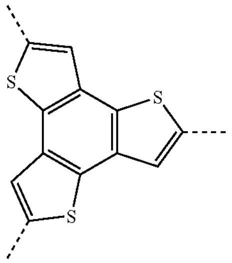
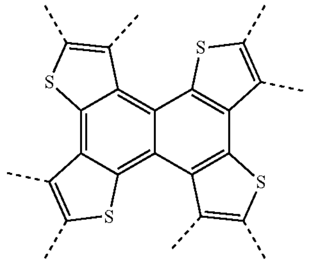

-continued

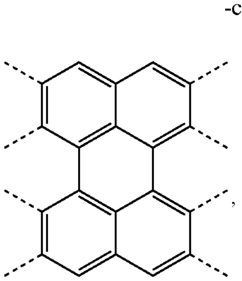
, and
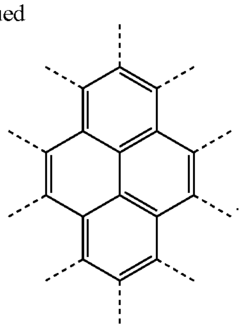

15. The molecular structure according to claim 14, wherein the rigid biplanar conjugated cruciform-shaped spirobifluorene forms a rigid three-dimensional structure.

16. The molecular structure according to claim 14, wherein each SF unit has a spiro-conjugated structure acting as a tetrahedral node.

17. The molecular structure according to claim 14, further comprising thiophene units provided to increase a π-conjugated plane of each SF unit.

18. The molecular structure according to claim 14, wherein said each IC unit is a chromophore configured to absorb or emit radiation.

19. The molecular structure according to claim 14, wherein each molecular structure exhibits a tetragonal-disphenoid-shaped molecular conformation and is configured to self-assemble into a 3D porous structure.

20. The molecular structure according to claim 14, wherein R1 is selected from the group consisting of:

$R_1$ =
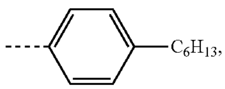
and $R_1$ =
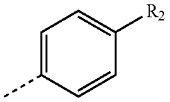
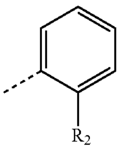
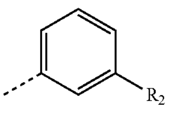
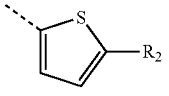
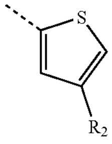
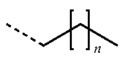
, n = 1-20 wherein $R_2$ is an alkyl chain.

21. The molecular structure according to claim 14, wherein said each IC unit and end group (EG) is selected from the group consisting of:

-continued
IC
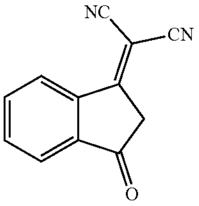
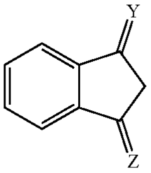
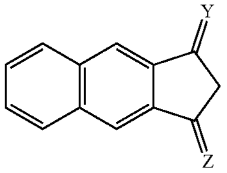
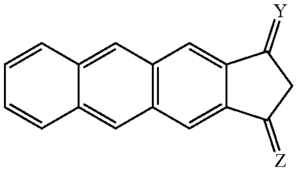
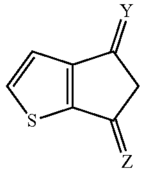
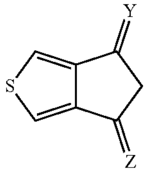
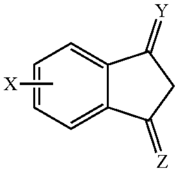
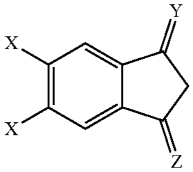
X = Me, F, Cl, Br, I
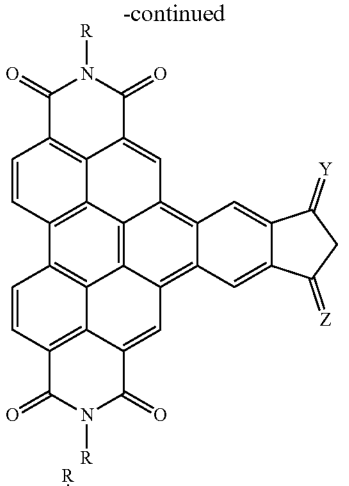
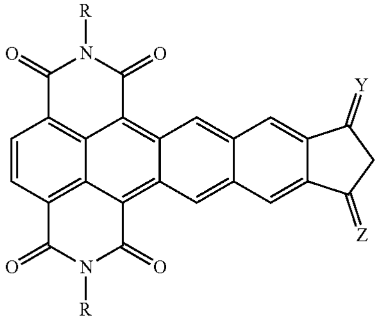
R = Any side chain
Y or Z = O or 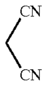 Y and Z could be same or different.
* * * * *